US010941388B2

(12) United States Patent
Singer et al.

(10) Patent No.: US 10,941,388 B2
(45) Date of Patent: Mar. 9, 2021

(54) CELLULASE COMPLEX, AND GLYCOSIDASE HYDROLASES THEREOF, AND METHODS OF USING THEREOF

(71) Applicants: The Regents of the University of California, Oakland, CA (US); National Technology & Engineering Solutions of Sandia, LLC, Albuquerque, NM (US)

(72) Inventors: Steven W. Singer, Oakland, CA (US); Sebastian D. Kolinko, Basel (CH); Evelyn Denzel, Laupheim (DE); Jennifer Hiras, Corning, NY (US); John M. Gladden, Alameda, CA (US)

(73) Assignees: The Regents of the University of California, Oakland, CA (US); National Technology & Engineering Solutions of Sandia, LLC, Albuquerque, NM (US)

( * ) Notice: Subject to any disclaimer, the term of this patent is extended or adjusted under 35 U.S.C. 154(b) by 20 days.

(21) Appl. No.: 15/985,216

(22) Filed: May 21, 2018

(65) Prior Publication Data

US 2018/0371443 A1 Dec. 27, 2018

Related U.S. Application Data

(63) Continuation of application No. PCT/US2016/063198, filed on Nov. 21, 2016.

(60) Provisional application No. 62/257,477, filed on Nov. 19, 2015.

(51) Int. Cl.

| | |
|---|---|
| ***C12P 19/02*** | (2006.01) |
| ***C12N 9/42*** | (2006.01) |
| ***C12P 19/14*** | (2006.01) |
| ***C12P 7/64*** | (2006.01) |
| ***C12N 9/24*** | (2006.01) |
| *C12N 15/63* | (2006.01) |

(52) U.S. Cl.

CPC ......... *C12N 9/2437* (2013.01); *C12N 9/2402* (2013.01); *C12N 9/2482* (2013.01); *C12N 9/2491* (2013.01); *C12P 7/649* (2013.01); *C12P 19/02* (2013.01); *C12P 19/14* (2013.01); *C12N 15/63* (2013.01); *C12Y 302/01004* (2013.01); *C12Y 302/01008* (2013.01); *C12Y 302/01025* (2013.01); *Y02E 50/10* (2013.01)

(58) Field of Classification Search

CPC ....................................................... C12P 19/02

See application file for complete search history.

(56) References Cited

FOREIGN PATENT DOCUMENTS

WO 2017087982 A2 5/2017

OTHER PUBLICATIONS

Li et al.,"Comparison of dilute acid and ionic liquid pretreatment of switchgrass: Biomass recalcitrance, delignification and enzymatic saccharification, Bioresource Technology." vol. 101, pp. 4900-4906 (2010).

Gladden et al., "Glycoside hydrolase activities of thermophilic bacterial consortia adapted to switchgrass." Applied and Environmental Microbiology. vol. 77, pp. 5804-5812 (2011).

Morag et al., "Affinity digestion for the near-total recovery of purified cellulosome from Clostridium thermocellum." Enzyme and Microbial Technology. vol. 14, pp. 289-292 (1992).

Laemmli et al., "Cleavage of Structural Proteins during the Assembly of the Head of Bacteriophage T4." Nature. vol. 227, pp. 680-685 (1970).

Schwarz et al., "Activity staining of cellulases in polyacrylamide gels containing mixed linkage β-glucans." Analytical Biochemistry. vol. 164, pp. 72-77 (1987).

Park et al., "A Thermophilic Ionic Liquid-Tolerant Cellulase Cocktail for the Production of Cellulosic Biofuels." PLoS ONE 7, e37010 (2012).

Huber et al., "Bellerophon: a program to detect chimeric sequences in multiple sequence alignments." Bioinformatics (Oxford, England). vol. 20, pp. 2317-2319 (2004).

Sunna et al., "A novel thermostable multidomain 1,4-βxylanase from 'Caldibacillus cellulovorans' and effect of its xylan-binding domain on enzyme activity", Microbiology 146: 2947-2955 (2000).

Shi et al., "One-pot ionic liquid pretreatment and saccharification of switchgrass", Green Chemistry 15:2579-2589 (2013).

*Primary Examiner* — Tekchand Saidha

(74) *Attorney, Agent, or Firm* — Robin C. Chiang; Lawrence Berkeley National Laboratory

(57) ABSTRACT

The present invention provides for a purified or isolated cellulase complex comprising two or more glycosidase hydrolase, or enzymatically active fragment thereof, selected from the group consisting of a GH9 polypeptide, a GH48 polypeptide, a GH10 polypeptide, and a GH6 polypeptide, and optionally a GH10_2 polypeptide and/or an AA10 polypeptide.

8 Claims, 7 Drawing Sheets

Specification includes a Sequence Listing.

```
58  KAIYFYDAQRSGKLPPDNRVEWRGDSGLNDGADVGVDLTGGWYDAGDHVKFGLPMAYSAA
    KAI FY+ Q SGKLP   R  WRGDS L DG D G+DLTGGW+DAGDHVKF LPM+Y+
43  KAIMFYEFQMSGKLPSWVRNNWRGDSALKDGQDNGLDLTGGWFDAGDHVKFNLPMSYTGT

118 MLAWAVYEYRDAFVQTGQLDYILNNIKWATDYFIKAHSAPNVLWGQVGKGDVDHAWWGPA
    ML+WAVYEY+DAFV++GQL++ILN I+W  DYF+K H +   V + QVG G  DHAWWGPA
103 MLSWAVYEYKDAFVKSGQLEHILNQIEWVNDYFVKCHPSKYVYYYQVGDGSKDHAWWGPA

178 EVMQMPRPAYKIDPSCPGSDLAAGTAAAMAAAAAVFKPTDPTYASTLIAHAKQLYTFADT
    EVMQM RP++K+  S PGS + A TAA++AAA+ V K  +PT A+T + HAK LY FA+
163 EVMQMERPSFKVTQSSPGSTVVAETAASLAAASIVLKDRNPTKAATYLQHAKDLYEFAEV

238 YRGKYSDCITDAQNFYRSWSGYADELTWGAVWLYLATGEQAYLDKAIASVAEWGREGQTP
       K     T A  +Y SWSG+ DEL+W AVWLYLAT +  YL KA + V  W +   +
223 --TKSDSGYTAANGYYNSWSGFYDELSWAAVWLYLATNDSTYLTKAESYVQNWPKISGSN

298 YWGYKWTQSWDDVHYGAQLLLARITGDQRFIQSTERNLEYWTDGTDDTGERITYTPGGLA
       YKW   WDDVH GA LLLA+ITG   + Q  E +L+YWT G +  GERI YTP GLA
281 TIDYKWAHCWDDVHNGAALLLAKITGKDTYKQIIEMHLDYWTTGYN--GERIKYTPKGLA

358 WLDSWGSLRYAMNASFLAFVYSDWLQSRDPAKAEKYRNFAVRQVLYALGDNPRNSSYVVG
    WLD WGSLRYA   +FLAFVYSDW       K E YR F   Q+ YALG   R  S+VVG
339 WLDQWGSLRYATTTAFLAFVYSDWAGC-PSTKKETYRKFGESQIDYALGSAGR--SFVVG

418 FGRNPPQRPHHRTAHGSWADSQNVPAYHRHILYGA  452
    FG NPP+RPHHRTAH SWADSQ++P+YHRH LYGA
396 FGTNPPKRPHHRTAHSSWADSQSIPSYHRHTLYGA  430
```

FIG. 5

```
48  FKDRFLQLYNQIKNPANGYFSPEGIPYHSIETLISEAPDYGHMTTSEAFSYWLWLETLYG
    +  RF+ L+N+I +PANGYF+ +GIPYHS+ETLI EAPDYGH+TTSEAFSY++WLE +YG
1128YGQRFMWLWNKIHDPANGYFNQDGIPYHSVETLICEAPDYGHLTTSEAFSYYVWLEAVYG

108 YFTGDWSKLEQAWTKMEQFIIPNSTEQPTMGSYNPSSPATYAPEHPYPDRYPTLLNNSVP
      TGDWSK + AW  +E+++IP++ +QP + SY+P+ PATYA E   PD+YP+ L  +VP
1188KLTGDWSKFKTAWDTLEKYMIPSAEDQP-IRSYDPNKPATYAGEWETPDKYPSPLEFNVP

168 AGQDPLDAELKATYGNNVTYLMHWLLDVDNWYGFGNLLNPSHTATYVNTFQRGEQESVWE
     G+DPL  EL +TYG+ + Y MHWL+DVDNWYG+G   +    A+++NTFQRG +ESVWE
1247VGKDPLHNELVSTYGSTLMYGMHWLMDVDNWYGYGKRGDGVSRASFINTFQRGPEESVWE

228 AITHPSQDNFRFGKPNEGFVTLFVKDNGTPAQQWRYTAASDADARAIQVMYWAK-----Q
     + HPS + F++G PN GF+ LF+KD    ++QWRYT A DADARAIQ  YWAK     Q
1307TVPHPSWEEFKWGGPN-GFLDLFIKDQNY-SKQWRYTDAPDADARAIQATYWAKVWAKEQ

283 LGYNN-QTYLDKARKMGDYLRYTLFDKYFQQIGSANDGSPSPGSGKNSAHYLLSWYTAWG
      +N   +Y+ KA KMGDYLRY +FDKYF+ +G   D + + G+G +SAHYLLSWY AWG
1365GKFNEISSYVAKAAKMGDYLRYAMFDKYFKPLG-CQDKNAAGGTGYDSAHYLLSWYYAWG

342 GGLGSGGNWAWRIGSSHAHQGYQNPVAAYALS-AGGLAPRSATAQTDWATSLQRQLEFYT
    G L   G W+W+IG SHAH GYQNP+AA+AL+    + P+S T   DWA SL+RQ+EFY
1424GALD--GAWSWKIGCSHAHFGYQNPMAAWALANDSDMKPKSPTGANDWAKSLKRQIEFYR

401 WLQSSEGAIGGGATNSVGGSYQPYPSGRSTFYGMVYDEAPVYRDPPSNSWFGFQAWSVER
    WLQS+EGAI GGATNS  G Y+ YP+G +TFYGM Y+  PVYRDP SN+WFGFQAWS++R
1482WLQSAEGAIAGGATNSWNGRYEKYPAGTATFYGMAYEPNPVYRDPGSNTWFGFQAWSMQR

461 VAELYYIWTSSGNTNTQQFQMVKNIVTKWVDWALDYTFVNQRPVTDAQGYFLTSSGSRVL
    VAE YY+   +G+ +         ++ KWV W
1542VAEYYYV---TGDKDAGA------LLEKWVSWI---------------------------

521 GGNNFQIATVSDPGQFYIPSTLEWQGQPDTWNGYANYTGNPNFHAIAKDPGQDVGVTGNY
          +  ++   G F IPSTL+W GQPDTW G   YTGNPN H    D G D+G+T +
1566----KSVVKLNSDGTFAIPSTLDWSGQPDTWKG--TYTGNPNLHVKVVDYGTDLGITASL

581 IKLLTFFAAATKAETGNYTALGSQALNVAEQLLNVLWN-FNDGVGIVRPEQRADYFRYFT
       L +++A TK     Y     +A N+A++LL+ +W  + D  G+  PE+RADY R+F
1620ANALLYYSAGTK----KYGVFDEEAKNLAKELLDRMWKLYRDNKGLSAPEKRADYKRFFE

640 KEIYFPSGWSGTYGQGNTIPGPGAVPSDPSKGGNGVYISYAELRPKIKQDPKWSYLENLY
    +E+Y P+GW+G    G+ I           K G    + + ++R K KQDP W  LE  Y
1676QEVYIPAGWTGKMPNGDVI-----------KSG----VKFIDIRSKYKQDPDWPKLEAAY

700 KTSYNPSTGRWENGVPTFTYHRFWAQVDVATAYAEFARLIG  740
    K+            VP F YHRFWAQ D+A A A +  L G
1721KSG----------QVPEFRYHRFWAQCDIAIANATYEILFG  1751
```

FIG. 6

20  MVAALLVF--TVSVVPPKEADAGLAKTKFLGNVINNSIPSDFAVYWNQVTPENATKWGSV
    + A+LL+     S +   +ADAGLA++KFLGNVI +S+PS+FA YWNQVTPEN+TKWGSV
9   ICASLLLLGSVFSFIATSDADAGLARSKFLGNVIASSVPSNFATYWNQVTPENSTKWGSV

78  ESSRDNMNWSTADMIYNYARSNGFPFKFHTLVWGSQEPGWISGLSAAEQQAEVIEWIQAA
    E++R+ MNWS AD+ YNYA+SNGFPFKFHTLVWGSQ+PGWISGLS AEQ+AEV++WIQAA
69  EATRNVMNWSAADLAYNYAKSNGFPFKFHTLVWGSQQPGWISGLSQAEQKAEVLQWIQAA

138 GQRYPDADFVDVVNEPLHAKPSYRNAIGGDGSTGWDWVIWSFEQARRAFPNSKLLINEYG
    GQRYP+ADFVDVVNEPLHAKPSYRNAIGGDG+TGWDWVIWSF++AR+AFPN+KLLINEYG
129 GQRYPNADFVDVVNEPLHAKPSYRNAIGGDGATGWDWVIWSFQEARKAFPNAKLLINEYG

198 VENDPNAASQYVQIINLLKSRGLIDGIGIQGHYFNLDTVSVSTLRTTLGMLAETGLPIYV
    + +DPNAA+QYVQIINLLKSRGLIDGIGIQ HYFN+D+VSVST+ + L  LA TGLPIYV
189 IISDPNAANQYVQIINLLKSRGLIDGIGIQCHYFNMDSVSVSTMNSVLNTLAATGLPIYV

258 SELDISGDDATQLARYQEKFPILWEHPSVQGITLWGYIEGQTWRSGTHLITASGVERPAL
    SELD++GDD+TQLARYQ+KFP+LWEH +V+G+TLWGYIEGQTW S THL+ ++G ERPAL
249 SELDMTGDDSTQLARYQQKFPVLWEHSAVKGVTLWGYIEGQTWASNTHLVRSNGTERPAL

318 QWLRTYLA  325
    QWLRTYL+
309 QWLRTYLS  316

FIG. 7

1   MNRRLIARLSGMLAMVLIAAVLAYVPKPEPAEAHGGMVFPATRTYACYVDGKVHGNGGDL
    MNRRLIARLSGMLAMVLIAA+LAYVPKPEPAEAHGGMVFPATRTYACYVDGKVHGNGGDL
1   MNRRLIARLSGMLAMVLIAAMLAYVPKPEPAEAHGGMVFPATRTYACYVDGKVHGNGGDL

61  NMINPACLDALAISGNYQFWNWFGNLISNAGGRHREIIPDGKLCGPTASFDGMNQARTDW
    NMINPACLDALAISGNYQFWNWFGNLISNAGGRHREIIPDGKLCGPTASFDGMNQARTDW
61  NMINPACLDALAISGNYQFWNWFGNLISNAGGRHREIIPDGKLCGPTASFDGMNQARTDW

121 WTTRLQPGATITVRVNAWAPHPGTWYLYVTRDGWDPTQPLKWSDLEPTPFSQVTNPPINS
    WTTRLQPGATITVRVNAWAPHPGTWYLYVTRDGWDPTQPLKWSDLEPTPFSQVTNPPINS
121 WTTRLQPGATITVRVNAWAPHPGTWYLYVTRDGWDPTQPLKWSDLEPTPFSQVTNPPINS

181 SGPDGAEYSWQVQLPNKQGRHIIYMIWQRSDSPEAFYNCSDAYFGSGPIAYEFGDPREGG
    SGPDGAEYSWQVQLPNKQGRHIIYMIWQRSDSPEAFYNCSD YFGSGPIAYEFGDPREGG
181 SGPDGAEYSWQVQLPNKQGRHIIYMIWQRSDSPEAFYNCSDVYFGSGPIAYEFGDPREGG

CELLULASE COMPLEX, AND GLYCOSIDASE HYDROLASES THEREOF, AND METHODS OF USING THEREOF

CROSS-REFERENCE TO RELATED APPLICATIONS

The application claims priority as a continuation application to PCT International Patent Application No. PCT/US16/63198, filed Nov. 21, 2016, which claims priority to U.S. Provisional Patent Application Ser. No. 62/257,477, filed Nov. 19, 2015; both of which are incorporated herein by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of saccharification of biomass using ionic liquid.

BACKGROUND OF THE INVENTION

JTherm is a mixture of enzymes useful as a thermophilic-ionic liquid (IL) tolerant cellulase cocktail. This cocktail is useful in biofuel production based on its application in the production of biodiesel (fatty acid ethyl esters) from switchgrass and its application in pretreatment/saccharification for switchgrass.

SUMMARY OF THE INVENTION

The present invention provides for a composition compressing a purified or isolated cellulase complex comprising two or more glycosidase hydrolase, or enzymatically active fragment thereof, selected from the group consisting of a GH9 polypeptide comprising an amino acid sequence at least 70% identical to SEQ ID NO:1, a GH48 polypeptide comprising an amino acid sequence at least 70% identical to SEQ ID NO:2, a GH10 polypeptide comprising an amino acid sequence at least 70% identical to SEQ ID NO:3, and a GH6 polypeptide comprising an amino acid sequence at least 70% identical to SEQ ID NO:4; and optionally the composition or the cellulase complex comprising a GH10_2 polypeptide comprising an amino acid sequence at least 70% identical to SEQ ID NO:5, and/or an AA10 polypeptide comprising an amino acid sequence at least 70% identical to SEQ ID NO:6.

In some embodiments, the purified or isolated cellulase complex comprises the following glycosidase hydrolases, or enzymatically active fragment thereof: a GH9 polypeptide comprising an amino acid sequence at least 70% identical to SEQ ID NO:1, a GH48 polypeptide comprising an amino acid sequence at least 70% identical to SEQ ID NO:2, a GH10 polypeptide comprising an amino acid sequence at least 70% identical to SEQ ID NO:3, and a GH6 polypeptide comprising an amino acid sequence at least 70% identical to SEQ ID NO:4.

In some embodiments, the purified or isolated cellulase complex comprises the following glycosidase hydrolases, or enzymatically active fragment thereof: a GH9 polypeptide comprising an amino acid sequence at least 90% identical to SEQ ID NO:1, a GH48 polypeptide comprising an amino acid sequence at least 90% identical to SEQ ID NO:2, a GH10 polypeptide comprising an amino acid sequence at least 90% identical to SEQ ID NO:3, and a GH6 polypeptide comprising an amino acid sequence at least 90% identical to SEQ ID NO:4.

In one embodiment, the purified or isolated cellulase complex comprises a GH9 polypeptide comprising the amino acid sequence of SEQ ID NO:1, a GH48 polypeptide comprising the amino acid sequence of SEQ ID NO:2, a GH10 polypeptide comprising the amino acid sequence of SEQ ID NO:3, and a GH6 polypeptide comprising the amino acid sequence of SEQ ID NO:4.

In some embodiments, the GH9 polypeptide comprising an amino acid sequence at least 75%, 80%, 85%, 90%, 95%, or 99% identical to SEQ ID NO:1. In some embodiments, the GH9 polypeptide comprises the amino acid sequence of SEQ ID NO:1. In some embodiments, the GH9 polypeptide comprises one or more of the conserved amino residues depicted in FIG. 5. In some embodiments, the GH9 polypeptide comprises one or more of the identical amino residues depicted in FIG. 5, which are in stretches of three or more, or four or more, consecutive identical amino acid residues. In some embodiments, the GH9 polypeptide comprises residues 58 to 452 of SEQ ID NO:1, or residues 43 to 430 of SEQ ID NO:8.

In some embodiments, the GH9 polypeptide comprising an amino acid sequence at least 70% identical to SEQ ID NO:1, or enzymatically active fragment thereof, wherein the amino acid sequence comprises one or more of the following amino acid sequences: SGKLP (SEQ ID NO:13), WRGDS (SEQ ID NO:14), DLTGGW (SEQ ID NO:15), DAGDHVKF (SEQ ID NO:16), WAVYEY (SEQ ID NO:17), DHAWWGPA (SEQ ID NO:18), EVMQM (SEQ ID NO:19), AVWLYLAT (SEQ ID NO:20), WDDVH (SEQ ID NO:21), GLAWLD (SEQ ID NO:22), WGSLRYA (SEQ ID NO:23), FLAFVYSDW (SEQ ID NO:24), RPHHRTAH (SEQ ID NO:25), and SWADSQ (SEQ ID NO:26).

In some embodiments, the GH48 polypeptide comprising an amino acid sequence at least 75%, 80%, 85%, 90%, 95%, or 99% identical to SEQ ID NO:2. In some embodiments, the GH48 polypeptide comprises the amino acid sequence of SEQ ID NO:2. In some embodiments, the GH48 polypeptide comprises one or more of the identical amino residues depicted in FIG. 6. In some embodiments, the GH48 polypeptide comprises one or more of the identical amino residues depicted in FIG. 6, which are in stretches of three or more, or four or more, consecutive identical amino acid residues. In some embodiments, the GH48 polypeptide comprises residues 48 to 740 of SEQ ID NO:2, or residues 1128 to 1751 of SEQ ID NO:9.

In some embodiments, the GH48 polypeptide comprising an amino acid sequence at least 70% identical to SEQ ID NO:2, or enzymatically active fragment thereof, wherein the amino acid sequence comprises one or more of the following amino acid sequences: PANGYF (SEQ ID NO:27), GIPYHS (SEQ ID NO:28), EAPDYGH (SEQ ID NO:29), TTSEAFSY (SEQ ID NO:30), TGDWSK (SEQ ID NO:31), PATYA (SEQ ID NO:32), DVDNWYG (SEQ ID NO:33), NTFQRG (SEQ ID NO:34), ESVWE (SEQ ID NO:35), QWRYT (SEQ ID NO:36), DADARAIQ (SEQ ID NO:37), KMGDYLRY (SEQ ID NO:38), FDKYF (SEQ ID NO:39), SAHYLLSWY (SEQ ID NO:40), GYQNP (SEQ ID NO:41), GGATNS (SEQ ID NO:42), TFYGM (SEQ ID NO:43), PVYRDP (SEQ ID NO:44), WFGFQAWS (SEQ ID NO:45), GQPDTW (SEQ ID NO:46), YTGNPN (SEQ ID NO:47), and YHRFWAQ (SEQ ID NO:48).

In some embodiments, the GH10 polypeptide comprising an amino acid sequence at least 75%, 80%, 85%, 90%, 95%, or 99% identical to SEQ ID NO:3. In some embodiments, the GH10 polypeptide comprises the amino acid sequence of SEQ ID NO:3. In some embodiments, the GH10 polypeptide comprises one or more of the identical amino acid residues when comparing all of the amino acid residues of SEQ ID NO:3 and amino acid residues SEQ ID NO:12 (but excluding amino acid residues 1 to 12). In some embodiments, the GH10 polypeptide comprises SEQ ID NO:3, or SEQ ID NO:12 (but excluding amino acid residues 1 to 12).

In some embodiments, the GH10_2 polypeptide comprising an amino acid sequence at least 75%, 80%, 85%, 90%, 95%, or 99% identical to SEQ ID NO:5. In some embodiments, the GH10_2 polypeptide comprises the amino acid sequence of SEQ ID NO:5. In some embodiments, the GH10_2 polypeptide comprises one or more of the identical amino residues depicted in FIG. 7. In some embodiments, the GH10_2 polypeptide comprises one or more of the identical amino residues depicted in FIG. 7, which are in stretches of three or more, or four or more, consecutive identical amino acid residues. In some embodiments, the GH10_2 polypeptide comprises residues 48 to 740 of SEQ ID NO:5, or residues 1128 to 1751 of SEQ ID NO:10.

In some embodiments, the GH10_2 polypeptide comprising an amino acid sequence at least 70% identical to SEQ ID NO:5, or enzymatically active fragment thereof, wherein the amino acid sequence comprises one or more of the following amino acid sequences: ADAGLA (SEQ ID NO:49), KFLGNVI (SEQ ID NO:50), YWNQVTPEN (SEQ ID NO:51), TKWGSVE (SEQ ID NO:52), SNGFPFKFHTLVWGSQ (SEQ ID NO:53), PGWISGLS (SEQ ID NO:54), WIQAAGQRYP (SEQ ID NO:55), aDFVDVVNEPLHAKPSYRNAIGGDG (SEQ ID NO:56), TGWDWVIWSF (SEQ ID NO:57), KLLINEYG (SEQ ID NO:58), DPNAA (SEQ ID NO:59), QYVQIINLLKSRGLIDGIGIQ (SEQ ID NO:60), VSVST (SEQ ID NO:61), TGLPIYVSELD (SEQ ID NO:62), TQLARYQ (SEQ ID NO:63), TLWGYIEGQTW (SEQ ID NO:64), ERPALQWLRTYL (SEQ ID NO:65).

In some embodiments, the GH6 polypeptide comprising an amino acid sequence at least 75%, 80%, 85%, 90%, 95%, or 99% identical to SEQ ID NO:4. In some embodiments, the GH6 polypeptide comprises the amino acid sequence of SEQ ID NO:4.

In some embodiments, the AA10 polypeptide comprising an amino acid sequence at least 75%, 80%, 85%, 90%, 95%, or 99% identical to SEQ ID NO:6. In some embodiments, the AA10 polypeptide comprises the amino acid sequence of SEQ ID NO:6. In some embodiments, the AA10 polypeptide comprises one or more of the identical amino residues depicted in FIG. 8. In some embodiments, the AA10 polypeptide comprises one or more of the identical amino residues depicted in FIG. 8, which are in stretches of ten or more consecutive identical amino acid residues. In some embodiments, the AA10 polypeptide comprises residues 1 to 241 of SEQ ID NO:6, or residues 1 to 241 of SEQ ID NO:11.

In some embodiments, the AA10 polypeptide comprising an amino acid sequence at least 70% identical to SEQ ID NO:6, or enzymatically active fragment thereof, wherein the amino acid sequence comprises one or more of the following amino acid sequences:

(SEQ ID NO: 66)
MNRRLIARLSGMLAMVLIAA, (SEQ ID NO: 67)
LAYVPKPEPAEAHGGMVFPATRTYACYVDGKVHGNGGDLNMINPACLDAL
AISGNYQFWNWFGNLISNAGGRHREIIPDGKLCGPTASFDGMNQARTDWW
TTRLQPGATITVRVNAWAPHPGTWYLYVTRDGWDPTQPLKWSDLEPTPFS
QVTNPPINSSGPDGAEYSWQVQLPNKQGRHIIYMIWQRSDSPEAFYNCS
D, (SEQ ID NO: 68)
YFGSGPIAYEFGDPREGGT.

The present invention provides a composition comprising the purified or isolated cellulase complex of the present invention and an ionic liquid (IL).

The present invention provides for a recombinant or isolated or purified nucleic acid encoding any of the GH polypeptides of a cellulase complex of the present invention. In some embodiments, the recombinant or isolated or purified nucleic acid encodes the GH9 polypeptide, the GH48 polypeptide, the GH10 polypeptide, and the GH6 polypeptide of the cellulase complex of the present invention. In some embodiments, the recombinant or isolated or purified nucleic acid further encoding one or more promoters operatively linked to the nucleotide sequences encoding GH9 polypeptide, the GH48 polypeptide, the GH10 polypeptide, and/or the GH6 polypeptide.

The present invention provides for a vector comprising the recombinant or isolated or purified nucleic acid of the present invention. In some embodiments, the vector is an expression vector. In some embodiments, the vector is a plasmid.

The present invention provides for a host cell comprising a nucleic acid of the present invention, wherein the host cell is capable of expressing the GH polypeptides of the present invention. In some embodiments, the nucleic acid is stably integrated into a chromosome of the host cell, or the nucleic acid is capable of stable residence in the host cell.

The present invention provides for a method for producing a cellulase complex of the present invention comprising: providing a host cell capable of expressing the cellulase complex, culturing the host cell in a culture medium under conditions whereby the cellulase complex is produced, optionally isolating the cellulase complex from the host cell and/or the culture medium, and optionally contacting the cellulase complex and a cellulose, whereby the cellulose is hydrolyzed by the cellulase complex.

In some embodiments, the providing step comprises: introducing an expression vector capable of expressing the cellulase complex in the host cell into the host cell, and optionally constructing the expression vector encoding a promoter operatively linked to a nucleic acid encoding the cellulase complex, wherein the constructing step precedes the introducing step.

In some embodiments, the composition further comprises an ionic liquid (IL). In some embodiments, the composition further comprises a cellulose, wherein the cellulase complex is capable of hydrolyzing the cellulose. In some embodiments, the composition further comprises an IL and a cellulose, wherein the cellulase complex is capable of hydrolyzing the cellulose. In some embodiments of the invention, the composition comprises a pretreatment biomass.

The present invention provides for a method of hydrolyzing a cellulose, comprising: (a) providing a solution comprising an IL, a cellulose, and a composition of the present invention to the solution, and (b) incubating the solution, such that the cellulose is hydrolyzed by the cellulase complex. In some embodiments of the invention, the solution comprises a pretreatment biomass.

The present invention provides for a method for converting of the carbohydrates of lignocellulose to sugars with improvements in yield and rate of sugar production has been developed by using the cellulase complex of the invention. In some embodiments of the invention, the cellulase complex is compatible with ionic liquid (IL). In some embodiments, the cellulase complex is introduced to a pretreatment biomass comprising a pretreatment cellulose biomass, pretreatment hemicellulose biomass, pretreatment lingo-cellulose biomass, or a mixture thereof.

The present invention provides for a method for converting a lignocellulosic biomass to sugars for the production of biofuels using the cellulase complex.

BRIEF DESCRIPTION OF THE DRAWINGS

The foregoing aspects and others will be readily appreciated by the skilled artisan from the following description of illustrative embodiments when read in conjunction with the accompanying drawings.

FIG. 5 shows a comparison of the amino acid sequence of the GH9 domain (residues 58 to 418) of SEQ ID NO:1, and the GH9 domain of *Paenibacillus* sp. A59 (WP_053783505) (SEQ ID NO:8).

FIG. 6 shows a comparison of the amino acid sequence of GH48 (SEQ ID NO:2) and the amino acid sequence of *Paenibacillus borealis* GH48 (SEQ ID NO:9).

FIG. 7 shows a comparison of the amino acid sequence of GH10_2 domain (SEQ ID NO:5) and the amino acid sequence of *Cohnella laeviribosi* GH10 (SEQ ID NO:10).

FIG. 8 shows a comparison of the amino acid sequence of the AA10 domain (residues 1 to 241) of SEQ ID NO:6, and the AA10 domain of *Caldibacillus cellulovorans* beta-1,4-mannanase precursor (SEQ ID NO:11).

DETAILED DESCRIPTION OF THE INVENTION

Figure 1:
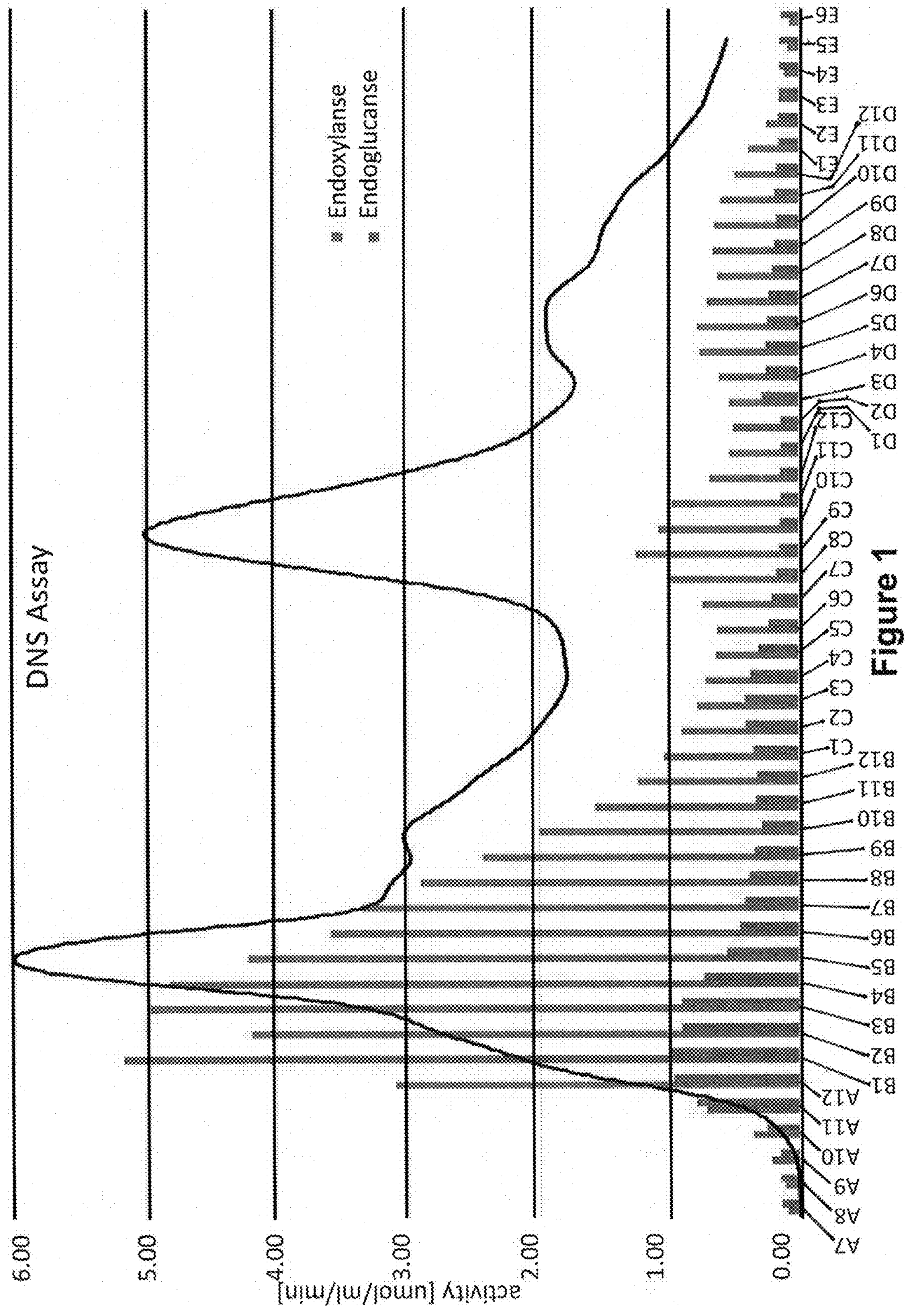
FIG. 1 shows the measurement of endoglucanase and endoxylanase activity of fractions from anion-exchange chromatography of 300 L supernatant

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

As used in the specification and the appended claims, the singular forms "a," "an," and "the" include plural referents unless the context clearly dictates otherwise. Thus, for example, reference to an "IL" includes a single IL compound as well as a plurality of IL compounds, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "host cell" refers to a living biological cell that can be transformed via insertion of an expression vector. Thus, a host cell as described herein may be a prokaryotic organism (e.g., an organism of the kingdom Eubacteria) or a eukaryotic cell.

The term "isolated" refers to material that is substantially or essentially free of components that normally accompany it in its native state.

As used herein, the terms "nucleic acid", "nucleotide" and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host cell. Only when the sequence of nucleic acids becomes stably replicated by the host cell does the host cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other host cells, wherein the progeny expression vectors possess the same ability to reproduce.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (3rd ed., Cold Spring Harbor Laboratory Press, Cold Spring Harbor, N.Y. (2001)), which is incorporated herein by reference. The nomenclatures utilized in connection with, and the laboratory procedures and techniques described herein are those well known and commonly used in the art.

The term "isolated nucleic acid" as used herein shall mean a polynucleotide that has been isolated from its naturally occurring environment. Such polynucleotides may be genomic, cDNA, or synthetic. Isolated polynucleotides preferably are not associated with all or a portion of the polynucleotides they associate with in nature. The isolated polynucleotides may be operably linked to another polynucleotide that it is not linked to in nature.

The term "isolated protein" referred to herein means a protein that has been isolated from its naturally occurring environment. Such proteins may be derived from genomic DNA, cDNA, recombinant DNA, recombinant RNA, or synthetic origin or some combination thereof, which by virtue of its origin, or source of derivation, the "isolated protein" (1) is not associated with proteins found in nature, (2) is free of other proteins from the same source, (3) is expressed by a cell from a different species, or (4) does not occur in nature.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

These and other objects, advantages, and features of the invention will become apparent to those persons skilled in the art upon reading the details of the invention as more fully described below.

The development of the JTherm cellulase enzymatic mixture, which is a cocktail containing supernatant from a thermophilic bacterial consortium maintained with microcrystalline cellulose as its sole carbon substrate as the identified endoglucanase component and cellobiohydrolase and beta-glucosidase components form heterologous proteins expressed in *E. coli* (PLoS One, 7:e37010, 2012; Green Chemistry, 15:2579-2589, 2013). The active component of JTherm was identified as an "endoglucanase". Biochemical techniques are sued to enrich the active fraction of JTherm and demonstrate that it contained a protein complex with multiple hydrolases (GH9, GH48, GH6, and GH10) and that this protein complex is capable of hydrolyzing IL pretreated biomass to glucose by addition of a beta-glucosidase, without supplement of the cellobiohydrolase. Metagenomic data show the glycoside hydrolases in the complex map to a low abundance Firmicutes present in the microbial community from which JTherm was derived. BLAST search of the sequence for xylanase (GH10) indicate that it is 98% identical at the amino acid level to xylanase isolated from "*Caldibacillus cellulovorans*" an unvalidated bacterial isolate (Microbiology, 146:2947-2955, 2000). No characterization of a glycoside hydrolase complex has been reported for "*Caldibacillus cellulovorans*".

Four full-length genes are identified using a PCR-based approach in a putative operon that constitutes the complex (FIG. 1). The amino acid sequences of the polypeptides encoded by the genes and the nucleotide sequence of the operon are described herein.

The amino acid sequence of the GH9 polypeptide of the cellulase complex is as follows:

(SEQ ID NO: 1)

MLRRRALSMLTGAAVVYSAFVPVGSPDSAVVRAAPTSYNYAEALQKAIYF

YDAQRSGKLPPDNRVEWRGDSGLNDGADVGVDLTGGWYDAGDHVKFGLPM

AYSAAMLAWAVYEYRDAFVQTGQLDYILNNIKWATDYFIKAHSAPNVLWG

QVGKGDVDHAWWGPAEVMQMPRPAYKIDPSCPGSDLAAGTAAAMAAAAAV

FKPTDPTYASTLIAHAKQLYTFADTYRGKYSDCITDAQNFYRSWSGYADE

LTWGAVWLYLATGEQAYLDKAIASVAEWGREGQTPYWGYKWTQSWDDVHY

GAQLLLARITGDQRFIQSTERNLEYWTDGTDDTGERITYTPGGLAWLDSW

GSLRYAMNASFLAFVYSDWLQSRDPAKAEKYRNFAVRQVLYALGDNPRNS

SYVVGFGRNPPQRPHHRTAHGSWADSQNVPAYHRHILYGALVGGPNQSDA

YTDSISDYVGNEVATDYNAAFTGNLAKMYLLFGASAGQRPLANFPEPEVR

EDEFFVEAGVNSSGPNYTEIKALINNRSGWPARMGDKLSFKYFVDLSEVY

AAGYTVNDIKVTTNYNEGAKVSGLLPYDESRRLYYVLVDFTGTKIYPGGQ

SAYKKEVQFRLSAPSGTSFWNPNNDFSYQLMSGTSNSSLVKTPYMPVYDA

GVKIFGVEPSSGSGSSPTPPPTSTPTPTPTPTPTPTLTLTPTPTPTPTPT

PTPTPTPTPTPTPTPTPTPTPTPTPTPTPTPTPTPTPTPSASGTLRVEYR

VGDTSATDNQMKPYLRIVNTGSQAVPLTELKVRYWYTKNSTQAEQYFCDW

AQIDCSNIRAQFVSLAQPVSGADSYIELSFTGGSVPAGGNTGEIQNRIHF

TNWMNYNETDDWSYNGTQTTWGPSTRITLYRNGVLVWGTEPGGGSSTPTP

TATPTPTPSAAPTPTPTAGGSLVVQYRAADTNAGDNQLKPHFRIVNRGTT

SVPLSELSIRYWYTVDGDKPQVFNCDWAQVGCSNLRGSFVKLSTGRTGAD

YYIEITFTSGAGSLAAGGSSGDIQVRINKNDWTNYNEANDYSYDPTKTSF

ADWNRVTLYRNGQLIWGVEP*

The amino acid sequence of the GH48 polypeptide of the cellulase complex is as follows:

(SEQ ID NO: 2)

MESLAWTLLWKKARIIFLAFALVVSAFAGFAVSPRSETAYAQTDPQVFKD

RFLQLYNQIKNPANGYFSPEGIPYHSIETLISEAPDYGHMTTSEAFSYWL

WLETLYGYFTGDWSKLEQAWTKMEQFIIPNSTEQPTMGSYNPSSPATYAP

EHPYPDRYPTLLNNSVPAGQDPLDAELKATYGNNVTYLMHWLLDVDNWYG

FGNLLNPSHTATYVNTFQRGEQESVWEAITHPSQDNFRFGKPNEGFVTLF

VKDNGTPAQQWRYTAASDADARAIQVMYWAKQLGYNNQTYLDKARKMGDY

LRYTLFDKYFQQIGSANDGSPSPGSGKNSAHYLLSWYTAWGGGLGSGGNW

AWRIGSSHAHQGYQNPVAAYALSAGGLAPRSATAQTDWATSLQRQLEFYT

WLQSSEGAIGGGATNSVGGSYQPYPSGRSTFYGMVYDEAPVYRDPPSNSW

FGFQAWSVERVAELYYIWTSSGNTNTQQFQMVKNIVTKWVDWALDYTFVN

QRPVTDAQGYFLTSSGSRVLGGNNPQIATVSDPGQFYIPSTLEWQGQPDT

WNGYANYTGNPNFHAIAKDPGQDVGVTGNYIKLLTFFAAATKAETGNYTA

LGSQALNVAEQLLNVLWNFNDGVGIVRPEQRADYFRYFTKEIYFPSGWSG

-continued

TYGQGNTIPGPGAVPSDPSKGGNGVYISYAELRPKIKQDPKWSYLENLYK

TSYNPSTGRWENGVPTFTYHRFWAQVDVATAYAEFARLIGGLGASPTPTP

SATPTPTPSAGGNLVVQYRAADTNATDNQLKPHFRIVNRGTTSVPLSELT

IRYWYTVDGDKPQVFNCDWAQVGCSNVRGSFVKLTTGRTGADYYIEITFT

SGAGSLAAGGSSGDIQVRINKNDWTNYNEANDYSCDPTKTSFADWNRVTL

YRNGQLVWGVEP*

The amino acid sequence of the GH10 polypeptide of the cellulase complex is as follows:

(SEQ ID NO: 3)

MLLVLAIGLLLPIPYLHVASAENVLILQSDFEDGTTQGWVGRGGVETLTV

TSAAAYSGAYGLSVSGRTKTWHGPTLDITSYIQVGKTYQFSAWVKLPSGS

SNTRIYMTMQRTMQDTVYYEQIYFDTASAGNWVQLKAQYKLYEPAVNLQV

YFEAPDHATQSFYIDDVRIEQLPDLPKTVEENIPSLKDVFAGRFPIGTAF

ENFELLDEQDRKLILKHFNSVTPGNVLKWDSTEPQEGVFNFTESDKAVAF

AVQNGMKIRGHTLIWHNQTPNWVFYDSNGNLVSKEVLYQRMERHIKPVVS

RYKGIIYAWDVVNEVIDPGQPDGLRRSLWYQIAGEEYIEKAFQFAHEADP

NALLFINDYNTHESGKSQALYNLVQRLKNKGIPVHGVGHQTHINISWPSI

SEIENSLVKFSNLGVVQEITELDMSIYNNSSQKYDTLPSDLAQQQATRYR

QLFEMFLRRSSLIQNVTFWGKDDANTWLRKFPVVRNDWPLLFDEQLKAKP

AYWAVVGTVPSPTPTPTSTATPTPTPTVIPTPTPTPTPTSTPTPTPTSTP

TPSASGTLRVEYRVGDSSATDNQMKPQLRIVNTGSQAVPLTELKVRYWYT

KNSTQAEQYFCDWAQIGCSNIRAQFVSLAQPVSGADSYIELSFTGGSVPA

GGNTGEIQNRIHFTNWMNYNETDDWSYNGTQTTWGPSTRITLYRNGVLVW

GTEPGGGSPTPTPTPTSTPTPTSTPTPTPTPTPTPTATPTPTPTPTPSAG

GNLVVQYRAADTNAGDNQLKPHFRIVNRGTTSVPLSELTIRYWYTVDGDK

PQVFNCDWAWVGCSNLRGSLVKLTTGRTGADYYLEITFTSGAGSLAPGAN

SGDIQARINKNDWTNYNEANDYSYDPTKTSFADWNRVTLYRNGQLVWGVE

P*

The amino acid sequence of the GH6 polypeptide of the cellulase complex is as follows:

(SEQ ID NO: 4)

MTMAWKQRSGLIALILALVAGLLLPWGSLPKAAAEPHVDNPFVGATAYVN

PDYAALVDSSIARVSDPTLAAKMRTVKTYPTAVWLDRIAAIDGGPGRRSL

VQHLDTALAQKQGNTPITAMFVIYNMPGRDCAALASNGELPLTQEGLQRY

KTEYIDRIAAIFADPKYAGIRIVTVIEPDGLPNLVTNLSDPECAQANSSG

IYVEAVRYAINKLSEIPNVYIYLDIAHSGWLGWDNNRTGAVQLYTNVVRG

TTKGLSSVDGFVTNVANYTPLEEPYLTDPNLTVGGQPLKSAKFYEWNPYF

DEVDYAAALRSAFISAGWPTSIGMLIDTSRNGWGGPNRPTGASGTTVDAY

VNSGRVDRRAHRGLWCNVSGAGMGMPPQVAPAAYASQGIEAFVWVKPPGE

SDGASSEIPNDEGKRFDRMCDPTYTTQYGVLTGALPNAPLAGQWFHDQFV

MLVQNAYPAIPTSGGGTPTPTPSTTVTPTPTPTPTPTPSATVTPTPTPTPTP

-continued

TPSATVTPTPTPTPTPTPTVTPTPTSSTSFVARHGQLRVVGNQLVDQNGQ

PIQLRGISSHGLQWYGHFVNRDSLRWLRDDWGITVFRAALYTAEQGYITN

PSLKEKVKEAVQAAIELGIYVIIDWHILSDGDPNTYKEQAKAFFDEMSRL

YGSYPNVIYEIANEPNGVTWEGQVKPYASEVIPVIRANDPDNLIIVGTTT

WSQDVHLAADSPLPYSNLAYALHFYAGTHGQWLRDRIDYARNKGIAIFVS

EWGTSTSTGDGGPYLTESQQWLDFLNARQISWVNWSLSDKAESSAALLPG

ASATGGWTDAQLSQSGRFVRAQIRSGVLTPTPTPTPTPTPSAAPTPTPTA

GGSLVVQYRAADTNAGDNQLKPHFRIVNRGTTSVPLSELSIRYWYTVDGD

KPQVFNCDWAQVGCSNLRGSFVKLSTGRTGADYYIEITFTSGAGSLAAGG

SSGDIQVRINKNDWTNYNEANDYSYDPTKTSFADWNRVTLYRNGQLIWGV

EP*

The amino acid sequence of the GH10_2 polypeptide of the cellulase complex is as follows:

(SEQ ID NO: 5)

MHQIAERRKMIMRNWLQWGMVAALLVFTVSVVPPKEADAGLAKTKFLGNV

INNSIPSDFAVYWNQVTPENATKWGSVESSRDNMNWSTADMIYNYARSNG

FPFKFHTLVWGSQEPGWISGLSAAEQQAEVIEWIQAAGQRYPDADFVDVV

NEPLHAKPSYRNAIGGDGSTGWDWVIWSFEQARRAFPNSKLLINEYGVEN

DPNAASQYVQIINLLKSRGLIDGIGIQGHYFNLDTVSVSTLRTTLGMLAE

TGLPIYVSELDISGDDATQLARYQEKFPILWEHPSVQGITLWGYIEGQTW

RSGTHLITASGVERPALQWLRTYLAGAGSSPTPTPTPTPTVTPTVTPTPT

PSANGTLRVEYRVGDSSATDNQMKPQLRIVNTGSQAVPLTELKVRYWYTK

NSTQAEQYFCDWAQIGCSNIRAQFVSLSQPVSGADSYIELSFTGGSIPAG

-continued

GNTGEIQNRIHFTNWMNYNETDDWSYNGAQTTWGPSTRITLYRNGVLVWG

TEPGGSSTPTPTPTPTPTPTPSAAPTPAPSAGGSLVVQYRAADTNATDNQ

LKPHFRIVNRGTTSVPLSELTIRYWYTVDGDKPQVFNCDWAQVGCSNVRG

SFVKLSTGRTGADYYIEITFTSGAGSLAPGANSGDIQARINKNDWTNYNE

ANDYSYDPTKTSFADWNRVTLYRNGQLIWGVEP*

The amino acid sequence of the AA10 polypeptide of the cellulase complex is as follows:

(SEQ ID NO: 6)

MNRRLIARLSGMLAMVLIAAVLAYVPKPEPAEAHGGMVFPATRTYACYVD

GKVHGNGGDLNMINPACLDALAISGNYQFWNWFGNLISNAGGRHREIIPD

GKLCGPTASFDGMNQARTDWWTTRLQPGATITVRVNAWAPHPGTWYLYVT

RDGWDPTQPLKWSDLEPTPFSQVTNPPINSSGPDGAEYSWQVQLPNKQGR

HIIYMIWQRSDSPEAFYNCSDAYFGSGPIAYEFGDPREGGTMITPPPSGT

TPTPTPTPTPTPTPTLTPTPTPTPTPTPTLTPTPTPTPTPTSTPTSTP

TSTPTPTPTPSASGTLRVEYRVGDSSATDNQMKPQLRIVNTGSQAVPLTE

LKMRYWYTKNSTQAEQYFCDWAQIGCSNIRAQFVSLSQPVSGADSYIELS

FTGGSIPAGGNTGEIQNRIHFTNWMNYNETDDWSYNGAQMTWGPSTRITL

YRNGVLVWGTEPGGGSSPPTPTPTVTPTPTPTSTPTPTPTPSAAPTPTPSAG

GSLVVQYRAADTNAGDNQLKPHFRIVNRGTTSVPLSELSIRYWYTVDGDK

PQVFNCDWAQVGCSNLRGSFVKLSTGRTGADYYIEITFTSGAGSLAPGAS

SGDIQVRINKNDWTNYNEANDYSYDPTKTSFADWNRVTLYRNGQLVWGVE

P*

A nucleotide sequence encoding an operon encoding GH9, GH48, GH10, GH6, AA10, and GH10_2 is as follows:

(SEQ ID NO: 7)

TTGAAGGAGGAACAGACGGTGAATTTCCGACAACTGATGCTGAGACGACGGGCGCTGTCG

ATGTTGACGGGCGCGGCGGTCGTTTATTCGGCTTTCGTGCCGGTTGGAAGTCCGGATTCG

GCTGTTGTTCGGGCGGCTCCTACCTCTTACAATTACGCGGAAGCGCTTCAAAAGGCAATT

TATTTCTACGACGCACAACGTTCCGGCAAGCTGCCTCCCGATAACCGCGTCGAATGGCGC

GGCGATTCCGGGCTTAACGACGGAGCCGACGTCGGCGTCGATTTGACGGGCGGTTGGTAC

GACGCCGGCGACCACGTCAAGTTCGGGTTGCCGATGGCATATTCCGCCGCCATGCTGGCG

TGGGCGGTGTACGAGTACCGCGACGCTTTCGTGCAGACGGGGCAGCTCGATTATATTTTG

AACAACATCAAGTGGGCGACCGACTATTTCATCAAGGCGCATTCCGCGCCCAACGTGCTT

TGGGGACAGGTCGGCAAGGGGGACGTCGATCATGCCTGGTGGGGACCGGCAGAAGTGATG

CAGATGCCGCGTCCGGCCTACAAAATCGACCCGAGCTGTCCGGGGTCCGATCTCGCTGCC

GGAACGGCCGCCGCGATGGCCGCCGCCGCCGCGGTGTTTAAACCCACTGACCCGACTTAT

GCCTCAACGTTGATCGCTCATGCGAAACAATTGTATACGTTTGCAGATACTTATCGGGGG

AAATATTCCGATTGCATCACTGATGCGCAAAATTTCTATCGGTCGTGGAGCGGTTACGCC

GATGAGCTGACGTGGGGTGCCGTCTGGCTTTATCTCGCCACCGGCGAGCAGGCCTATCTT

GACAAGGCAATCGCCTCAGTCGCGGAATGGGGGCGCGAAGGTCAGACGCCTTATTGGGGT

TACAAATGGACGCAAAGCTGGGACGACGTCCATTACGGCGCTCAGCTGCTGTTGGCAAGA

-continued

ATTACGGGCGACCAGCGGTTTATCCAGTCGACGGAGCGCAACCTGGAATATTGGACGGAC

GGCACGGACGACACCGGCGAGCGCATCACGTATACGCCCGGGGGGCTTGCTTGGCTAGAT

TCTTGGGGTTCACTCCGCTATGCGATGAACGCGTCGTTCTTGGCGTTCGTCTATTCCGAC

TGGCTGCAAAGCCGCGATCCCGCCAAAGCGGAAAAGTACAGGAACTTCGCCGTTCGCCAG

GTTCTGTATGCATTGGGCGACAACCCGCGCAATTCTAGCTATGTCGTCGGATTCGGGCGC

AATCCGCCGCAGCGGCCGCATCACCGGACGGCGCACGGGTCGTGGGCTGACAGCCAGAAC

GTTCCCGCTTACCATCGGCACATTTTATATGGCGCTCTTGTGGGCGGTCCGAACCAGTCC

GACGCCTATACGGATTCGATCAGCGACTACGTCGGCAATGAGGTTGCGACGGATTACAAC

GCGGCGTTTACGGGAAATCTCGCAAAAATGTATCTGCTGTTCGGCGCCAGCGCCGGACAG

CGGCCGCTTGCCAATTTTCCCGAGCCGGAAGTACGCGAGGACGAGTTTTTCGTCGAAGCC

GGCGTGAACAGCTCCGGACCGAACTACACAGAGATCAAGGCCCTGATCAACAACCGGTCC

GGCTGGCCCGCGCGGATGGGCGACAAGCTTTCGTTCAAGTATTTCGTCGATTTGTCTGAA

GTTTACGCCGCCGGTTATACGGTCAACGACATTAAGGTGACGACGAACTACAACGAAGGC

GCGAAAGTATCCGGTCTGCTTCCGTATGACGAAAGCCGTCGTCTTTACTATGTGCTCGTC

GATTTTACGGGTACGAAGATTTATCCCGGCGGTCAGTCCGCCTACAAGAAAGAGGTTCAG

TTCAGACTGAGCGCTCCGAGCGGGACATCGTTCTGGAATCCGAACAACGATTTCTCGTAC

CAGCTGATGTCCGGCACGTCCAACAGCAGCCTGGTCAAGACGCCGTATATGCCGGTTTAT

GACGCCGGGGTGAAGATTTTCGGCGTGGAGCCGTCGTCCGGAAGCGGGTCGAGCCCGACG

CCGCCACCCACGTCGACGCCGACACCGACACCGACGCCGACACCGACACCGACGCTGACA

CTGACACCGACACCGACGCCGACACCGACGCCGACACCGACGCCGACACCGACGCCGACA

CCGACACCGACGCCGACACCAACGCCGACACCAACGCCGACACCGACGCCGACGCCGACA

CCAACGCCGACGCCGACACCGACACCGACGCCTAGCGCGAGCGGTACCCTGCGCGTCGAG

TATCGCGTCGGTGACACCAGCGCCACCGACAACCAGATGAAGCCGTACCTGCGCATCGTC

AACACCGGCTCGCAAGCCGTGCCGCTGACCGAACTGAAGGTGCGCTACTGGTACACGAAG

AACTCGACGCAGGCCGAACAGTACTTCTGCGACTGGGCGCAGATCGACTGCTCGAACATC

CGGGCGCAGTTCGTGTCGCTGGCGCAGCCGGTCAGTGGAGCGGACAGCTACATCGAGCTG

AGCTTCACGGGCGGAAGCGTTCCGGCGGGAGGCAACACGGGCGAGATACAGAACCGGATT

CACTTCACGAACTGGATGAACTACAACGAAACGGACGACTGGTCGTACAACGGGACGCAG

ACGACGTGGGGTCCGTCGACGCGGATTACGCTGTATCGTAACGGCGTGCTGGTGTGGGGC

ACCGAGCCGGGCGGCGGATCGTCGACGCCGACACCGACGGCGACACCTACGCCTACGCCG

AGCGCGGCGCCCACACCGACGCCGACGGCCGGCGGCAGCCTGGTCGTGCAGTATCGCGCG

GCGGACACGAACGCGGGCGACAACCAGCTGAAGCCGCACTTTAGGATTGTGAACCGCGGG

ACGACGAGCGTGCCGCTGTCGGAGCTTTCGATCCGGTACTGGTACACGGTGGACGGGGAC

AAGCCGCAGGTGTTCAACTGCGACTGGGCGCAGGTGGGTTGTTCGAACTTGCGGGGCAGT

TTCGTGAAGCTTTCGACGGGCCGGACGGGGGCGGACTACTACATCGAGATCACGTTCACA

TCGGGCGCGGGCAGCTTGGCGGCTGGGGGAAGCAGTGGGGACATTCAGGTGCGGATCAAC

AAGAACGACTGGACGAACTACAACGAGGCGAACGATTACTCGTATGATCCGACGAAGACG

AGTTTTGCGGATTGGAACCGGGTGACGCTGTATCGCAACGGTCAGCTCATCTGGGGCGTC

GAACCATAGCAAAATTCGGTGGTTTATTCTTTTGAACAGCAAACCCCAGGGAACGGAGGA

ATGAGGGTGTCGATCGAATTGGCAATCCTATTGCCGACCTTCGTTCCCTGGTTTGCAAAT

-continued

AGAAACGCTACAAAAAACAGGAGGAAGAGGGAAAATCATGGAATCACTCGCATGGACGCT

GTTATGGAAGAAAGCAAGAATTATCTTTCTTGCTTTCGCGCTTGTCGTCTCCGCCTTCGC

GGGCTTCGCTGTGTCTCCTCGTAGCGAAACCGCTTACGCGCAGACGGACCCGCAGGTTTT

CAAGGACAGGTTTTTGCAGCTGTACAACCAAATCAAAAATCCGGCGAACGGTTACTTTTC

GCCGGAAGGCATTCCTTATCACTCCATCGAAACGTTGATTTCGGAAGCTCCCGACTATGG

GCATATGACGACGTCGGAAGCGTTCAGTTATTGGCTCTGGCTGGAAACGCTATATGGTTA

CTTCACCGGTGACTGGTCGAAACTGGAACAGGCTTGGACAAAAATGGAGCAATTCATTAT

CCCGAACTCGACGGAACAGCCGACGATGGGGTCTTACAACCCATCAAGTCCAGCTACTTA

CGCGCCGGAACATCCGTATCCGGACCGGTATCCAACTTTGCTGAACAATTCCGTGCCGGC

AGGACAGGACCCACTGGATGCGGAACTCAAAGCGACGTACGGTAATAACGTGACGTATTT

GATGCACTGGCTGCTTGACGTGGACAATTGGTACGGCTTCGGCAACCTGTTGAACCCGTC

GCATACGGCGACCTACGTCAACACGTTCCAGCGCGGCGAACAGGAATCGGTCTGGGAGGC

GATCACACATCCGTCGCAGGACAATTTCCGGTTCGGAAAACCGAATGAAGGTTTTGTGAC

GCTGTTCGTAAAAGATAACGGAACGCCTGCCCAGCAATGGCGTTATACGGCAGCCTCTGA

CGCCGACGCACGCGCCATTCAGGTGATGTATTGGGCGAAGCAGCTGGGGTACAACAACCA

GACCTATCTGGATAAGGCGCGCAAGATGGGCGACTATCTGCGCTATACACTGTTCGACAA

GTATTTCCAACAAATCGGCAGTGCAAACGACGGTTCTCCGAGCCCGGGCAGCGGTAAAAA

CTCTGCGCATTACCTTTTGTCTTGGTACACGGCCTGGGGCGGTGGTCTCGGCTCCGGCGG

CAACTGGGCTTGGAGAATCGGATCGAGCCATGCTCATCAGGGTTATCAAAATCCTGTCGC

TGCTTATGCGCTGTCTGCCGGCGGACTGGCGCCGCGTTCCGCAACGGCACAGACCGACTG

GGCGACGTCGTTGCAACGTCAGCTTGAATTCTATACGTGGCTGCAATCGAGCGAAGGCGC

CATCGGCGGCGGGGCGACCAACAGCGTCGGGGGCAGCTATCAGCCGTATCCTTCCGGTCG

CAGTACGTTCTACGGCATGGTTTACGATGAAGCGCCGGTTTATCGCGATCCGCCTTCGAA

CTCGTGGTTCGGCTTCCAAGCGTGGTCCGTCGAACGCGTCGCGGAACTGTACTATATCTG

GACCAGCAGCGGAAATACCAATACGCAGCAGTTCCAGATGGTTAAAAACATCGTCACCAA

ATGGGTCGATTGGGCGCTTGACTATACGTTCGTGAATCAACGCCCGGTTACAGACGCTCA

AGGGTATTTCCTGACGAGCAGCGGCAGCCGTGTCCTGGGCGGCAACAATCCGCAGATCGC

CACGGTTTCCGATCCCGGTCAGTTCTATATTCCGTCGACGCTGGAATGGCAGGGTCAACC

GGACACATGGAACGGATATGCCAATTATACGGGCAATCCCAATTTCCATGCGATTGCGAA

AGACCCCGGCCAAGACGTCGGCGTCACCGGCAACTATATCAAGCTGCTGACGTTCTTTGC

CGCGGCCACGAAAGCGGAGACGGGGAACTACACCGCTCTCGGAAGCCAGGCGTTGAATGT

CGCCGAACAGTTGCTGAACGTGCTTTGGAATTTCAACGACGGGGTTGGGATTGTCCGTCC

CGAACAACGCGCCGACTACTTCCGCTATTTTACGAAGGAAATTTACTTCCCGAGCGGCTG

GAGCGGCACGTACGGACAGGGCAATACCATTCCTGGGCCGGGCGCGGTTCCTTCCGATCC

GTCGAAAGGCGGAAACGGCGTTTATATCAGCTACGCCGAACTGCGTCCGAAGATCAAGCA

AGATCCGAAATGGTCGTATCTTGAAAATCTGTACAAAACTTCGTATAATCCGTCCACAGG

TCGCTGGGAAAACGGTGTTCCGACGTTCACGTATCACCGTTTCTGGGCGCAGGTCGATGT

GGCGACGGCGTATGCGGAATTTGCCCGGTTGATCGGCGGTTTGGGCGCTTCGCCGACACC

GACGCCGAGCGCGACACCGACGCCGACACCGTCGGCCGGCGGCAACCTGGTCGTGCAGTA

CCGCGCGGCGGACACGAACGCGACGGACAACCAGCTGAAGCCGCACTTTAGGATTGTGAA

CCGCGGGACGACGAGCGTGCCGTTGTCGGAGCTGACGATCCGGTACTGGTACACGGTGGA

-continued

CGGAGACAAGCCGCAGGTGTTCAACTGCGACTGGGCGCAGGTAGGTTGCTCGAATGTGCG

TGGCAGCTTTGTGAAGCTGACGACGGGCCGGACGGGGGCGGACTACTACATCGAGATCAC

GTTCACGTCGGGCGCGGGCAGCTTGGCGGCTGGGGGAAGCAGTGGGGACATTCAGGTGCG

GATCAACAAGAACGACTGGACGAACTACAACGAGGCGAACGACTACTCGTGTGATCCGAC

GAAGACGAGTTTTGCGGATTGGAACCGAGTGACGCTGTATCGTAACGGTCAGCTCGTCTG

GGGCGTCGAACCGTAACGCACAACAGTCCATGCCGAGAAGGTTCGGGGGCGTTCAACTGA

AGACGGGGAACGCCCCCGTTCCTGAAAGTATGTCACGAGCAAAACGAGGGAGGAGCCGAG

CATGGGAACGGGCCGTGCCGGAGAGTGGATCAAAAAAATGTTGCTGGTTTTGGCAATTGG

ATTGCTCCTTCCGATTCCATACCTGCATGTCGCTTCAGCGGAAAACGTCCTGATTTTGCA

GAGCGATTTTGAGGACGGGACGACGCAAGGGTGGGTCGGTCGCGGGGGAGTCGAAACGCT

TACTGTCACTTCCGCGGCAGCGTACAGCGGAGCTTATGGTTTGTCCGTGAGCGGAAGAAC

GAAAACGTGGCATGGTCCGACATTGGACATCACTTCCTATATTCAGGTTGGAAAGACTTA

TCAATTTTCAGCATGGGTTAAATTGCCTTCCGGTTCGTCCAACACACGCATTTATATGAC

GATGCAAAGAACCATGCAGGACACGGTCTACTATGAGCAAATTTATTTCGACACGGCTTC

AGCTGGAAATTGGGTTCAATTGAAAGCCCAATACAAGTTGTACGAACCTGCTGTAAACCT

GCAGGTATACTTTGAAGCTCCCGATCATGCTACTCAATCTTTCTATATTGATGACGTCCG

AATTGAACAACTTCCTGATCTTCCGAAGACGGTAGAAGAGAATATTCCGTCCCTGAAAGA

TGTTTTCGCAGGGCGTTTTCCGATAGGAACGGCGTTTGAAAATTTTGAACTTCTCGATGA

ACAGGACAGAAAATTGATTTTAAAACATTTCAATAGTGTGACGCCTGGAAACGTGCTGAA

GTGGGACAGCACAGAACCACAAGAAGGAGTCTTTAACTTTACGGAATCGGATAAAGCGGT

TGCTTTTGCGGTTCAGAACGGAATGAAGATCAGAGGTCATACATTGATTTGGCATAATCA

GACGCCGAATTGGGTGTTTTATGATTCAAACGGAAATTTAGTTTCCAAAGAAGTTCTATA

TCAACGAATGGAAAGACACATTAAACCCGTCGTCAGCCGCTACAAAGGAATCATCTATGC

GTGGGATGTCGTCAATGAAGTTATCGATCCCGGACAGCCTGATGGATTGCGTAGAAGCTT

GTGGTATCAGATTGCCGGCGAGGAGTATATCGAAAAGGCGTTCCAATTTGCGCATGAAGC

TGATCCGAATGCGCTTCTCTTCATCAATGATTATAACACGCATGAATCCGGTAAAAGCCA

AGCATTGTACAATTTGGTACAACGACTGAAAAATAAGGGTATTCCTGTTCACGGAGTCGG

ACACCAGACCCATATTAATATTTCCTGGCCGTCGATCAGTGAAATCGAAAATTCGCTCGT

CAAGTTCTCGAACCTGGGAGTTGTTCAGGAAATCACTGAGTTGGATATGAGCATTTACAA

CAATTCATCACAGAAGTACGACACATTGCCTTCCGATTTGGCTCAGCAGCAGGCAACCCG

TTACAGACAACTGTTCGAAATGTTCTTGAGAAGGAGCAGTTTGATTCAAAACGTTACGTT

CTGGGGCAAAGATGATGCAAATACGTGGTTGCGGAAGTTCCCAGTCGTCCGAAATGACTG

GCCGCTGTTGTTCGATGAGCAATTAAAGGCGAAACCGGCATATTGGGCGGTAGTCGGAAC

TGTTCCGTCACCCACGCCGACACCGACGTCGACGGCAACACCAACGCCGACACCAACGGT

GATACCGACGCCGACACCGACGCCAACGCCGACATCGACGCCGACACCGACGCCGACGTC

GACGCCGACGCCTAGCGCGAGCGGCACCCTGCGCGTCGAGTATCGCGTGGGCGATTCCAG

CGCCACCGACAACCAGATGAAACCGCAGCTGCGCATCGTCAACACCGGCTCGCAAGCCGT

GCCGCTGACCGAACTGAAAGTGCGCTACTGGTACACGAAGAACTCGACGCAGGCCGAACA

GTACTTCTGCGACTGGGCGCAAATCGGCTGCTCGAACATCCGGGCGCAGTTCGTGTCGCT

GGCGCAGCCAGTCAGCGGAGCGGACAGCTACATCGAGCTGAGCTTCACGGGGGGCAGCGT

-continued

TCCGGCGGGAGGCAACACGGGCGAGATCCAGAACCGGATTCACTTCACGAACTGGATGAA

CTACAACGAAACGGACGACTGGTCGTACAACGGGACGCAGACGACGTGGGGGCCGTCGAC

GCGGATTACGCTGTATCGTAACGGCGTGCTGGTGTGGGGCACCGAGCCGGGCGGCGGATC

GCCGACACCGACACCAACGCCGACGTCAACGCCGACGCCGACGTCAACGCCGACACCGAC

GCCGACGCCGACACCGACACCGACGGCGACACCGACACCCACACCCACGCCGACGCCGTC

GGCCGGCGGCAACCTGGTCGTGCAGTACCGCGCGGCGGACACGAACGCGGGCGACAACCA

GCTGAAGCCGCATTTTCGGATTGTGAACCGCGGGACGACGAGCGTACCGTTGTCGGAGCT

TACGATTCGGTACTGGTACACGGTGGACGGCGACAAGCCGCAGGTGTTCAACTGTGACTG

GGCGTGGGTCGGATGTTCGAACCTGCGCGGCAGTCTGGTGAAGTTGACGACGGGCCGGAC

GGGGGCGGACTACTACCTTGAGATCACGTTCACATCGGGCGCGGGCAGCCTGGCGCCTGG

GGCGAACAGCGGAGACATTCAGGCGCGGATCAACAAGAACGACTGGACGAACTACAACGA

GGCGAACGACTACTCGTATGATCCGACGAAGACGAGTTTTGCGGATTGGAACCGGGTGAC

GCTGTATCGGAATGGTCAGCTCGTCTGGGGCGTCGAGCCGTAAGGGTATACCTAAGAGCG

GCGTGGCGGAGTCGATAAGCGGTGATGATTCCGCCTCGCTCGAGGACCGGTCGACTGCCA

CAGAAGGCTTTGTGAAGGAGGTGATGGACGGAAGATCCGAAAAAGAAAGAATATGAAGGT

TTTGTGGGTTGGTTTTGGTAAAAAAGAATCCATGAGGAACCAAACGAAAGAGGGGAGTGA

CACAGGCATGACGATGGCGTGGAAACAGCGCAGCGGATTGATCGCGTTGATTTTGGCATT

GGTAGCGGGTTTGCTGCTGCCATGGGGATCGCTGCCGAAAGCGGCGGCGGAGCCGCATGT

GGACAATCCGTTTGTAGGAGCGACGGCTTACGTCAATCCGGACTATGCGGCGCTGGTCGA

TTCGTCGATCGCGAGGGTGAGCGATCCAACGCTGGCGGCGAAGATGCGTACGGTCAAGAC

GTATCCGACGGCGGTGTGGTTGGATCGGATCGCGGCGATTGACGGAGGGCCGGGAAGACG

GAGCTTGGTGCAGCATTTGGATACGGCGTTGGCGCAGAAGCAAGGGAATACGCCGATTAC

GGCGATGTTTGTGATTTACAATATGCCGGGTCGGGACTGCGCGGCGCTGGCGTCGAACGG

GGAGCTGCCGCTGACGCAGGAAGGGCTGCAGAGGTACAAGACGGAGTATATTGACCGAAT

TGCGGCAATTTTTGCAGATCCGAAGTATGCGGGAATTCGGATCGTGACGGTGATTGAACC

GGACGGCTTGCCGAACCTGGTGACGAACCTGAGCGATCCGGAATGCGCGCAGGCGAATTC

AAGCGGAATTTATGTAGAGGCAGTACGATATGCGATCAACAAGTTGAGCGAAATTCCGAA

CGTGTATATTTACCTGGACATCGCGCATTCGGGATGGCTGGGCTGGGACAACAACCGGAC

CGGCGCGGTGCAGCTGTATACGAACGTGGTGCGAGGGACGACGAAAGGGCTTTCGAGCGT

GGACGGGTTTGTGACGAACGTGGCGAACTATACGCCGCTCGAGGAGCCGTATTTGACGGA

TCCAAACCTGACGGTGGGAGGTCAGCCGCTTAAGTCAGCGAAGTTTTATGAGTGGAACCC

GTATTTTGATGAAGTAGATTATGCGGCAGCGTTGCGGTCGGCGTTTATCAGTGCAGGGTG

GCCGACGAGCATCGGGATGTTGATCGACACGAGCCGCAACGGCTGGGGCGGGCCGAACCG

GCCGACGGGAGCGAGCGGGACGACGGTGGACGCGTATGTGAATTCGGGGCGTGTGGACCG

TCGGGCGCATCGCGGGCTGTGGTGTAACGTCAGCGGAGCGGGGATGGGAATGCCGCCGCA

GGTGGCGCCGGCGGCGTATGCGTCGCAAGGGATCGAGGCATTCGTATGGGTGAAGCCGCC

CGGGGAGTCGGACGGAGCGAGTTCGGAGATACCGAACGACGAAGGCAAGCGGTTTGACCG

GATGTGCGATCCGACGTATACGACGCAATACGGGGTGTTGACGGGGGCGTTGCCGAACGC

GCCGTTGGCGGGGCAATGGTTCCATGATCAGTTTGTGATGTTGGTGCAGAATGCGTATCC

GGCGATTCCGACGAGCGGCGGTGGGACACCGACGCCGAGTACGACGGTGACGCCGACACC

GACACCGACGCCGACACCGACGCCGAGTGCGACGGTGACGCCGACACCGACACCGACGCC

-continued

GACACCGACGCCGAGTGCGACGGTGACGCCGACACCGACACCGACGCCGACACCGACGCC

GACGGTGACGCCGACGCCGACATCGTCGACAAGTTTTGTGGCCAGGCACGGGCAATTGAG

AGTCGTGGGGAATCAATTGGTCGACCAAAATGGACAACCCATCCAACTAAGAGGCATTAG

TTCTCATGGGTTACAATGGTATGGGCATTTCGTCAATCGAGACAGCCTCCGATGGCTCCG

AGATGATTGGGGAATAACAGTTTTCCGAGCAGCTCTGTATACTGCCGAACAAGGATATAT

CACGAATCCGTCTTTAAAAGAAAAAGTGAAGGAAGCTGTACAAGCCGCAATTGAACTCGG

TATTTATGTGATCATCGACTGGCACATTTTGTCTGATGGCGATCCGAACACGTACAAGGA

GCAAGCGAAAGCGTTTTTCGATGAAATGTCGCGATTGTACGGCAGTTATCCGAACGTGAT

TTATGAGATCGCCAACGAACCGAATGGTGTGACATGGGAAGGACAGGTTAAGCCGTACGC

TTCGGAGGTGATCCCGGTCATCCGTGCTAATGACCCTGATAATCTCATTATTGTCGGAAC

AACAACGTGGAGTCAGGATGTCCATCTTGCAGCAGATAGCCCGCTACCTTACAGCAACCT

GGCGTACGCTCTGCATTTCTATGCCGGTACGCATGGTCAATGGTTGAGAGACCGGATCGA

CTATGCGAGGAATAAAGGCATCGCGATTTTCGTGAGTGAATGGGGGACAAGCACTTCGAC

AGGCGATGGAGGCCCCTATCTCACGGAGTCGCAACAATGGTTGGATTTCCTTAATGCTCG

GCAGATCAGTTGGGTGAACTGGTCGTTGAGCGACAAGGCCGAGTCATCCGCAGCATTGTT

GCCTGGCGCAAGCGCAACAGGTGGTTGGACGGACGCACAATTGTCTCAGTCGGGGCGTTT

TGTTCGCGCTCAGATTCGCAGCGGTGTATTGACGCCGACACCGACGCCGACACCTACGCC

TACGCCGAGTGCGGCGCCCACACCGACGCCGACGGCCGGCGGCAGCCTGGTCGTGCAGTA

TCGCGCGGCGGACACGAACGCGGGCGACAACCAGCTGAAGCCGCATTTTCGGATTGTGAA

CCGCGGGACGACGAGCGTGCCGCTGTCGGAGCTTTCGATCCGGTACTGGTACACGGTGGA

CGGAGACAAGCCGCAGGTGTTCAACTGCGACTGGGCGCAGGTGGGTTGTTCGAACTTGCG

GGGCAGTTTCGTGAAGCTTTCGACGGGCCGGACGGGGGCGGACTACTACATTGAGATCAC

GTTCACGTCGGGCGCGGGCAGCTTGGCGGCTGGGGGAAGCAGCGGGGACATTCAGGTGCG

GATCAACAAGAACGACTGGACGAACTACAATGAGGCGAACGACTACTCGTATGATCCGAC

GAAGACGAGTTTTGCGGATTGGAACCGGGTGACGCTGTATCGCAACGGTCAGCTCATCTG

GGGCGTCGAGCCTTGATTGCCAACCGACGGTATGGACCTGGCGGACGGTAAGTCCGTTCG

CCAGGTTCCTATAAAAACAACATCTCCGCTCGAAAAAACCTTGAAGGAAGGGAGAGGATT

TTTTATGAATCGACGCCTTATCGCCCGCCTCAGCGGCATGTTGGCGATGGTTCTCATCGC

CGCAGTGTTGGCGTACGTTCCGAAGCCTGAACCGGCCGAGGCGCACGGAGGTATGGTGTT

TCCAGCCACGCGAACGTATGCCTGTTATGTTGACGGCAAGGTTCACGGCAATGGCGGAGA

CTTGAACATGATCAATCCGGCGTGTCTTGATGCCTTGGCGATCTCGGGCAACTATCAGTT

CTGGAACTGGTTCGGAAATCTGATCAGTAATGCCGGAGGACGCCATAGGGAAATCATTCC

TGACGGCAAACTGTGCGGACCAACGGCCAGTTTTGATGGTATGAACCAGGCGCGTACAGA

CTGGTGGACGACTCGTCTGCAGCCGGGCGCAACGATTACGGTGCGAGTCAACGCATGGGC

GCCGCATCCCGGCACGTGGTATTTGTATGTAACCCGGGACGGATGGGATCCGACACAACC

GCTGAAATGGTCGGATCTGGAACCGACGCCCTTCAGCCAGGTGACTAATCCGCCGATCAA

CTCGAGCGGACCGGACGGGGCCGAGTACAGCTGGCAGGTGCAGCTGCCGAACAAGCAAGG

GCGACACATCATTTATATGATATGGCAGAGATCCGACAGTCCGGAGGCATTTTACAACTG

TTCGGATGCGTATTTCGGATCGGGGCCGATTGCTTATGAATTTGGTGACCCGCGGGAAGG

AGGAACGATGATTACGCCGCCGCCGTCGGGCACGACGCCGACACCGACGCCGACACCGAC

-continued

GCCGACACCGACGCCGACACTGACGCCGACACCGACGCCGACACCGACGCCGACACCGAC

GCCGACACTGACGCCGACACCGACGCCGACACCGACGCCGACATCGACGCCGACGTCGAC

ACCGACGTCGACGCCGACACCGACACCGACGCCTAGCGCGAGCGGCACCCTGCGTGTCGA

GTATCGCGTGGGCGATTCCAGCGCCACCGACAACCAGATGAAACCGCAGCTGCGCATCGT

CAACACCGGCTCGCAAGCCGTGCCGCTGACCGAGCTGAAGATGCGCTACTGGTACACGAA

GAACTCGACGCAGGCCGAACAATACTTCTGCGACTGGGCGCAGATCGGCTGCTCGAACAT

CCGGGCGCAGTTCGTGTCGCTGTCGCAGCCGGTCAGCGGGGCGGACAGCTACATCGAGCT

GAGCTTTACGGGCGGAAGCATTCCGGCGGGAGGCAACACGGGCGAGATTCAGAACCGGAT

TCACTTCACGAACTGGATGAACTACAACGAAACGGACGACTGGTCGTACAACGGGGCGCA

GATGACGTGGGGGCCGTCGACGCGGATTACGCTTTATCGCAACGGCGTGCTGGTGTGGGG

CACGGAGCCGGGCGGCGGATCGTCGCCGCCGACGCCGACGGTGACACCGACACCTACACC

GACATCGACGCCGACACCTACGCCTACGCCGAGTGCGGCGCCCACACCGACGCCGTCGGC

CGGCGGCAGCCTAGTCGTGCAGTATCGCGCGGCGGACACGAACGCGGGCGACAACCAGCT

GAAGCCGCATTTTCGGATTGTGAACCGCGGGACGACGAGCGTGCCGCTGTCGGAGCTTTC

GATCCGGTACTGGTACACGGTGGACGGGGACAAGCCGCAGGTGTTCAACTGCGACTGGGC

GCAGGTGGGTTGTTCGAACTTGCGGGGCAGCTTCGTGAAGCTTTCGACGGGCCGGACGGG

GGCGGACTACTACATCGAGATCACGTTTACGTCGGGCGCGGGCAGTCTGGCGCCTGGGGC

GAGCAGCGGAGACATTCAGGTGCGGATCAACAAGAACGACTGGACGAACTACAACGAGGC

GAACGACTACTCGTATGACCCGACGAAGACGAGTTTTGCGGATTGGAACCGGGTGACGCT

GTATCGGAATGGTCAGCTCGTCTGGGGCGTTGAACCATAATAACGGCAAGCACAACTCGG

CCAGGTCGTTTCTCCAAAGCCCTTCTTTCGGAAGTATCGAAAGAAGGGCTTTCCTTCTAA

ACTTTTTCGGGGTGACATCTAAAGTTTATCCCGTACTCGAAGGATCGAGAGAAACGATAG

AATAGGCAATAAGTTACTGTAAATCTTGTATGAACAGAAAGGAGATGATTACAAAAGGAC

GGATTCATCGTTTTTTTTCGAAAAGGTCGGCAGTAGGTCTGTTTGAGACGGGATCACACA

TGCATCAAATTGCAGAGAGGAGGAAAATGATAATGCGAAACTGGCTCCAATGGGGCATGG

TTGCGGCTTTGCTCGTTTTTACGGTATCGGTCGTCCCCCCGAAAGAAGCCGATGCAGGGC

TAGCCAAGACAAAATTCTTGGGGAATGTCATCAACAATAGCATCCCTTCTGATTTTGCTG

TTTACTGGAATCAGGTTACCCCTGAAAACGCTACCAAGTGGGGTTCGGTCGAATCCAGCC

GCGACAACATGAACTGGTCGACGGCCGATATGATTTACAACTACGCTCGCAGTAACGGTT

TTCCGTTCAAATTCCACACACTGGTCTGGGGGAGTCAGGAGCCCGGCTGGATCAGCGGGC

TTTCGGCTGCAGAACAACAGGCCGAAGTGATCGAATGGATCCAAGCGGCCGGTCAGCGTT

ATCCCGACGCAGACTTCGTCGACGTCGTCAACGAACCGCTGCACGCCAAACCTTCCTACC

GCAATGCCATCGGCGGAGACGGCTCGACAGGTTGGGACTGGGTCATCTGGTCGTTCGAAC

AGGCGCGCCGCGCATTCCCCAATTCCAAATTGCTGATTAACGAGTACGGCGTCGAGAACG

ACCCGAATGCGGCGAGCCAATATGTCCAAATCATCAATCTGTTAAAAAGCCGCGGCTTGA

TCGACGGCATCGGCATTCAAGGTCATTATTTCAATCTTGACACGGTTTCAGTCAGTACGC

TGCGAACCACGCTCGGTATGCTTGCTGAAACAGGTTTGCCTATTTATGTGTCAGAACTGG

ATATTTCGGGTGATGACGCCACGCAATTGGCTAGATATCAAGAAAAGTTCCCAATTCTAT

GGGAACATCCTTCTGTCCAAGGGATTACGCTGTGGGGCTATATTGAAGGTCAAACCTGGA

GATCCGGCACGCATTTGATTACGGCTTCGGGCGTGGAACGACCTGCGTTGCAATGGTTGC

GGACGTATTTGGCAGGAGCCGGATCCTCGCCGACACCAACGCCGACGCCCACACCGACCG

-continued

TGACACCAACGGTGACGCCGACACCGACGCCTAGCGCGAACGGCACCCTGCGCGTCGAGT

ATCGCGTGGGCGACTCTAGCGCCACCGACAACCAGATGAAACCGCAGCTGCGCATCGTCA

ACACCGGCTCCCAAGCCGTGCCTCTGACCGAGCTGAAGGTGCGCTACTGGTACACGAAGA

ACTCGACGCAGGCCGAACAGTACTTCTGCGACTGGGCGCAGATCGGCTGCTCGAACATCC

GGGCGCAGTTCGTGTCGCTGTCGCAGCCGGTCAGCGGGGCGGACAGCTACATCGAGCTGA

GCTTCACGGGCGGAAGCATTCCGGCGGGAGGCAACACGGGCGAGATACAGAACCGGATTC

ACTTCACGAACTGGATGAACTACAACGAAACGGACGACTGGTCGTACAACGGGGCGCAGA

CGACGTGGGGGCCGTCGACGCGGATTACGCTGTATCGCAACGGCGTGCTGGTATGGGGCA

CGGAGCCGGGCGGATCGTCGACGCCGACACCGACACCGACGCCGACCCCTACGCCTACGC

CGAGCGCGGCGCCCACACCGGCGCCGTCGGCCGGCGGCAGCCTGGTCGTGCAGTATCGCG

CGGCGGACACGAACGCGACGGACAACCAGCTGAAGCCGCATTTTCGGATTGTGAACCGCG

GGACGACGAGCGTGCCGCTGTCGGAGCTAACGATTCGGTACTGGTACACGGTAGACGGAG

ACAAGCCGCAGGTGTTCAACTGCGACTGGGCGCAGGTGGGCTGCTCAAACGTGCGGGGCA

GCTTCGTGAAGCTTTCGACGGGCCGGACGGGGGCGGACTACTATATTGAGATCACGTTCA

CGTCAGGCGCGGGGAGCCTGGCGCCTGGGGCGAACAGCGGAGACATTCAGGCGCGGATCA

ACAAGAACGACTGGACGAACTACAACGAGGCGAACGACTACTCGTATGATCCGACGAAGA

CGAGTTTTGCGGATTGGAACCGGGTGACGCTGTATCGGAACGGTCAGCTCATCTGGGGCG

TCGAACCCTGA

The amino acid sequence of the *Paenibacillus* sp. A59 (WP_053783505) GH9 is as follows:

(SEQ ID NO: 8)

MKGSWWRRVVILALSTGLLAGSTSIQAWNGKADAAAGNHNYAEALQKAIY

FYETQRSGKLPEDNRVEWRGDSGLNDGADVGVDLTGGWYDAGDHVKFGVP

MAYSATMLAWSVVEYREGYEQAGQLEEIKDNLKWATDYFVRAHTKPNELW

GQVGAGNTDHAWWGPAEVMQMNRPAYKIDASCPGSELAGETAAALASSSI

VFRDSDPAYANKLLQHAKELYSFADTYRGKYSDCITDAQSFYNSWTGYYD

ELAWAATWLYMATNDSAYLSKAIATANLWQADGQSGNWAYTWTQGWDDKH

YGAQILLARITSSLNMPEAARFIQSTERNLDYWSVGTNGQRIKYTPGGLA

WLDTWGSLRYAANASFIAFVYSDWVSDPVKKARYQDFAVSQMNYILGDNP

RQSSYVVGYGQNPPKHPHHRTSHSSWTNNENVPSEHRHTLYGAMVGGPDA

SDAYTDSIGDYVSNEVATDYNAGFTGALAKMNLLFGQNNQPIANFPAPEV

KSDEFFVEASVKASGSNYTEIKAQLNNRSGWPARMGDKLSFRYFVDLSEV

YAAGYTVSDVHVTTAYAEGAIVSQPDVVDAVKRIYAVTADFTGTKIYPGG

EGHYRKEVQFRITGPEGAWNANNDHSFQGLGTGNVAKSAYLPVYDAGIRI

YGQEPGITPVVTPIAPSGVQAVSGNAQVILNWIASPGAESYTVKRAEVNG

GPYTSVATNVLGLTYTNTGLTNGKTYYYVVTAVNSVGESPGSAQATATPQ

AGTSLPGALTLSGTAGNTQSILTWTAATGAVSYKVQRAAGGSAYADVATG

LAVLNYTDATAANGTAYSYRIAAVNASGQTLSNIVTLTPSAPPATTGTLE

VQYRNGGSGASGNAVTPQFNLKNTGTQPIDLSTVKLRYYFTKDGTGDLTF

-continued

WCDYAQIGSANIEGKFVTLNPAKGTADTVLEISFQSGAGSLAAGAETGVI

QGRFSKNNWSNFDQSNDYSYDATKTAFTTWNQVIGYQGGTKVWGIEP

The amino acid sequence of the *Paenibacillus borealis* GH48 (AIQ60376) is as follows:

(SEQ ID NO: 9)

MKLSSIKKPFSIVMAAILIISLTSGIFNFRPGTAKAASVEKTRFLQLYAQ

LKDPASGYFSAEGIPYHSVETLLSEAPNYGHMTTSEAYSYWMWLEVLYGY

NTGDWSKLEAAWDNMEKYIIPINEGDGVQEQPTMNNYNPNSPATYASELA

QPDQYPSALNGKYAPGKDPLDAELKAAYGNNQTYLMHWLVDVDNWYGFGN

LLNPTHTAAYVNTFQRGVQESVWEAVAHPSQDDKSFGKTNEGFMSLFTKE

NSVPSAQWRYTNATDADARAVQAMYWAKDLGYTNTVYLNKAKKMGDFLRY

GMYDKYFQKVGSAADGTPEAGTGKDSSQYLLAWYTAWGGGLGTTGNWAWR

IGASHAHQGYQNVVAAYALSTADGGLIPASATAGEDWGKSLTRQLEFYNW

LQSSEGAIAGGATNSYGGSYSAYPSGTSTFYGMAYDEAPVYHDPPSNNWF

GMQAWSLERVAELYYILASSGDTTSANFKMAKRVIENWIDWSADYAFAGS

RPVTDAAGYYLDLQGNRILGGDDPQIATVSAPGEFWIPGNVEWQGQPDTW

SGFSSFSGNSGLKAVTKDPGQDTGVLGSYIKALTFFAAGNKAEHGSYTAL

GGTASQLAKSLLDTAWGYNDGVGITTLEKRADYFRFFTKEVYFPAGWTGT

FGQGNTIPGSSTVPSDPAKGGNGVYASYTDVLPDIKNDPKWSYLEGKYNS

SYNKTTKTWDNGAPEFTYHRFWSQVDIATAYAEYDRLINNGSGPIPTATP

TTTPTATPTVTPTATPTATPTVTPTATPTVTPTATPIATPTATPTATPTA

-continued

TPTATPAAANLVVQYRTTDTNATDQQFRPQLRIVNNGTTAVDLSKVKLRY

YYTIDGEKAQQFNVDYATLGGSNVLGSFVKLEPAVAGADYYVEISFSTGA

GSLAPGANTGEIQLRINKTDWSNYNKADDYSYDSTKTAYTDWNRVTLYLN

GVRVWGVQPQ

The amino acid sequence of the *Cohnella laeviribosi* GH10 is as follows:

(SEQ ID NO: 10)
MSKAKAMKICASLLLLGSVFSFIATSDADAGLARSKFLGNVIASSVPSNF

ATYWNQVTPENSTKWGSVEATRNVMNWSAADLAYNYAKSNGFPFKFHTLV

WGSQQPGWISGLSQAEQKAEVLQWIQAAGQRYPNADFVDVVNEPLHAKPS

YRNAIGGDGATGWDWVIWSFQEARKAFPNAKLLINEYGIISDPNAANQYV

QIINLLKSRGLIDGIGIQCHYFNMDSVSVSTMNSVLNTLAATGLPIYVSE

LDMTGDDSTQLARYQQKFPVLWEHSAVKGVTLWGYIEGQTWASNTHLVRS

NGTERPALQWLRTYLSTH

The amino acid sequence of the *Caldibacillus cellulovorans* beta-1,4-mannanase precursor is as follows:

(SEQ ID NO: 11)
MNRRLIARLSGMLAMVLIAAMLAYVPKPEPAEAHGGMVFPATRTYACYVD

GKVHGNGGDLNMINPACLDALAISGNYQFWNWFGNLISNAGGRHREIIPD

GKLCGPTASFDGMNQARTDWWTTRLQPGATITVRVNAWAPHPGTWYLYVT

RDGWDPTQPLKWSDLEPTPFSQVTNPPINSSGPDGAEYSWQVQLPNKQGR

HIIYMIWQRSDSPEAFYNCSDVYFGSGPIAYEFGDPREGGTMITPPPSGT

TPTPTPTPTPTSTPTPTPTPSVTPTVTPTSTPTPSASGTLRVEYRVGDTS

ATDNQMKPQLRIVNTGSQAVPLTELKVRYWYTKNSTQAEQYFCDWAQIGC

SNIRAQFVSLSQPVSGADSYIELSFTGGSIPAGGNTGEIQNRIHFTNWMN

YNETDDWSYNGAQTTWGPSTRITLYRNGVLVWGTEPGGGSSPPTPTVTPT

PTPTPTSTPTPTPTPTSTPTPSGGPNLSVNTQGLVGINHPHAWYRDRLSS

SLQGIRSWGANAVRIVLSNGCRWTKIPASEVADIISQARTLGYRAVVLEV

HDTTGYGEDAAACSMTTAVNYWIELKNVLAGQENFVIVNIGNEPYGNNNY

QNWVTDTRNAVQALRNAGINNTIMVDAPNWGQDWSFTMRDNAPTIFNADP

QRNLVFSIHMYGVYDTAAEVQSYIESFVNRGLPLVIGEFGHMHSDGDPNE

QAIVQYAKQYNIGLFGWSWSGNGGGVEYLDMVTNFNANSPTAWGTWFRTN

AIGTSTSPTPTPTPTPTPTPTPTPSAGGNLVVQYRAADTNATDNQLKP

HFRIVNRGTSSVPLSELTIRYWYTVDGDKPQVFNCDWAQVGCSNLRGSFV

KLSTGRTGADYYIEITFTSGAGSLAPGASSGDIQVRINKNDWTNYNEAND

YSYDPTKTSFADWNRVTLYRNGQLVWGVEP

The amino acid sequence of the *Caldibacillus cellulovorans* beta-1,4-xylanase XynA precursor is as follows:

(SEQ ID NO: 12)
MGTGRAGEWIKKMLLVLAIGLLIPIPYPHVASAENVLILQSDFEDGTTQG

WVGRGGVETLTVTSAAAYSGAYGLSVSGRTETWHGPTLDITSYIQVGKTY

-continued

QFSAWVKLPSGSSNTRISMTMQRTMQDTVYYEQIYFDTALSGNWIQLKAQ

YKLYEPAVNLQVYFEAPDHATQSFYIDDVRIEQLPDLPKTVEENIPSLKD

VFAGRFPIGTAFENFELLDEQDRKLILKHFNSVTPGNVLKWDSTEPQEGV

FNFTESDKAVAFAVQNGMKIRGHTLIWHNQTPNWVFYDSNGNLVSKEVLY

QRMERHIKTVVSRYKGIIYAWDVVNEVIDPGQPDGLRRSLWYQIAGEEYI

EKAFQFAHEADPNALLFINDYNTHESGKSQALYNLVQRLKSKGIPVHGVG

HQTHINITWPSISEIENSLVKFSNLGVVQEITELDMSIYNNSSQKYDTLP

SDLAQQQATRYRQLFEMFLRRSSLIQNVTFWGKDDANTWLRKFPVVRNDW

PLLFDEQLKAKPAYWAVVGTVPSPTPTPTSTATPTPTPTVIPTPTPTPTP

TSTPTPTPTPSASGTLRVEYRVGDSSATDNQMKPQLRIVNTGSQAVPLTE

LKVRYWYTKNSTQAEQYFCDWAQIGCSNIRAQFVSLAQPVSGADSYIELS

FTGGSVPAGGNTGEIQNRIHFTNWMNYNETDDWSYNGTQTTWGPSTRITL

YRNGVLVWGTEPGGGSSTPTPTPTPTPTPTSTPTPTPTPTSTPTPTPTPT

STPTPTATPTPTPTPTPSAGGNLVVQYRAADTNAGDNQLKPHFRIVNRGT

TSVPLSELTIRYWYTVDGDKPQVFNCDWAWVGCSNLRGSLVKLTTGRTGA

DYYLEITFTSGAGSLAPGANSGDIQARINKNDWTNYNEANDYSYDPTKTS

FADWNRVTLYRNGQLVWGVEP

Ionic Liquid (IL)

The suitable IL that can be used in the present invention can be any IL that does not impede the enzymatic activity of any of the GH polypeptide or the cellulase complex. In some embodiments of the invention, the IL is suitable for pretreatment of biomass and for the hydrolysis of cellulose by any of the GH polypeptide or the cellulase complex. Suitable IL are taught in ChemFiles (2006) 6(9) (which are commercially available from Sigma-Aldrich; Milwaukee, Wis.). Such suitable IL include, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

Such suitable IL include, but are limited to, 1-ethyl-3-methylimidazolium acetate (EMIN Acetate), 1-ethyl-3-methylimidazolium chloride (EMIN Cl), 1-ethyl-3-methylimidazolium hydrogensulfate (EMIM $HOSO_3$), 1-ethyl-3-methylimidazolium methylsulfate (EMIM $MeOSO_3$), 1-ethyl-3-methylimidazolium ethylsulfate (EMIM $EtOSO_3$), 1-ethyl-3-methylimidazolium methanesulfonate (EMIM $MeSO_3$), 1-ethyl-3-methylimidazolium tetrachloroaluminate (EMIM $AlCl_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM $HOSO_3$), 1-butyl-3-methylimidazolium methanesulfonate (BMIM $MeSO_3$), 1-butyl-3-methylimidazolium methylsulfate (BMIM $MeOSO_3$), 1-butyl-3-methylimidazolium tetrachloroaluminate (BMIM $AlCl_4$), 1-butyl-3-methylimidazolium thiocyanate (BMIM SCN), 1-ethyl-2,3-dimethylimidazolium ethylsulfate (EDIM $EtOSO_3$), Tris(2-hydroxyethyl)methylammonium methylsulfate (MTEOA $MeOSO_3$), 1-methylimidazolium chloride (MIM Cl), 1-methylimidazolium hydrogensulfate (MIM $HOSO_3$), 1,2,4-trimethylpyrazolium methylsulfate, tributylmethylammonium methylsulfate, choline acetate, choline salicylate, and the like. The ionic liquid can comprises one or a mixture of the compounds. Further ILs are taught in U.S. Pat. No. 6,177,575; herein incorporated by reference.

The ionic liquid (IL) is of a concentration of more than 0% to 20% of the composition or solution. In some embodiments, the concentration of IL is equal to or more than 1%, equal to or more than 2%, equal to or more than 3%, equal to or more than 5%, equal to or more than 10%, equal to or more than 15%. In some embodiments, the upper range of the concentration of IL is equal to or less than 20%. In some embodiments of the invention, the IL has a concentration from more than 0% to about 20%. In some embodiments of the invention, the IL has a concentration from about 5% to about 20%.

The solution containing IL can further comprise NaCl, such as up to 10 mM of NaCl. The solution can further comprise a suitable buffer.

Host Cells

The host cells of the present invention are genetically modified in that heterologous nucleic acid have been introduced into the host cells, and as such the genetically modified host cells do not occur in nature. The suitable host cell is one capable of expressing from the nucleic acid of the present invention.

Any prokaryotic or eukaryotic host cell may be used in the present method so long as it remains viable after being transformed with a sequence of nucleic acids. Generally, although not necessarily, the host microorganism is bacterial. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus* taxonomical classes. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway.

Suitable eukaryotic cells include, but are not limited to, fungal, insect or mammalian cells. Suitable fungal cells are yeast cells, such as yeast cells of the *Saccharomyces* genus.

The present invention provides for an isolated GH polypeptide produced from the method of the present invention. Isolating the GH polypeptide involves the separating at least part or all of the host cells, and parts thereof, from which the GH polypeptide was produced, from the isolated GH polypeptide. The isolated GH polypeptide may be free or essentially free of impurities formed from at least part or all of the host cells, and parts thereof. The isolated GH polypeptide is essentially free of these impurities when the amount and properties of the impurities do not interfere in the use of the GH polypeptide as an enzyme. In some embodiments, these host cells are specifically cells that do not in nature produce the GH polypeptide. The impurities are no more than 5%, 1%, 0.5%, 0.1%, 0.05%, or 0.01% by weight of a composition comprising one or more of the GH polypeptide.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

This invention describes the identification of a new type of cellulase complex previously unobserved in natural systems. The active component of a cellulolytic microbial community was partially purified by affinity digestion and column chromatography and visualized by native polyacrylamide gels (Native PAGE), using both Coomassie staining and endoglucanase activity staining, which revealed a 350 kDa protein complex containing three cellulases, a glycoside hydrolase (GH) family 48 protein, a GH9 protein and GH6/5 protein. Reconstruction of the genes for these proteins indicated that each of these proteins contained at least cellulose-binding domain (CBM3) that may be involved in complex formation. The three proteins were located in a putative operon that also contained multiple GH10 proteins and an AA10 polysaccharide monooxygenase. The gene sequences of the complex lacked a scaffoldin domain and cohesion-dockerin pairs characteristic of anaerobic cellulosomes. The complex can be produced by heterologous expression of individual glycoside hydrolases in *E. coli* and used for the hydrolysis of polysaccharides in biomass. The catalytic domains in the GH9, GH48, and GH6/5 proteins can be replaced by heterologous expression with new catalytic domains to change or improve the hydrolysis of biomass and/or add new functions to the complex.

Materials and Methods

Cultivation of Adapted Consortia

Sample collection and enrichment procedures were described previously (1, 2). Briefly, compost sample are derived from Jepson Prairie (JP) Organics located in Vacaville, Calif. The compost-derived microbial consortium was adapted to switchgrass (SG) and microcrystalline cellulose (Avicel) as the sole carbon source in liquid culture at 60° C. (JP-148, 1% Avicel, and 1% SG) and passaged every 14 days. Characterizations were performed on a 300 L scale up of a passage carried out at the Advanced Biofuels Process Demonstration Unit-Lawrence Berkeley National Lab. The supernatant was separated from residual biomass by centrifugation, lyophilized, and stored at −20° C. for subsequent analysis.

Cellulase Enrichment by Column Chromatography

The lyophilized supernatant was resuspended in an appropriate volume of $H_2O$ and passed through a 0.2 um filter. The supernatant was desalted through PD-10 desalting columns (GE Healthcare, Little Chalfont, UK) or by dialysis against running buffer (20 mM Tris, pH 8.0) followed by gradual fractionization by anion-exchange chromatography (AIEX) with a 30 ml gradient with elution buffer (20 mM Tris, 2 M NaCl, ph 8.0) from HiTrap Q HP columns on an AKTA Protein Purification System (GE Healthcare, Little Chalfont, UK).

Furthermore, glycosidases in the supernatant protein concentrate were enriched solely and in addition to AIEX fractionation via binding to amorphous cellulose and subsequent affinity digestion as described previously (3). Briefly, acid-swollen Avicel PH-105 was added to the supernatant. After binding, the amorphous cellulose was separated by centrifugation and resuspended in 10 ml of reaction buffer containing 25 mM 2-(N-morpholino)ethanesulfonic acid (MES), pH 6.5. Affinity digestion was performed with dialysis membranes (SnakeSkin and Slide-A-Lyzer (Fisher Scientific, Pittsburgh, Pa., USA) with a 3.5- to 10-kDa cutoff) against reaction buffer at 55- to 60° C. for up to 48 h with frequent changes of the dialysis membranes and buffer to prevent possible membrane raptures and product inhibition. The reaction was considered complete after no visible changes of the substrate were observable.

Glycoside Hydrolase Activity Assays

The glycoside hydrolase activities were measured using the DNS (3,5-dinitrosalicylic acid) reducing sugar assay (endoglucanase, endoxylanase) and the p-nitrophenol (pNP) assay (0-D-glucosidase, cellobiohydrolase, β-D-xylosidase, and α-L-arabinofuranosidase) (5, 29). Heat-killed samples generated by heating the supernatant to 95° C. for 16 h were used as blanks. Activity units for all assays were calculated as μmol of sugar liberated $min^{-1}$ $ml^{-1}$ and reported as U/ml.

Zymography

SDS-PAGE and Native-PAGE (4) were performed with 8 to 16% Protean TGX protein gels (Biorad) with the Tris-glycin-SDS-buffer and Tris-glycin-buffer, respectively. Protein bands were stained with Coomassie blue dye. Protein bands with endoglucanase or endoxylanase activity were visualized using a modification of the zymogram technique as described previously (5). Gels were incubated in 2% carboxymethyl cellulose (CMC) or 2% xylan from Birchwood Protein Identification Proteins were excised from native gels and analyzed as previously described (6).

Reconstruction of Glycoside Hydrolase Genes

Small discontinuously contigs encoding partial glycoside hydrolases were identified by combining proteomics with metagenomics. PCR primers (Table 1) were deduced using the CLC Main Workbench (Qiagen, Hilden, Germany) and PCR products were cloned into pJET1.2/blunt Cloning Vector (Fermentas, Waltham, Mass., USA) and sequenced with an ABI system according to the instructions of the manufacturer. Assembly of gene sequences into an operon and annotation of genes was performed with the CLC Main Workbench and checked for chimera using the Bellerophon algorithm (7).

Results

Identification of Cellulases Produced a Thermophilic Cellulolytic Consortium

Supernatant was obtained from a 300 L culture of a community grown in microcrystalline cellulose. The supernatant from this community high endo-glucanase and -xylanase activity. The supernatant was fractionated on an anion exchange column with an NaCl gradient. The majority of the glycoside hydrolase activity eluted in the salt gradient at <50 mM NaCl (FIG. 1).

Figure 2:
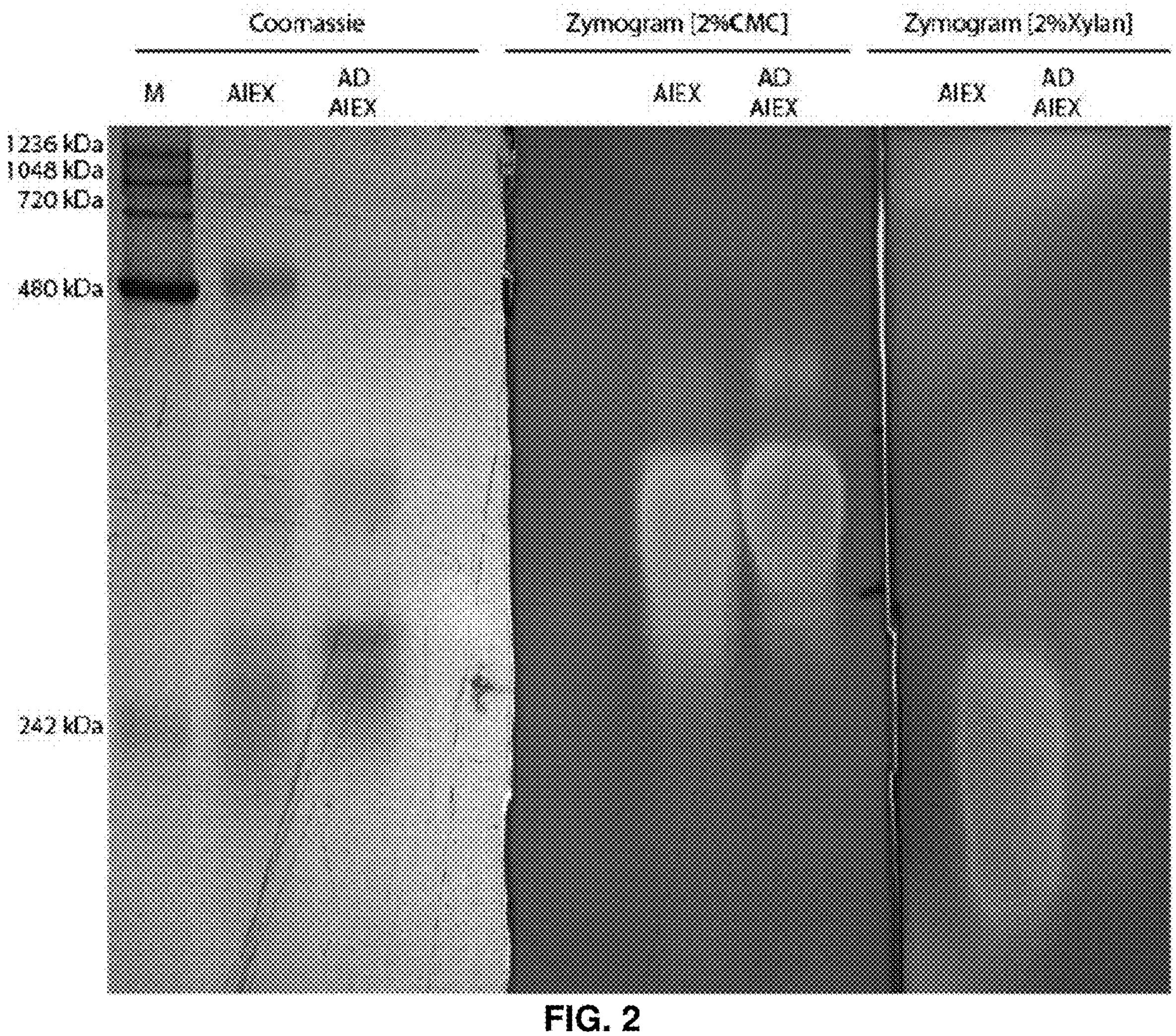
FIG. 2 shows Coomassie and activity staining (zymography) of endoglucanase and xylanase activity of anion-exchange and affinity digestion fractions of the 300 L supernatant.

In a second enrichment strategy, the cellulose-binding proteins were isolated by incubated the supernatant with amorphous cellulose; this step is referred to as affinity digestion (AD). In a subsequent step, the cellulose fraction was heated to 55° C., causing the cellulose to be digested. The supernatant after affinity digestion was separated using an anion-exchange column, producing a fraction enriched in complex identified by native gel that had an observed molecular weight of 350 kDa that stained positive for endoglucanase activity. Native PAGE in combination with zymograms showed a 100 kDa element in the anion-exchange fraction with high xylanase activity, which was missing in the AD fractions (FIG. 2).

Figure 3:
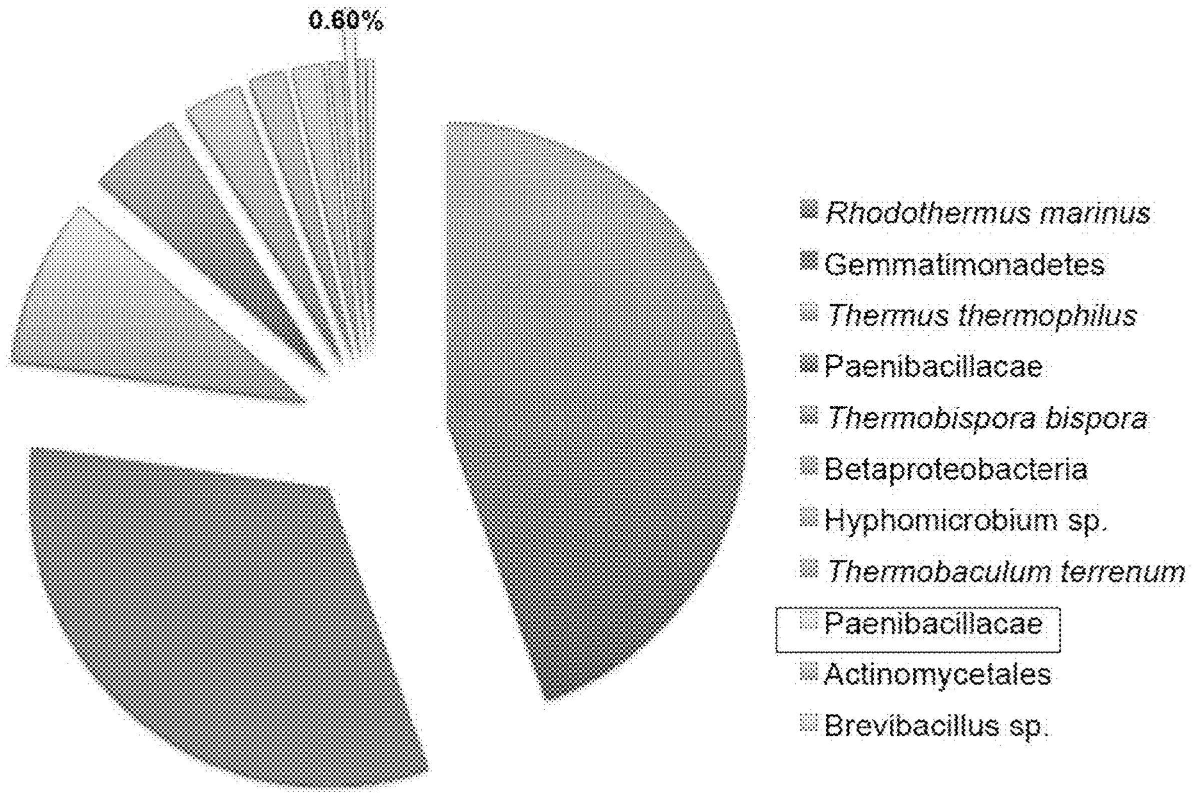
FIG. 3 shows a pie chart depicting relative abundances of metagenome for 300 L culture. Recovered genome in box in figure legend containing GH9, GH48 and GH6/5.

The 350 kDa band was excised and trypsin digested peptides analyzed against a database containing metagenomic data obtained from DNA isolated from the 300 L culture. Liquid chromatography-mass spectrometry (LC-MS) analysis of this complex identified unambiguously that the band consisted of three glycoside hydrolase (GH) proteins from low abundance member of the Firmicutes present at 0.6% abundance (FIG. 3). Partial genes were recovered from the metagenome that indicated that the three proteins were a GH9, GH48 and GH6/5.

Figure 4:
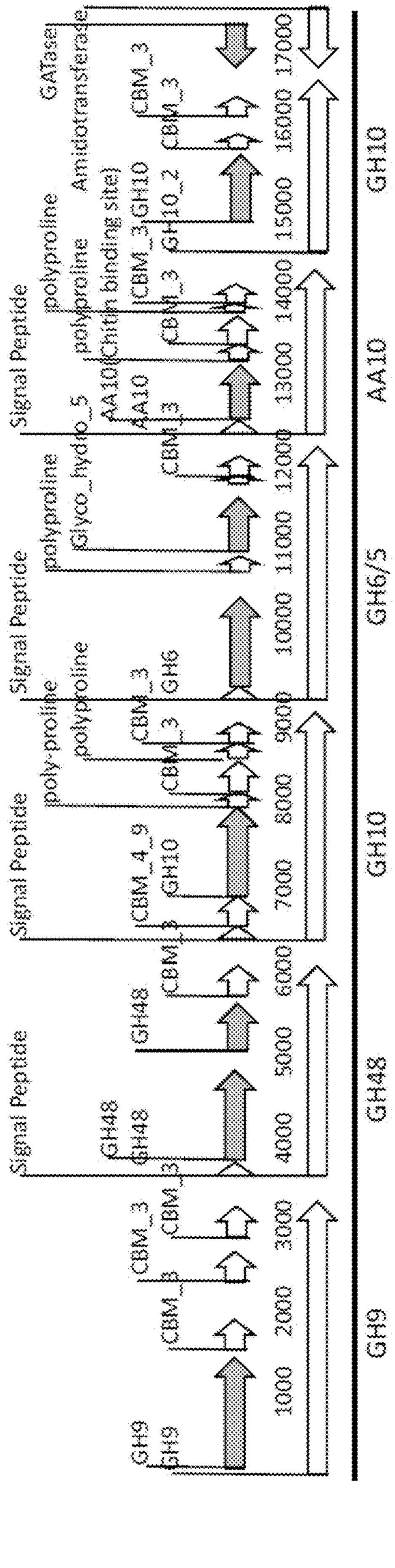
FIG. 4 shows a reconstructed putative operon containing GH9, GH48 and GH6/5 genes.

PCR-based extensions of the original genes indicated that the three genes coding for these cellulases were arranged in a putative operon with two GH10 proteins and on AA10 protein (FIG. 4).

A striking feature of the proteins in this operon was that each glycoside hydrolase contained at least one cellulose-binding domain (CBM), all in the CBM3 family. The GH9 contained three CBM3 domains and the GH48 and GH6/5 proteins contained one CBM3 each. No cohesion or dockerin domains were detected, leading to the hypothesis that the proteins in the complex were bound through the action of the multiple CBM domains. This structure represents a new motif in cellulase complex formation.

REFERENCES CITED

1. C. Li, B. Knierim, C. Manisseri, R. Arora, H. V. Scheller, M. Auer et al., Comparison of dilute acid and ionic liquid pretreatment of switchgrass: Biomass recalcitrance, delignification and enzymatic saccharification, Bioresource technology. 101, 4900-4906 (2010).
2. J. M. Gladden, M. Allgaier, C. S. Miller, T. C. Hazen, J. S. VanderGheynst, P. Hugenholtz et al., Glycoside hydrolase activities of thermophilic bacterial consortia adapted to switchgrass, Applied and environmental microbiology. 77, 5804-5812 (2011).
3. E. Morag, E. A. Bayer, R. Lamed, Affinity digestion for the near-total recovery of purified cellulosome from *Clostridium thermocellum*, Enzyme and Microbial Technology. 14, 289-292 (1992).
4. U. K. Laemmli, Cleavage of Structural Proteins during the Assembly of the Head of Bacteriophage T4, Nature. 227, 680-685 (1970).
5. Wolfgang H. Schwarz, Karin Bronnenmeier, Folke Gräbnitz, Walter L. Staudenbauer, Activity staining of cellulases in polyacrylamide gels containing mixed linkage β-glucans, Analytical Biochemistry. 164, 72-77 (1987).
6. Park J I, Steen E J, Burd H, Evans S S, Redding-Johnson A M, Batth T, Benke P I, D'Haeseleer P, Sun N, Sale K L, et al: A Thermophilic Ionic Liquid-Tolerant Cellulase Cocktail for the Production of Cellulosic Biofuels. PLoS ONE 7, e37010 (2012).
7. T. Huber, G. Faulkner, P. Hugenholtz, Bellerophon: a program to detect chimeric sequences in multiple sequence alignments, Bioinformatics (Oxford, England). 20, 2317-2319 (2004).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising an ionic liquid and a purified or isolated cellulase complex comprising two or more glycosidase hydrolases selected from the group consisting of a glycoside hydrolase 9 (GH9) polypeptide comprising an amino acid sequence at least 90% identical to SEQ ID NO:1 and the following amino acid sequences: SGKLP (SEQ ID NO:13), WRGDS (SEQ ID NO:14), DLTGGW (SEQ ID NO:15), DAGDHVKF (SEQ ID NO:16), WAVYEY (SEQ ID NO:17), DHAWWGPA (SEQ ID NO:18), EVMQM (SEQ ID NO:19), AVWLYLAT (SEQ ID NO:20), WDDVH (SEQ ID NO:21), GLAWLD (SEQ ID NO:22), WGSLRYA (SEQ ID NO:23), FLAFVYSDW (SEQ ID NO:24), RPHHRTAH (SEQ ID NO:25), and SWADSQ (SEQ ID NO:26), a glycoside hydrolase 48 (GH48) polypeptide comprising an amino acid sequence at least 90% identical to SEQ ID NO:2 and the following amino acid sequences: PANGYF (SEQ ID NO:27), GIPYHS (SEQ ID NO:28), EAPDYGH (SEQ ID NO:29), TTSEAFSY (SEQ ID NO:30), TGDWSK (SEQ ID NO:31), PATYA (SEQ ID NO:32), DVDNWYG (SEQ ID NO:33), NTFQRG (SEQ ID NO:34), ESVWE (SEQ ID NO:35), QWRYT (SEQ ID NO:36), DADARAIQ (SEQ ID NO:37), KMGDYLRY (SEQ ID NO:38), FDKYF (SEQ ID NO:39), SAHYLLSWY (SEQ ID NO:40), GYQNP (SEQ ID NO:41), GGATNS (SEQ ID NO:42), TFYGM (SEQ ID NO:43), PVYRDP (SEQ ID NO:44), WFGFQAWS (SEQ ID NO:45), GQPDTW (SEQ ID NO:46), YTGNPN (SEQ ID NO:47), and YHRFWAQ (SEQ ID NO:48), a glycoside hydrolase 10 (GH10) polypeptide comprising an amino acid sequence identical to SEQ ID NO:3, and a glycoside hydrolase 6 (GH6) polypeptide comprising an amino acid sequence identical to SEQ ID NO:4.

2. The composition of claim 1, wherein the purified or isolated cellulase complex further comprises a glycoside hydrolase 10_2 (GH10_2) polypeptide comprising an amino acid sequence at least 90% identical to SEQ ID NO:5, wherein the amino acid sequence comprises the following amino acid sequences: ADAGLA (SEQ ID NO:49), KFLGNVI (SEQ ID NO:50), YWNQVTPEN (SEQ ID NO:51), TKWGSVE (SEQ ID NO:52), SNGFPFKFHTLVWGSQ (SEQ ID NO:53), PGWISGLS (SEQ ID NO:54), WIQAAGQRYP (SEQ ID NO:55), ADFVDWNEPLHAKPSYRNAIGGDG (SEQ ID NO:56), TGWDWVIWSF (SEQ ID NO:57), KLLINEYG (SEQ ID NO:58), DPNAA (SEQ ID NO:59), QYVQIINLLKSRGLIDGIGIQ (SEQ ID NO:60), VSVST (SEQ ID NO:61), TGLPIYVSELD (SEQ ID NO:62), TQLARYQ (SEQ ID NO:63), TLWGYIEGQTW (SEQ ID NO:64), and ERPALQWLRTYL (SEQ ID NO:65).

3. The composition of claim 1, wherein the purified or isolated cellulase complex further comprises an auxiliary activity 10 (AA10) polypeptide comprising an amino acid sequence at least 90% identical to SEQ ID NO:6, wherein the amino acid sequence comprises the following amino acid sequences: MNRRLIARLSGMLAMVLIAA (SEQ ID NO:66), LAYVPKPEPAEAHGGMVFPATRTYACYVDGKVHGNGGDLNMINPACLDALAIS GNYQFWNWFGNLISNAGGRHREIIPDGKLCGPTASFDGMNQARTDWWTTRLQ PGATITVRVNAWAPHPGTWYLYVTRDGWDPTQPLKWSDLEPTPFSQVTNPPIN SSGPDGAEYSWQVQLPNKQGRHIIYMIWQRSDSPEAFYNCSD (SEQ ID NO:67), and YFGSGPIAYEFGDPREGGT (SEQ ID NO:68).

4. The composition of claim 1, wherein the purified or isolated cellulase complex comprises: (a) the GH9 polypeptide comprising an amino acid sequence at least 90% identical to SEQ ID NO:1 and the following amino acid sequences: SGKLP (SEQ ID NO:13), WRGDS (SEQ ID NO:14), DLTGGW (SEQ ID NO:15), DAGDHVKF (SEQ ID NO:16), WAVYEY (SEQ ID NO:17), DHAWWGPA (SEQ ID NO:18), EVMQM (SEQ ID NO:19), AVWLYLAT (SEQ ID NO:20), WDDVH (SEQ ID NO:21), GLAWLD (SEQ ID NO:22), WGSLRYA (SEQ ID NO:23), FLAFVYSDW (SEQ ID NO:24), RPHHRTAH (SEQ ID NO:25), and SWADSQ (SEQ ID NO:26); (b) the GH48 polypeptide comprising an amino acid sequence at least 90% identical to SEQ ID NO:2 and the following amino acid sequences: PANGYF (SEQ ID NO:27), GIPYHS (SEQ ID NO:28), EAPDYGH (SEQ ID NO:29), TTSEAFSY (SEQ ID NO:30), TGDWSK (SEQ ID NO:31), PATYA (SEQ ID NO:32), DVDNWYG (SEQ ID NO:33), NTFQRG (SEQ ID NO:34), ESVWE (SEQ ID NO:35), QWRYT (SEQ ID NO:36), DADARAIQ (SEQ ID NO:37), KMGDYLRY (SEQ ID NO:38), FDKYF (SEQ ID NO:39), SAHYLLSWY (SEQ ID NO:40), GYQNP (SEQ ID NO:41), GGATNS (SEQ ID NO:42), TFYGM (SEQ ID NO:43), PVYRDP (SEQ ID NO:44), WFGFQAWS (SEQ ID NO:45), GQPDTW (SEQ ID NO:46), YTGNPN (SEQ ID NO:47), and YHRFWAQ (SEQ ID NO:48); (c) the GH10 polypeptide comprising an amino acid sequence identical to SEQ ID NO:3; and (d) the GH6 polypeptide comprising an amino acid sequence identical to SEQ ID NO:4.

5. The composition of claim 1, wherein the concentration of IL in the composition is equal to or more than 1%.

6. The composition of claim 4, wherein (a) the GH9 polypeptide comprises an amino acid sequence at least 95% identical to SEQ ID NO:1; and (b) the GH48 polypeptide comprises an amino acid sequence at least 95% identical to SEQ ID NO:2.

7. The composition of claim 6, wherein (a) the GH9 polypeptide comprises an amino acid sequence at least 99% identical to SEQ ID NO:1; and (b) the GH48 polypeptide comprises an amino acid sequence at least 99% identical to SEQ ID NO:2.

8. The composition of claim 7, wherein (a) the GH9 polypeptide comprises an amino acid sequence identical to SEQ ID NO:1; and (b) the GH48 polypeptide comprises an amino acid sequence identical to SEQ ID NO:2.

* * * * *

SEQUENCE LISTING

```
<160> NUMBER OF SEQ ID NOS: 68

<210> SEQ ID NO 1
<211> LENGTH: 1070
<212> TYPE: PRT
<213> ORGANISM: Unknown
<220> FEATURE:
<223> OTHER INFORMATION: Enzyme identified in supernatant from a
      bacterial consortium

<400> SEQUENCE: 1

Met Leu Arg Arg Arg Ala Leu Ser Met Leu Thr Gly Ala Ala Val Val
1               5                   10                  15

Tyr Ser Ala Phe Val Pro Val Gly Ser Pro Asp Ser Ala Val Val Arg
            20                  25                  30

Ala Ala Pro Thr Ser Tyr Asn Tyr Ala Glu Ala Leu Gln Lys Ala Ile
        35                  40                  45

Tyr Phe Tyr Asp Ala Gln Arg Ser Gly Lys Leu Pro Pro Asp Asn Arg
    50                  55                  60

Val Glu Trp Arg Gly Asp Ser Gly Leu Asn Asp Gly Ala Asp Val Gly
65                  70                  75                  80

Val Asp Leu Thr Gly Gly Trp Tyr Asp Ala Gly Asp His Val Lys Phe
                85                  90                  95

Gly Leu Pro Met Ala Tyr Ser Ala Ala Met Leu Ala Trp Ala Val Tyr
            100                 105                 110

Glu Tyr Arg Asp Ala Phe Val Gln Thr Gly Gln Leu Asp Tyr Ile Leu
        115                 120                 125

Asn Asn Ile Lys Trp Ala Thr Asp Tyr Phe Ile Lys Ala His Ser Ala
    130                 135                 140

Pro Asn Val Leu Trp Gly Gln Val Gly Lys Gly Asp Val Asp His Ala
145                 150                 155                 160

Trp Trp Gly Pro Ala Glu Val Met Gln Met Pro Arg Pro Ala Tyr Lys
                165                 170                 175

Ile Asp Pro Ser Cys Pro Gly Ser Asp Leu Ala Ala Gly Thr Ala Ala
            180                 185                 190

Ala Met Ala Ala Ala Ala Ala Val Phe Lys Pro Thr Asp Pro Thr Tyr
        195                 200                 205

Ala Ser Thr Leu Ile Ala His Ala Lys Gln Leu Tyr Thr Phe Ala Asp
    210                 215                 220

Thr Tyr Arg Gly Lys Tyr Ser Asp Cys Ile Thr Asp Ala Gln Asn Phe
225                 230                 235                 240

Tyr Arg Ser Trp Ser Gly Tyr Ala Asp Glu Leu Thr Trp Gly Ala Val
                245                 250                 255

Trp Leu Tyr Leu Ala Thr Gly Glu Gln Ala Tyr Leu Asp Lys Ala Ile
            260                 265                 270

Ala Ser Val Ala Glu Trp Gly Arg Glu Gly Gln Thr Pro Tyr Trp Gly
        275                 280                 285

Tyr Lys Trp Thr Gln Ser Trp Asp Asp Val His Tyr Gly Ala Gln Leu
    290                 295                 300

Leu Leu Ala Arg Ile Thr Gly Asp Gln Arg Phe Ile Gln Ser Thr Glu
305                 310                 315                 320
```

-continued

```
Arg Asn Leu Glu Tyr Trp Thr Asp Gly Thr Asp Asp Thr Gly Glu Arg
                325                 330                 335

Ile Thr Tyr Thr Pro Gly Gly Leu Ala Trp Leu Asp Ser Trp Gly Ser
            340                 345                 350

Leu Arg Tyr Ala Met Asn Ala Ser Phe Leu Ala Phe Val Tyr Ser Asp
        355                 360                 365

Trp Leu Gln Ser Arg Asp Pro Ala Lys Ala Glu Lys Tyr Arg Asn Phe
    370                 375                 380

Ala Val Arg Gln Val Leu Tyr Ala Leu Gly Asp Asn Pro Arg Asn Ser
385                 390                 395                 400

Ser Tyr Val Val Gly Phe Gly Arg Asn Pro Pro Gln Arg Pro His His
                405                 410                 415

Arg Thr Ala His Gly Ser Trp Ala Asp Ser Gln Asn Val Pro Ala Tyr
            420                 425                 430

His Arg His Ile Leu Tyr Gly Ala Leu Val Gly Gly Pro Asn Gln Ser
        435                 440                 445

Asp Ala Tyr Thr Asp Ser Ile Ser Asp Tyr Val Gly Asn Glu Val Ala
    450                 455                 460

Thr Asp Tyr Asn Ala Ala Phe Thr Gly Asn Leu Ala Lys Met Tyr Leu
465                 470                 475                 480

Leu Phe Gly Ala Ser Ala Gly Gln Arg Pro Leu Ala Asn Phe Pro Glu
                485                 490                 495

Pro Glu Val Arg Glu Asp Glu Phe Phe Val Glu Ala Gly Val Asn Ser
            500                 505                 510

Ser Gly Pro Asn Tyr Thr Glu Ile Lys Ala Leu Ile Asn Asn Arg Ser
        515                 520                 525

Gly Trp Pro Ala Arg Met Gly Asp Lys Leu Ser Phe Lys Tyr Phe Val
    530                 535                 540

Asp Leu Ser Glu Val Tyr Ala Ala Gly Tyr Thr Val Asn Asp Ile Lys
545                 550                 555                 560

Val Thr Thr Asn Tyr Asn Glu Gly Ala Lys Val Ser Gly Leu Leu Pro
                565                 570                 575

Tyr Asp Glu Ser Arg Arg Leu Tyr Tyr Val Leu Val Asp Phe Thr Gly
            580                 585                 590

Thr Lys Ile Tyr Pro Gly Gly Gln Ser Ala Tyr Lys Lys Glu Val Gln
        595                 600                 605

Phe Arg Leu Ser Ala Pro Ser Gly Thr Ser Phe Trp Asn Pro Asn Asn
    610                 615                 620

Asp Phe Ser Tyr Gln Leu Met Ser Gly Thr Ser Asn Ser Ser Leu Val
625                 630                 635                 640

Lys Thr Pro Tyr Met Pro Val Tyr Asp Ala Gly Val Lys Ile Phe Gly
                645                 650                 655

Val Glu Pro Ser Ser Gly Ser Gly Ser Ser Pro Thr Pro Pro Pro Thr
            660                 665                 670

Ser Thr Pro Thr Pro Thr Pro Thr Pro Thr Pro Thr Pro Thr Leu Thr
        675                 680                 685

Leu Thr Pro Thr Pro Thr Pro Thr Pro Thr Pro Thr Pro Thr Pro Thr
    690                 695                 700

Pro Thr Pro Thr Pro Thr Pro Thr Pro Thr Pro Thr Pro Thr Pro Thr
705                 710                 715                 720

Pro Thr Pro Thr Pro Thr Pro Thr Pro Thr Pro Thr Pro Thr Pro Thr
                725                 730                 735
```

```
Pro Thr Pro Ser Ala Ser Gly Thr Leu Arg Val Glu Tyr Arg Val Gly
            740                 745                 750

Asp Thr Ser Ala Thr Asp Asn Gln Met Lys Pro Tyr Leu Arg Ile Val
        755                 760                 765

Asn Thr Gly Ser Gln Ala Val Pro Leu Thr Glu Leu Lys Val Arg Tyr
    770                 775                 780

Trp Tyr Thr Lys Asn Ser Thr Gln Ala Glu Gln Tyr Phe Cys Asp Trp
785                 790                 795                 800

Ala Gln Ile Asp Cys Ser Asn Ile Arg Ala Gln Phe Val Ser Leu Ala
                805                 810                 815

Gln Pro Val Ser Gly Ala Asp Ser Tyr Ile Glu Leu Ser Phe Thr Gly
            820                 825                 830

Gly Ser Val Pro Ala Gly Gly Asn Thr Gly Glu Ile Gln Asn Arg Ile
        835                 840                 845

His Phe Thr Asn Trp Met Asn Tyr Asn Glu Thr Asp Asp Trp Ser Tyr
    850                 855                 860

Asn Gly Thr Gln Thr Thr Trp Gly Pro Ser Thr Arg Ile Thr Leu Tyr
865                 870                 875                 880

Arg Asn Gly Val Leu Val Trp Gly Thr Glu Pro Gly Gly Gly Ser Ser
                885                 890                 895

Thr Pro Thr Pro Thr Ala Thr Pro Thr Pro Thr Pro Ser Ala Ala Pro
            900                 905                 910

Thr Pro Thr Pro Thr Ala Gly Gly Ser Leu Val Val Gln Tyr Arg Ala
        915                 920                 925

Ala Asp Thr Asn Ala Gly Asp Asn Gln Leu Lys Pro His Phe Arg Ile
    930                 935                 940

Val Asn Arg Gly Thr Thr Ser Val Pro Leu Ser Glu Leu Ser Ile Arg
945                 950                 955                 960

Tyr Trp Tyr Thr Val Asp Gly Asp Lys Pro Gln Val Phe Asn Cys Asp
                965                 970                 975

Trp Ala Gln Val Gly Cys Ser Asn Leu Arg Gly Ser Phe Val Lys Leu
            980                 985                 990

Ser Thr Gly Arg Thr Gly Ala Asp  Tyr Tyr Ile Glu Ile  Thr Phe Thr
        995                 1000                1005

Ser Gly  Ala Gly Ser Leu Ala  Ala Gly Gly Ser Ser  Gly Asp Ile
    1010                1015                1020

Gln Val  Arg Ile Asn Lys Asn  Asp Trp Thr Asn Tyr  Asn Glu Ala
    1025                1030                1035

Asn Asp  Tyr Ser Tyr Asp Pro  Thr Lys Thr Ser Phe  Ala Asp Trp
    1040                1045                1050

Asn Arg  Val Thr Leu Tyr Arg  Asn Gly Gln Leu Ile  Trp Gly Val
    1055                1060                1065

Glu Pro
    1070


<210> SEQ ID NO 2
<211> LENGTH: 912
<212> TYPE: PRT
<213> ORGANISM: Unknown
<220> FEATURE:
<223> OTHER INFORMATION: Enzyme identified in supernatant from a
      bacterial consortium

<400> SEQUENCE: 2

Met Glu Ser Leu Ala Trp Thr Leu Leu Trp Lys Lys Ala Arg Ile Ile
1               5                   10                  15
```

-continued

```
Phe Leu Ala Phe Ala Leu Val Val Ser Ala Phe Ala Gly Phe Ala Val
            20                  25                  30

Ser Pro Arg Ser Glu Thr Ala Tyr Ala Gln Thr Asp Pro Gln Val Phe
        35                  40                  45

Lys Asp Arg Phe Leu Gln Leu Tyr Asn Gln Ile Lys Asn Pro Ala Asn
    50                  55                  60

Gly Tyr Phe Ser Pro Glu Gly Ile Pro Tyr His Ser Ile Glu Thr Leu
65                  70                  75                  80

Ile Ser Glu Ala Pro Asp Tyr Gly His Met Thr Thr Ser Glu Ala Phe
                85                  90                  95

Ser Tyr Trp Leu Trp Leu Glu Thr Leu Tyr Gly Tyr Phe Thr Gly Asp
            100                 105                 110

Trp Ser Lys Leu Glu Gln Ala Trp Thr Lys Met Glu Gln Phe Ile Ile
        115                 120                 125

Pro Asn Ser Thr Glu Gln Pro Thr Met Gly Ser Tyr Asn Pro Ser Ser
    130                 135                 140

Pro Ala Thr Tyr Ala Pro Glu His Pro Tyr Pro Asp Arg Tyr Pro Thr
145                 150                 155                 160

Leu Leu Asn Asn Ser Val Pro Ala Gly Gln Asp Pro Leu Asp Ala Glu
                165                 170                 175

Leu Lys Ala Thr Tyr Gly Asn Asn Val Thr Tyr Leu Met His Trp Leu
            180                 185                 190

Leu Asp Val Asp Asn Trp Tyr Gly Phe Gly Asn Leu Leu Asn Pro Ser
        195                 200                 205

His Thr Ala Thr Tyr Val Asn Thr Phe Gln Arg Gly Glu Gln Glu Ser
    210                 215                 220

Val Trp Glu Ala Ile Thr His Pro Ser Gln Asp Asn Phe Arg Phe Gly
225                 230                 235                 240

Lys Pro Asn Glu Gly Phe Val Thr Leu Phe Val Lys Asp Asn Gly Thr
                245                 250                 255

Pro Ala Gln Gln Trp Arg Tyr Thr Ala Ala Ser Asp Ala Asp Ala Arg
            260                 265                 270

Ala Ile Gln Val Met Tyr Trp Ala Lys Gln Leu Gly Tyr Asn Asn Gln
        275                 280                 285

Thr Tyr Leu Asp Lys Ala Arg Lys Met Gly Asp Tyr Leu Arg Tyr Thr
    290                 295                 300

Leu Phe Asp Lys Tyr Phe Gln Gln Ile Gly Ser Ala Asn Asp Gly Ser
305                 310                 315                 320

Pro Ser Pro Gly Ser Gly Lys Asn Ser Ala His Tyr Leu Leu Ser Trp
                325                 330                 335

Tyr Thr Ala Trp Gly Gly Gly Leu Gly Ser Gly Gly Asn Trp Ala Trp
            340                 345                 350

Arg Ile Gly Ser Ser His Ala His Gln Gly Tyr Gln Asn Pro Val Ala
        355                 360                 365

Ala Tyr Ala Leu Ser Ala Gly Gly Leu Ala Pro Arg Ser Ala Thr Ala
    370                 375                 380

Gln Thr Asp Trp Ala Thr Ser Leu Gln Arg Gln Leu Glu Phe Tyr Thr
385                 390                 395                 400

Trp Leu Gln Ser Ser Glu Gly Ala Ile Gly Gly Gly Ala Thr Asn Ser
                405                 410                 415

Val Gly Gly Ser Tyr Gln Pro Tyr Pro Ser Gly Arg Ser Thr Phe Tyr
            420                 425                 430
```

-continued

```
Gly Met Val Tyr Asp Glu Ala Pro Val Tyr Arg Asp Pro Pro Ser Asn
        435                 440                 445

Ser Trp Phe Gly Phe Gln Ala Trp Ser Val Glu Arg Val Ala Glu Leu
    450                 455                 460

Tyr Tyr Ile Trp Thr Ser Ser Gly Asn Thr Asn Thr Gln Gln Phe Gln
465                 470                 475                 480

Met Val Lys Asn Ile Val Thr Lys Trp Val Asp Trp Ala Leu Asp Tyr
                485                 490                 495

Thr Phe Val Asn Gln Arg Pro Val Thr Asp Ala Gln Gly Tyr Phe Leu
            500                 505                 510

Thr Ser Ser Gly Ser Arg Val Leu Gly Gly Asn Asn Pro Gln Ile Ala
        515                 520                 525

Thr Val Ser Asp Pro Gly Gln Phe Tyr Ile Pro Ser Thr Leu Glu Trp
    530                 535                 540

Gln Gly Gln Pro Asp Thr Trp Asn Gly Tyr Ala Asn Tyr Thr Gly Asn
545                 550                 555                 560

Pro Asn Phe His Ala Ile Ala Lys Asp Pro Gly Gln Asp Val Gly Val
                565                 570                 575

Thr Gly Asn Tyr Ile Lys Leu Leu Thr Phe Phe Ala Ala Ala Thr Lys
            580                 585                 590

Ala Glu Thr Gly Asn Tyr Thr Ala Leu Gly Ser Gln Ala Leu Asn Val
        595                 600                 605

Ala Glu Gln Leu Leu Asn Val Leu Trp Asn Phe Asn Asp Gly Val Gly
    610                 615                 620

Ile Val Arg Pro Glu Gln Arg Ala Asp Tyr Phe Arg Tyr Phe Thr Lys
625                 630                 635                 640

Glu Ile Tyr Phe Pro Ser Gly Trp Ser Gly Thr Tyr Gly Gln Gly Asn
                645                 650                 655

Thr Ile Pro Gly Pro Gly Ala Val Pro Ser Asp Pro Ser Lys Gly Gly
            660                 665                 670

Asn Gly Val Tyr Ile Ser Tyr Ala Glu Leu Arg Pro Lys Ile Lys Gln
        675                 680                 685

Asp Pro Lys Trp Ser Tyr Leu Glu Asn Leu Tyr Lys Thr Ser Tyr Asn
    690                 695                 700

Pro Ser Thr Gly Arg Trp Glu Asn Gly Val Pro Thr Phe Thr Tyr His
705                 710                 715                 720

Arg Phe Trp Ala Gln Val Asp Val Ala Thr Ala Tyr Ala Glu Phe Ala
                725                 730                 735

Arg Leu Ile Gly Gly Leu Gly Ala Ser Pro Thr Pro Thr Pro Ser Ala
            740                 745                 750

Thr Pro Thr Pro Thr Pro Ser Ala Gly Gly Asn Leu Val Val Gln Tyr
        755                 760                 765

Arg Ala Ala Asp Thr Asn Ala Thr Asp Asn Gln Leu Lys Pro His Phe
    770                 775                 780

Arg Ile Val Asn Arg Gly Thr Thr Ser Val Pro Leu Ser Glu Leu Thr
785                 790                 795                 800

Ile Arg Tyr Trp Tyr Thr Val Asp Gly Asp Lys Pro Gln Val Phe Asn
                805                 810                 815

Cys Asp Trp Ala Gln Val Gly Cys Ser Asn Val Arg Gly Ser Phe Val
            820                 825                 830

Lys Leu Thr Thr Gly Arg Thr Gly Ala Asp Tyr Tyr Ile Glu Ile Thr
        835                 840                 845

Phe Thr Ser Gly Ala Gly Ser Leu Ala Ala Gly Gly Ser Ser Gly Asp
```

-continued

```
    850                 855                 860

Ile Gln Val Arg Ile Asn Lys Asn Asp Trp Thr Asn Tyr Asn Glu Ala
865                 870                 875                 880

Asn Asp Tyr Ser Cys Asp Pro Thr Lys Thr Ser Phe Ala Asp Trp Asn
                885                 890                 895

Arg Val Thr Leu Tyr Arg Asn Gly Gln Leu Val Trp Gly Val Glu Pro
            900                 905                 910


<210> SEQ ID NO 3
<211> LENGTH: 901
<212> TYPE: PRT
<213> ORGANISM: Unknown
<220> FEATURE:
<223> OTHER INFORMATION: Enzyme identified in supernatant from a
      bacterial consortium

<400> SEQUENCE: 3

Met Leu Leu Val Leu Ala Ile Gly Leu Leu Leu Pro Ile Pro Tyr Leu
1               5                   10                  15

His Val Ala Ser Ala Glu Asn Val Leu Ile Leu Gln Ser Asp Phe Glu
            20                  25                  30

Asp Gly Thr Thr Gln Gly Trp Val Gly Arg Gly Gly Val Glu Thr Leu
        35                  40                  45

Thr Val Thr Ser Ala Ala Ala Tyr Ser Gly Ala Tyr Gly Leu Ser Val
    50                  55                  60

Ser Gly Arg Thr Lys Thr Trp His Gly Pro Thr Leu Asp Ile Thr Ser
65                  70                  75                  80

Tyr Ile Gln Val Gly Lys Thr Tyr Gln Phe Ser Ala Trp Val Lys Leu
                85                  90                  95

Pro Ser Gly Ser Ser Asn Thr Arg Ile Tyr Met Thr Met Gln Arg Thr
            100                 105                 110

Met Gln Asp Thr Val Tyr Tyr Glu Gln Ile Tyr Phe Asp Thr Ala Ser
        115                 120                 125

Ala Gly Asn Trp Val Gln Leu Lys Ala Gln Tyr Lys Leu Tyr Glu Pro
    130                 135                 140

Ala Val Asn Leu Gln Val Tyr Phe Glu Ala Pro Asp His Ala Thr Gln
145                 150                 155                 160

Ser Phe Tyr Ile Asp Asp Val Arg Ile Glu Gln Leu Pro Asp Leu Pro
                165                 170                 175

Lys Thr Val Glu Glu Asn Ile Pro Ser Leu Lys Asp Val Phe Ala Gly
            180                 185                 190

Arg Phe Pro Ile Gly Thr Ala Phe Glu Asn Phe Glu Leu Leu Asp Glu
        195                 200                 205

Gln Asp Arg Lys Leu Ile Leu Lys His Phe Asn Ser Val Thr Pro Gly
    210                 215                 220

Asn Val Leu Lys Trp Asp Ser Thr Glu Pro Gln Glu Gly Val Phe Asn
225                 230                 235                 240

Phe Thr Glu Ser Asp Lys Ala Val Ala Phe Ala Val Gln Asn Gly Met
                245                 250                 255

Lys Ile Arg Gly His Thr Leu Ile Trp His Asn Gln Thr Pro Asn Trp
            260                 265                 270

Val Phe Tyr Asp Ser Asn Gly Asn Leu Val Ser Lys Glu Val Leu Tyr
        275                 280                 285

Gln Arg Met Glu Arg His Ile Lys Pro Val Val Ser Arg Tyr Lys Gly
    290                 295                 300
```

-continued

```
Ile Ile Tyr Ala Trp Asp Val Val Asn Glu Val Ile Asp Pro Gly Gln
305                 310                 315                 320

Pro Asp Gly Leu Arg Arg Ser Leu Trp Tyr Gln Ile Ala Gly Glu Glu
                325                 330                 335

Tyr Ile Glu Lys Ala Phe Gln Phe Ala His Glu Ala Asp Pro Asn Ala
            340                 345                 350

Leu Leu Phe Ile Asn Asp Tyr Asn Thr His Glu Ser Gly Lys Ser Gln
        355                 360                 365

Ala Leu Tyr Asn Leu Val Gln Arg Leu Lys Asn Lys Gly Ile Pro Val
    370                 375                 380

His Gly Val Gly His Gln Thr His Ile Asn Ile Ser Trp Pro Ser Ile
385                 390                 395                 400

Ser Glu Ile Glu Asn Ser Leu Val Lys Phe Ser Asn Leu Gly Val Val
                405                 410                 415

Gln Glu Ile Thr Glu Leu Asp Met Ser Ile Tyr Asn Asn Ser Ser Gln
            420                 425                 430

Lys Tyr Asp Thr Leu Pro Ser Asp Leu Ala Gln Gln Gln Ala Thr Arg
        435                 440                 445

Tyr Arg Gln Leu Phe Glu Met Phe Leu Arg Arg Ser Ser Leu Ile Gln
    450                 455                 460

Asn Val Thr Phe Trp Gly Lys Asp Asp Ala Asn Thr Trp Leu Arg Lys
465                 470                 475                 480

Phe Pro Val Val Arg Asn Asp Trp Pro Leu Leu Phe Asp Glu Gln Leu
                485                 490                 495

Lys Ala Lys Pro Ala Tyr Trp Ala Val Val Gly Thr Val Pro Ser Pro
            500                 505                 510

Thr Pro Thr Pro Thr Ser Thr Ala Thr Pro Thr Pro Thr Pro Thr Val
        515                 520                 525

Ile Pro Thr Pro Thr Pro Thr Pro Thr Pro Thr Ser Thr Pro Thr Pro
    530                 535                 540

Thr Pro Thr Ser Thr Pro Thr Pro Ser Ala Ser Gly Thr Leu Arg Val
545                 550                 555                 560

Glu Tyr Arg Val Gly Asp Ser Ser Ala Thr Asp Asn Gln Met Lys Pro
                565                 570                 575

Gln Leu Arg Ile Val Asn Thr Gly Ser Gln Ala Val Pro Leu Thr Glu
            580                 585                 590

Leu Lys Val Arg Tyr Trp Tyr Thr Lys Asn Ser Thr Gln Ala Glu Gln
        595                 600                 605

Tyr Phe Cys Asp Trp Ala Gln Ile Gly Cys Ser Asn Ile Arg Ala Gln
    610                 615                 620

Phe Val Ser Leu Ala Gln Pro Val Ser Gly Ala Asp Ser Tyr Ile Glu
625                 630                 635                 640

Leu Ser Phe Thr Gly Gly Ser Val Pro Ala Gly Gly Asn Thr Gly Glu
                645                 650                 655

Ile Gln Asn Arg Ile His Phe Thr Asn Trp Met Asn Tyr Asn Glu Thr
            660                 665                 670

Asp Asp Trp Ser Tyr Asn Gly Thr Gln Thr Thr Trp Gly Pro Ser Thr
        675                 680                 685

Arg Ile Thr Leu Tyr Arg Asn Gly Val Leu Val Trp Gly Thr Glu Pro
    690                 695                 700

Gly Gly Gly Ser Pro Thr Pro Thr Pro Thr Pro Thr Ser Thr Pro Thr
705                 710                 715                 720

Pro Thr Ser Thr Pro Thr Pro Thr Pro Thr Pro Thr Pro Thr Pro Thr
```

```
                725                 730                 735

Ala Thr Pro Thr Pro Thr Pro Thr Pro Thr Pro Ser Ala Gly Gly Asn
            740                 745                 750

Leu Val Val Gln Tyr Arg Ala Ala Asp Thr Asn Ala Gly Asp Asn Gln
        755                 760                 765

Leu Lys Pro His Phe Arg Ile Val Asn Arg Gly Thr Thr Ser Val Pro
    770                 775                 780

Leu Ser Glu Leu Thr Ile Arg Tyr Trp Tyr Thr Val Asp Gly Asp Lys
785                 790                 795                 800

Pro Gln Val Phe Asn Cys Asp Trp Ala Trp Val Gly Cys Ser Asn Leu
                805                 810                 815

Arg Gly Ser Leu Val Lys Leu Thr Thr Gly Arg Thr Gly Ala Asp Tyr
            820                 825                 830

Tyr Leu Glu Ile Thr Phe Thr Ser Gly Ala Gly Ser Leu Ala Pro Gly
        835                 840                 845

Ala Asn Ser Gly Asp Ile Gln Ala Arg Ile Asn Lys Asn Asp Trp Thr
    850                 855                 860

Asn Tyr Asn Glu Ala Asn Asp Tyr Ser Tyr Asp Pro Thr Lys Thr Ser
865                 870                 875                 880

Phe Ala Asp Trp Asn Arg Val Thr Leu Tyr Arg Asn Gly Gln Leu Val
                885                 890                 895

Trp Gly Val Glu Pro
            900
```

<210> SEQ ID NO 4
<211> LENGTH: 1002
<212> TYPE: PRT
<213> ORGANISM: Unknown
<220> FEATURE:
<223> OTHER INFORMATION: Enzyme identified in supernatant from a bacterial consortium

<400> SEQUENCE: 4

```
Met Thr Met Ala Trp Lys Gln Arg Ser Gly Leu Ile Ala Leu Ile Leu
1               5                   10                  15

Ala Leu Val Ala Gly Leu Leu Leu Pro Trp Gly Ser Leu Pro Lys Ala
            20                  25                  30

Ala Ala Glu Pro His Val Asp Asn Pro Phe Val Gly Ala Thr Ala Tyr
        35                  40                  45

Val Asn Pro Asp Tyr Ala Ala Leu Val Asp Ser Ser Ile Ala Arg Val
    50                  55                  60

Ser Asp Pro Thr Leu Ala Ala Lys Met Arg Thr Val Lys Thr Tyr Pro
65                  70                  75                  80

Thr Ala Val Trp Leu Asp Arg Ile Ala Ala Ile Asp Gly Gly Pro Gly
                85                  90                  95

Arg Arg Ser Leu Val Gln His Leu Asp Thr Ala Leu Ala Gln Lys Gln
            100                 105                 110

Gly Asn Thr Pro Ile Thr Ala Met Phe Val Ile Tyr Asn Met Pro Gly
        115                 120                 125

Arg Asp Cys Ala Ala Leu Ala Ser Asn Gly Glu Leu Pro Leu Thr Gln
    130                 135                 140

Glu Gly Leu Gln Arg Tyr Lys Thr Glu Tyr Ile Asp Arg Ile Ala Ala
145                 150                 155                 160

Ile Phe Ala Asp Pro Lys Tyr Ala Gly Ile Arg Ile Val Thr Val Ile
                165                 170                 175
```

-continued

```
Glu Pro Asp Gly Leu Pro Asn Leu Val Thr Asn Leu Ser Asp Pro Glu
            180                 185                 190

Cys Ala Gln Ala Asn Ser Ser Gly Ile Tyr Val Glu Ala Val Arg Tyr
        195                 200                 205

Ala Ile Asn Lys Leu Ser Glu Ile Pro Asn Val Tyr Ile Tyr Leu Asp
    210                 215                 220

Ile Ala His Ser Gly Trp Leu Gly Trp Asp Asn Asn Arg Thr Gly Ala
225                 230                 235                 240

Val Gln Leu Tyr Thr Asn Val Val Arg Gly Thr Thr Lys Gly Leu Ser
                245                 250                 255

Ser Val Asp Gly Phe Val Thr Asn Val Ala Asn Tyr Thr Pro Leu Glu
            260                 265                 270

Glu Pro Tyr Leu Thr Asp Pro Asn Leu Thr Val Gly Gly Gln Pro Leu
        275                 280                 285

Lys Ser Ala Lys Phe Tyr Glu Trp Asn Pro Tyr Phe Asp Glu Val Asp
    290                 295                 300

Tyr Ala Ala Ala Leu Arg Ser Ala Phe Ile Ser Ala Gly Trp Pro Thr
305                 310                 315                 320

Ser Ile Gly Met Leu Ile Asp Thr Ser Arg Asn Gly Trp Gly Gly Pro
                325                 330                 335

Asn Arg Pro Thr Gly Ala Ser Gly Thr Thr Val Asp Ala Tyr Val Asn
            340                 345                 350

Ser Gly Arg Val Asp Arg Arg Ala His Arg Gly Leu Trp Cys Asn Val
        355                 360                 365

Ser Gly Ala Gly Met Gly Met Pro Pro Gln Val Ala Pro Ala Ala Tyr
    370                 375                 380

Ala Ser Gln Gly Ile Glu Ala Phe Val Trp Val Lys Pro Pro Gly Glu
385                 390                 395                 400

Ser Asp Gly Ala Ser Ser Glu Ile Pro Asn Asp Glu Gly Lys Arg Phe
                405                 410                 415

Asp Arg Met Cys Asp Pro Thr Tyr Thr Thr Gln Tyr Gly Val Leu Thr
            420                 425                 430

Gly Ala Leu Pro Asn Ala Pro Leu Ala Gly Gln Trp Phe His Asp Gln
        435                 440                 445

Phe Val Met Leu Val Gln Asn Ala Tyr Pro Ala Ile Pro Thr Ser Gly
    450                 455                 460

Gly Gly Thr Pro Thr Pro Ser Thr Thr Val Thr Pro Thr Pro Thr Pro
465                 470                 475                 480

Thr Pro Thr Pro Thr Pro Ser Ala Thr Val Thr Pro Thr Pro Thr Pro
                485                 490                 495

Thr Pro Thr Pro Thr Pro Ser Ala Thr Val Thr Pro Thr Pro Thr Pro
            500                 505                 510

Thr Pro Thr Pro Thr Pro Thr Val Thr Pro Thr Pro Thr Ser Ser Thr
        515                 520                 525

Ser Phe Val Ala Arg His Gly Gln Leu Arg Val Val Gly Asn Gln Leu
    530                 535                 540

Val Asp Gln Asn Gly Gln Pro Ile Gln Leu Arg Gly Ile Ser Ser His
545                 550                 555                 560

Gly Leu Gln Trp Tyr Gly His Phe Val Asn Arg Asp Ser Leu Arg Trp
                565                 570                 575

Leu Arg Asp Asp Trp Gly Ile Thr Val Phe Arg Ala Ala Leu Tyr Thr
            580                 585                 590

Ala Glu Gln Gly Tyr Ile Thr Asn Pro Ser Leu Lys Glu Lys Val Lys
```

-continued

```
        595                 600                 605

Glu Ala Val Gln Ala Ala Ile Glu Leu Gly Ile Tyr Val Ile Ile Asp
    610                 615                 620

Trp His Ile Leu Ser Asp Gly Asp Pro Asn Thr Tyr Lys Glu Gln Ala
625                 630                 635                 640

Lys Ala Phe Phe Asp Glu Met Ser Arg Leu Tyr Gly Ser Tyr Pro Asn
                645                 650                 655

Val Ile Tyr Glu Ile Ala Asn Glu Pro Asn Gly Val Thr Trp Glu Gly
            660                 665                 670

Gln Val Lys Pro Tyr Ala Ser Glu Val Ile Pro Val Ile Arg Ala Asn
        675                 680                 685

Asp Pro Asp Asn Leu Ile Ile Val Gly Thr Thr Thr Trp Ser Gln Asp
    690                 695                 700

Val His Leu Ala Ala Asp Ser Pro Leu Pro Tyr Ser Asn Leu Ala Tyr
705                 710                 715                 720

Ala Leu His Phe Tyr Ala Gly Thr His Gly Gln Trp Leu Arg Asp Arg
                725                 730                 735

Ile Asp Tyr Ala Arg Asn Lys Gly Ile Ala Ile Phe Val Ser Glu Trp
            740                 745                 750

Gly Thr Ser Thr Ser Thr Gly Asp Gly Gly Pro Tyr Leu Thr Glu Ser
        755                 760                 765

Gln Gln Trp Leu Asp Phe Leu Asn Ala Arg Gln Ile Ser Trp Val Asn
    770                 775                 780

Trp Ser Leu Ser Asp Lys Ala Glu Ser Ser Ala Ala Leu Leu Pro Gly
785                 790                 795                 800

Ala Ser Ala Thr Gly Gly Trp Thr Asp Ala Gln Leu Ser Gln Ser Gly
                805                 810                 815

Arg Phe Val Arg Ala Gln Ile Arg Ser Gly Val Leu Thr Pro Thr Pro
            820                 825                 830

Thr Pro Thr Pro Thr Pro Thr Pro Ser Ala Ala Pro Thr Pro Thr Pro
        835                 840                 845

Thr Ala Gly Gly Ser Leu Val Val Gln Tyr Arg Ala Ala Asp Thr Asn
    850                 855                 860

Ala Gly Asp Asn Gln Leu Lys Pro His Phe Arg Ile Val Asn Arg Gly
865                 870                 875                 880

Thr Thr Ser Val Pro Leu Ser Glu Leu Ser Ile Arg Tyr Trp Tyr Thr
                885                 890                 895

Val Asp Gly Asp Lys Pro Gln Val Phe Asn Cys Asp Trp Ala Gln Val
            900                 905                 910

Gly Cys Ser Asn Leu Arg Gly Ser Phe Val Lys Leu Ser Thr Gly Arg
        915                 920                 925

Thr Gly Ala Asp Tyr Tyr Ile Glu Ile Thr Phe Thr Ser Gly Ala Gly
    930                 935                 940

Ser Leu Ala Ala Gly Gly Ser Ser Gly Asp Ile Gln Val Arg Ile Asn
945                 950                 955                 960

Lys Asn Asp Trp Thr Asn Tyr Asn Glu Ala Asn Asp Tyr Ser Tyr Asp
                965                 970                 975

Pro Thr Lys Thr Ser Phe Ala Asp Trp Asn Arg Val Thr Leu Tyr Arg
            980                 985                 990

Asn Gly Gln Leu Ile Trp Gly Val  Glu Pro
        995                 1000

<210> SEQ ID NO 5
```

<211> LENGTH: 683
<212> TYPE: PRT
<213> ORGANISM: Unknown
<220> FEATURE:
<223> OTHER INFORMATION: Enzyme identified in supernatant from a
      bacterial consortium

<400> SEQUENCE: 5

```
Met His Gln Ile Ala Glu Arg Arg Lys Met Ile Met Arg Asn Trp Leu
1               5                   10                  15

Gln Trp Gly Met Val Ala Ala Leu Leu Val Phe Thr Val Ser Val Val
            20                  25                  30

Pro Pro Lys Glu Ala Asp Ala Gly Leu Ala Lys Thr Lys Phe Leu Gly
        35                  40                  45

Asn Val Ile Asn Asn Ser Ile Pro Ser Asp Phe Ala Val Tyr Trp Asn
    50                  55                  60

Gln Val Thr Pro Glu Asn Ala Thr Lys Trp Gly Ser Val Glu Ser Ser
65                  70                  75                  80

Arg Asp Asn Met Asn Trp Ser Thr Ala Asp Met Ile Tyr Asn Tyr Ala
                85                  90                  95

Arg Ser Asn Gly Phe Pro Phe Lys Phe His Thr Leu Val Trp Gly Ser
            100                 105                 110

Gln Glu Pro Gly Trp Ile Ser Gly Leu Ser Ala Ala Glu Gln Gln Ala
        115                 120                 125

Glu Val Ile Glu Trp Ile Gln Ala Ala Gly Gln Arg Tyr Pro Asp Ala
    130                 135                 140

Asp Phe Val Asp Val Val Asn Glu Pro Leu His Ala Lys Pro Ser Tyr
145                 150                 155                 160

Arg Asn Ala Ile Gly Gly Asp Gly Ser Thr Gly Trp Asp Trp Val Ile
                165                 170                 175

Trp Ser Phe Glu Gln Ala Arg Arg Ala Phe Pro Asn Ser Lys Leu Leu
            180                 185                 190

Ile Asn Glu Tyr Gly Val Glu Asn Asp Pro Asn Ala Ala Ser Gln Tyr
        195                 200                 205

Val Gln Ile Ile Asn Leu Leu Lys Ser Arg Gly Leu Ile Asp Gly Ile
    210                 215                 220

Gly Ile Gln Gly His Tyr Phe Asn Leu Asp Thr Val Ser Val Ser Thr
225                 230                 235                 240

Leu Arg Thr Thr Leu Gly Met Leu Ala Glu Thr Gly Leu Pro Ile Tyr
                245                 250                 255

Val Ser Glu Leu Asp Ile Ser Gly Asp Asp Ala Thr Gln Leu Ala Arg
            260                 265                 270

Tyr Gln Glu Lys Phe Pro Ile Leu Trp Glu His Pro Ser Val Gln Gly
        275                 280                 285

Ile Thr Leu Trp Gly Tyr Ile Glu Gly Gln Thr Trp Arg Ser Gly Thr
    290                 295                 300

His Leu Ile Thr Ala Ser Gly Val Glu Arg Pro Ala Leu Gln Trp Leu
305                 310                 315                 320

Arg Thr Tyr Leu Ala Gly Ala Gly Ser Ser Pro Thr Pro Thr Pro Thr
                325                 330                 335

Pro Thr Pro Thr Val Thr Pro Thr Val Thr Pro Thr Pro Thr Pro Ser
            340                 345                 350

Ala Asn Gly Thr Leu Arg Val Glu Tyr Arg Val Gly Asp Ser Ser Ala
        355                 360                 365

Thr Asp Asn Gln Met Lys Pro Gln Leu Arg Ile Val Asn Thr Gly Ser
```

-continued

```
    370                 375                 380

Gln Ala Val Pro Leu Thr Glu Leu Lys Val Arg Tyr Trp Tyr Thr Lys
385                 390                 395                 400

Asn Ser Thr Gln Ala Glu Gln Tyr Phe Cys Asp Trp Ala Gln Ile Gly
                405                 410                 415

Cys Ser Asn Ile Arg Ala Gln Phe Val Ser Leu Ser Gln Pro Val Ser
            420                 425                 430

Gly Ala Asp Ser Tyr Ile Glu Leu Ser Phe Thr Gly Gly Ser Ile Pro
        435                 440                 445

Ala Gly Gly Asn Thr Gly Glu Ile Gln Asn Arg Ile His Phe Thr Asn
    450                 455                 460

Trp Met Asn Tyr Asn Glu Thr Asp Asp Trp Ser Tyr Asn Gly Ala Gln
465                 470                 475                 480

Thr Thr Trp Gly Pro Ser Thr Arg Ile Thr Leu Tyr Arg Asn Gly Val
                485                 490                 495

Leu Val Trp Gly Thr Glu Pro Gly Gly Ser Ser Thr Pro Thr Pro Thr
            500                 505                 510

Pro Thr Pro Thr Pro Thr Pro Thr Pro Ser Ala Ala Pro Thr Pro Ala
        515                 520                 525

Pro Ser Ala Gly Gly Ser Leu Val Val Gln Tyr Arg Ala Ala Asp Thr
    530                 535                 540

Asn Ala Thr Asp Asn Gln Leu Lys Pro His Phe Arg Ile Val Asn Arg
545                 550                 555                 560

Gly Thr Thr Ser Val Pro Leu Ser Glu Leu Thr Ile Arg Tyr Trp Tyr
                565                 570                 575

Thr Val Asp Gly Asp Lys Pro Gln Val Phe Asn Cys Asp Trp Ala Gln
            580                 585                 590

Val Gly Cys Ser Asn Val Arg Gly Ser Phe Val Lys Leu Ser Thr Gly
        595                 600                 605

Arg Thr Gly Ala Asp Tyr Tyr Ile Glu Ile Thr Phe Thr Ser Gly Ala
    610                 615                 620

Gly Ser Leu Ala Pro Gly Ala Asn Ser Gly Asp Ile Gln Ala Arg Ile
625                 630                 635                 640

Asn Lys Asn Asp Trp Thr Asn Tyr Asn Glu Ala Asn Asp Tyr Ser Tyr
                645                 650                 655

Asp Pro Thr Lys Thr Ser Phe Ala Asp Trp Asn Arg Val Thr Leu Tyr
            660                 665                 670

Arg Asn Gly Gln Leu Ile Trp Gly Val Glu Pro
        675                 680


<210> SEQ ID NO 6
<211> LENGTH: 651
<212> TYPE: PRT
<213> ORGANISM: Unknown
<220> FEATURE:
<223> OTHER INFORMATION: Enzyme identified in supernatant from a
      bacterial consortium

<400> SEQUENCE: 6

Met Asn Arg Arg Leu Ile Ala Arg Leu Ser Gly Met Leu Ala Met Val
1               5                   10                  15

Leu Ile Ala Ala Val Leu Ala Tyr Val Pro Lys Pro Glu Pro Ala Glu
            20                  25                  30

Ala His Gly Gly Met Val Phe Pro Ala Thr Arg Thr Tyr Ala Cys Tyr
        35                  40                  45
```

-continued

```
Val Asp Gly Lys Val His Gly Asn Gly Gly Asp Leu Asn Met Ile Asn
    50                  55                  60

Pro Ala Cys Leu Asp Ala Leu Ala Ile Ser Gly Asn Tyr Gln Phe Trp
65                  70                  75                  80

Asn Trp Phe Gly Asn Leu Ile Ser Asn Ala Gly Gly Arg His Arg Glu
                85                  90                  95

Ile Ile Pro Asp Gly Lys Leu Cys Gly Pro Thr Ala Ser Phe Asp Gly
            100                 105                 110

Met Asn Gln Ala Arg Thr Asp Trp Trp Thr Thr Arg Leu Gln Pro Gly
        115                 120                 125

Ala Thr Ile Thr Val Arg Val Asn Ala Trp Ala Pro His Pro Gly Thr
    130                 135                 140

Trp Tyr Leu Tyr Val Thr Arg Asp Gly Trp Asp Pro Thr Gln Pro Leu
145                 150                 155                 160

Lys Trp Ser Asp Leu Glu Pro Thr Pro Phe Ser Gln Val Thr Asn Pro
                165                 170                 175

Pro Ile Asn Ser Ser Gly Pro Asp Gly Ala Glu Tyr Ser Trp Gln Val
            180                 185                 190

Gln Leu Pro Asn Lys Gln Gly Arg His Ile Ile Tyr Met Ile Trp Gln
        195                 200                 205

Arg Ser Asp Ser Pro Glu Ala Phe Tyr Asn Cys Ser Asp Ala Tyr Phe
    210                 215                 220

Gly Ser Gly Pro Ile Ala Tyr Glu Phe Gly Asp Pro Arg Glu Gly Gly
225                 230                 235                 240

Thr Met Ile Thr Pro Pro Pro Ser Gly Thr Thr Pro Thr Pro Thr Pro
                245                 250                 255

Thr Pro Thr Pro Thr Pro Thr Pro Thr Leu Thr Pro Thr Pro Thr Pro
            260                 265                 270

Thr Pro Thr Pro Thr Pro Thr Pro Thr Leu Thr Pro Thr Pro Thr Pro
        275                 280                 285

Thr Pro Thr Pro Thr Ser Thr Pro Thr Ser Thr Pro Thr Ser Thr Pro
    290                 295                 300

Thr Pro Thr Pro Thr Pro Ser Ala Ser Gly Thr Leu Arg Val Glu Tyr
305                 310                 315                 320

Arg Val Gly Asp Ser Ser Ala Thr Asp Asn Gln Met Lys Pro Gln Leu
                325                 330                 335

Arg Ile Val Asn Thr Gly Ser Gln Ala Val Pro Leu Thr Glu Leu Lys
            340                 345                 350

Met Arg Tyr Trp Tyr Thr Lys Asn Ser Thr Gln Ala Glu Gln Tyr Phe
        355                 360                 365

Cys Asp Trp Ala Gln Ile Gly Cys Ser Asn Ile Arg Ala Gln Phe Val
    370                 375                 380

Ser Leu Ser Gln Pro Val Ser Gly Ala Asp Ser Tyr Ile Glu Leu Ser
385                 390                 395                 400

Phe Thr Gly Gly Ser Ile Pro Ala Gly Gly Asn Thr Gly Glu Ile Gln
                405                 410                 415

Asn Arg Ile His Phe Thr Asn Trp Met Asn Tyr Asn Glu Thr Asp Asp
            420                 425                 430

Trp Ser Tyr Asn Gly Ala Gln Met Thr Trp Gly Pro Ser Thr Arg Ile
        435                 440                 445

Thr Leu Tyr Arg Asn Gly Val Leu Val Trp Gly Thr Glu Pro Gly Gly
    450                 455                 460

Gly Ser Ser Pro Pro Thr Pro Thr Val Thr Pro Thr Pro Thr Pro Thr
```

-continued

```
465                 470                 475                 480

Ser Thr Pro Thr Pro Thr Pro Thr Pro Ser Ala Ala Pro Thr Pro Thr
                485                 490                 495

Pro Ser Ala Gly Gly Ser Leu Val Val Gln Tyr Arg Ala Ala Asp Thr
            500                 505                 510

Asn Ala Gly Asp Asn Gln Leu Lys Pro His Phe Arg Ile Val Asn Arg
        515                 520                 525

Gly Thr Thr Ser Val Pro Leu Ser Glu Leu Ser Ile Arg Tyr Trp Tyr
    530                 535                 540

Thr Val Asp Gly Asp Lys Pro Gln Val Phe Asn Cys Asp Trp Ala Gln
545                 550                 555                 560

Val Gly Cys Ser Asn Leu Arg Gly Ser Phe Val Lys Leu Ser Thr Gly
                565                 570                 575

Arg Thr Gly Ala Asp Tyr Tyr Ile Glu Ile Thr Phe Thr Ser Gly Ala
            580                 585                 590

Gly Ser Leu Ala Pro Gly Ala Ser Ser Gly Asp Ile Gln Val Arg Ile
        595                 600                 605

Asn Lys Asn Asp Trp Thr Asn Tyr Asn Glu Ala Asn Asp Tyr Ser Tyr
    610                 615                 620

Asp Pro Thr Lys Thr Ser Phe Ala Asp Trp Asn Arg Val Thr Leu Tyr
625                 630                 635                 640

Arg Asn Gly Gln Leu Val Trp Gly Val Glu Pro
                645                 650
```

<210> SEQ ID NO 7
<211> LENGTH: 16571
<212> TYPE: DNA
<213> ORGANISM: Unknown
<220> FEATURE:
<223> OTHER INFORMATION: Nucleotide sequence of combined contigs encoding identified enzymes obtained from the metgenome from a bacterial consortium

<400> SEQUENCE: 7

```
ttgaaggagg aacagacggt gaatttccga caactgatgc tgagacgacg ggcgctgtcg     60

atgttgacgg gcgcggcggt cgtttattcg gctttcgtgc cggttggaag tccggattcg    120

gctgttgttc gggcggctcc tacctcttac aattacgcgg aagcgcttca aaaggcaatt    180

tatttctacg acgcacaacg ttccggcaag ctgcctcccg ataaccgcgt cgaatggcgc    240

ggcgattccg ggcttaacga cggagccgac gtcggcgtcg atttgacggg cggttggtac    300

gacgccggcg accacgtcaa gttcgggttg ccgatggcat attccgccgc catgctggcg    360

tgggcggtgt acgagtaccg cgacgctttc gtgcagacgg ggcagctcga ttatattttg    420

aacaacatca agtgggcgac cgactatttc atcaaggcgc attccgcgcc caacgtgctt    480

tggggacagg tcggcaaggg ggacgtcgat catgcctggt ggggaccggc agaagtgatg    540

cagatgccgc gtccggccta caaaatcgac ccgagctgtc cggggtccga tctcgctgcc    600

ggaacggccg ccgcgatggc cgccgccgcc gcggtgttta aacccactga cccgacttat    660

gcctcaacgt tgatcgctca tgcgaaacaa ttgtatacgt ttgcagatac ttatcggggg    720

aaatattccg attgcatcac tgatgcgcaa aatttctatc ggtcgtggag cggttacgcc    780

gatgagctga cgtggggtgc cgtctggctt tatctcgcca ccggcgagca ggcctatctt    840

gacaaggcaa tcgcctcagt cgcggaatgg gggcgcgaag gtcagacgcc ttattggggt    900

tacaaatgga cgcaaagctg ggacgacgtc cattacggcg ctcagctgct gttggcaaga    960
```

-continued attacgggcg accagcggtt tatccagtcg acggagcgca acctggaata ttggacggac 1020
ggcacggacg acaccggcga gcgcatcacg tatacgcccg gggggcttgc ttggctagat 1080
tcttggggtt cactccgcta tgcgatgaac gcgtcgttct tggcgttcgt ctattccgac 1140
tggctgcaaa gccgcgatcc cgccaaagcg gaaaagtaca ggaacttcgc cgttcgccag 1200
gttctgtatg cattgggcga caacccgcgc aattctagct atgtcgtcgg attcgggcgc 1260
aatccgccgc agcggccgca tcaccggacg gcgcacgggt cgtgggctga cagccagaac 1320
gttcccgctt accatcggca cattttatat ggcgctcttg tgggcggtcc gaaccagtcc 1380
gacgcctata cggattcgat cagcgactac gtcggcaatg aggttgcgac ggattacaac 1440
gcggcgttta cgggaaatct cgcaaaaatg tatctgctgt tcggcgccag cgccggacag 1500
cggccgcttg ccaattttcc cgagccggaa gtacgcgagg acgagttttt cgtcgaagcc 1560
ggcgtgaaca gctccggacc gaactacaca gagatcaagg ccctgatcaa caaccggtcc 1620
ggctggcccg cgcggatggg cgacaagctt tcgttcaagt atttcgtcga tttgtctgaa 1680
gtttacgccg ccggttatac ggtcaacgac attaaggtga cgacgaacta caacgaaggc 1740
gcgaaagtat ccggtctgct tccgtatgac gaaagccgtc gtctttacta tgtgctcgtc 1800
gattttacgg gtacgaagat ttatcccggc ggtcagtccg cctacaagaa agaggttcag 1860
ttcagactga gcgctccgag cgggacatcg ttctggaatc cgaacaacga tttctcgtac 1920
cagctgatgt ccggcacgtc caacagcagc ctggtcaaga cgccgtatat gccggtttat 1980
gacgccgggg tgaagatttt cggcgtggag ccgtcgtccg gaagcgggtc gagcccgacg 2040
ccgccaccca cgtcgacgcc gacaccgaca ccgacgccga caccgacacc gacgctgaca 2100
ctgacaccga caccgacgcc gacaccgacg ccgacaccga cgccgacacc gacgccgaca 2160
ccgacaccga cgccgacacc aacgccgaca ccaacgccga caccgacgcc gacgccgaca 2220
ccaacgccga cgccgacacc gacaccgacg cctagcgcga gcggtaccct gcgcgtcgag 2280
tatcgcgtcg gtgacaccag cgccaccgac aaccagatga agccgtacct gcgcatcgtc 2340
aacaccggct cgcaagccgt gccgctgacc gaactgaagg tgcgctactg gtacacgaag 2400
aactcgacgc aggccgaaca gtacttctgc gactgggcgc agatcgactg ctcgaacatc 2460
cgggcgcagt tcgtgtcgct ggcgcagccg gtcagtggag cggacagcta catcgagctg 2520
agcttcacgg gcggaagcgt tccggcggga ggcaacacgg gcgagataca gaaccggatt 2580
cacttcacga actggatgaa ctacaacgaa acggacgact ggtcgtacaa cgggacgcag 2640
acgacgtggg gtccgtcgac gcggattacg ctgtatcgta acggcgtgct ggtgtggggc 2700
accgagccgg gcggcggatc gtcgacgccg acaccgacgg cgacacctac gcctacgccg 2760
agcgcggcgc ccacaccgac gccgacggcc ggcggcagcc tggtcgtgca gtatcgcgcg 2820
gcggacacga acgcgggcga caaccagctg aagccgcact ttaggattgt gaaccgcggg 2880
acgacgagcg tgccgctgtc ggagctttcg atccggtact ggtacacggt ggacggggac 2940
aagccgcagg tgttcaactg cgactgggcg caggtgggtt gttcgaactt gcggggcagt 3000
ttcgtgaagc tttcgacggg ccggacgggg gcggactact acatcgagat cacgttcaca 3060
tcgggcgcgg gcagcttggc ggctggggga agcagtgggg acattcaggt gcggatcaac 3120
aagaacgact ggacgaacta caacgaggcg aacgattact cgtatgatcc gacgaagacg 3180
agttttgcgg attggaaccg ggtgacgctg tatcgcaacg gtcagctcat ctggggcgtc 3240
gaaccatagc aaaattcggt ggtttattct tttgaacagc aaaccccagg gaacggagga 3300
atgagggtgt cgatcgaatt ggcaatccta ttgccgacct tcgttccctg gtttgcaaat 3360

-continued agaaacgcta caaaaaacag gaggaagagg gaaaatcatg gaatcactcg catggacgct 3420
gttatggaag aaagcaagaa ttatctttct tgctttcgcg cttgtcgtct ccgccttcgc 3480
gggcttcgct gtgtctcctc gtagcgaaac cgcttacgcg cagacggacc cgcaggtttt 3540
caaggacagg tttttgcagc tgtacaacca aatcaaaaat ccggcgaacg gttacttttc 3600
gccggaaggc attccttatc actccatcga aacgttgatt tcggaagctc ccgactatgg 3660
gcatatgacg acgtcggaag cgttcagtta ttggctctgg ctggaaacgc tatatggtta 3720
cttcaccggt gactggtcga aactggaaca ggcttggaca aaaatggagc aattcattat 3780
cccgaactcg acggaacagc cgacgatggg gtcttacaac ccatcaagtc cagctactta 3840
cgcgccggaa catccgtatc cggaccggta tccaactttg ctgaacaatt ccgtgccggc 3900
aggacaggac ccactggatg cggaactcaa agcgacgtac ggtaataacg tgacgtattt 3960
gatgcactgg ctgcttgacg tggacaattg gtacggcttc ggcaacctgt tgaacccgtc 4020
gcatacggcg acctacgtca acacgttcca gcgcggcgaa caggaatcgg tctgggaggc 4080
gatcacacat ccgtcgcagg acaatttccg gttcggaaaa ccgaatgaag gttttgtgac 4140
gctgttcgta aaagataacg gaacgcctgc ccagcaatgg cgttatacgg cagcctctga 4200
cgccgacgca cgcgccattc aggtgatgta ttgggcgaag cagctggggt acaacaacca 4260
gacctatctg gataaggcgc gcaagatggg cgactatctg cgctatacac tgttcgacaa 4320
gtatttccaa caaatcggca gtgcaaacga cggttctccg agcccgggca gcggtaaaaa 4380
ctctgcgcat taccttttgt cttggtacac ggcctggggc ggtggtctcg gctccggcgg 4440
caactgggct tggagaatcg gatcgagcca tgctcatcag ggttatcaaa atcctgtcgc 4500
tgcttatgcg ctgtctgccg gcggactggc gccgcgttcc gcaacggcac agaccgactg 4560
ggcgacgtcg ttgcaacgtc agcttgaatt ctatacgtgg ctgcaatcga gcgaaggcgc 4620
catcggcggc ggggcgacca acagcgtcgg gggcagctat cagccgtatc cttccggtcg 4680
cagtacgttc tacggcatgg tttacgatga agcgccggtt tatcgcgatc cgccttcgaa 4740
ctcgtggttc ggcttccaag cgtggtccgt cgaacgcgtc gcggaactgt actatatctg 4800
gaccagcagc ggaaatacca atacgcagca gttccagatg gttaaaaaca tcgtcaccaa 4860
atgggtcgat tgggcgcttg actatacgtt cgtgaatcaa cgcccggtta cagacgctca 4920
agggtatttc ctgacgagca gcggcagccg tgtcctgggc ggcaacaatc cgcagatcgc 4980
cacggtttcc gatcccggtc agttctatat tccgtcgacg ctggaatggc agggtcaacc 5040
ggacacatgg aacggatatg ccaattatac gggcaatccc aatttccatg cgattgcgaa 5100
agaccccggc caagacgtcg gcgtcaccgg caactatatc aagctgctga cgttctttgc 5160
cgcggccacg aaagcggaga cggggaacta caccgctctc ggaagccagg cgttgaatgt 5220
cgccgaacag ttgctgaacg tgctttggaa tttcaacgac ggggttggga ttgtccgtcc 5280
cgaacaacgc gccgactact tccgctattt tacgaaggaa atttacttcc cgagcggctg 5340
gagcggcacg tacggacagg gcaataccat tcctgggccg ggcgcggttc cttccgatcc 5400
gtcgaaaggc ggaaacggcg tttatatcag ctacgccgaa ctgcgtccga agatcaagca 5460
agatccgaaa tggtcgtatc ttgaaaatct gtacaaaact tcgtataatc cgtccacagg 5520
tcgctgggaa aacggtgttc cgacgttcac gtatcaccgt ttctgggcgc aggtcgatgt 5580
ggcgacggcg tatgcggaat ttgcccggtt gatcggcggt ttgggcgctt cgccgacacc 5640
gacgccgagc gcgacaccga cgccgacacc gtcggccggc ggcaacctgg tcgtgcagta 5700

-continued

```
ccgcgcggcg gacacgaacg cgacggacaa ccagctgaag ccgcacttta ggattgtgaa   5760
ccgcgggacg acgagcgtgc cgttgtcgga gctgacgatc cggtactggt acacggtgga   5820
cggagacaag ccgcaggtgt tcaactgcga ctgggcgcag gtaggttgct cgaatgtgcg   5880
tggcagcttt gtgaagctga cgacgggccg gacgggggcg gactactaca tcgagatcac   5940
gttcacgtcg ggcgcgggca gcttggcggc tgggggaagc agtggggaca ttcaggtgcg   6000
gatcaacaag aacgactgga cgaactacaa cgaggcgaac gactactcgt gtgatccgac   6060
gaagacgagt tttgcggatt ggaaccgagt gacgctgtat cgtaacggtc agctcgtctg   6120
gggcgtcgaa ccgtaacgca caacagtcca tgccgagaag gttcgggggc gttcaactga   6180
agacggggaa cgcccccgtt cctgaaagta tgtcacgagc aaaacgaggg aggagccgag   6240
catgggaacg ggccgtgccg gagagtggat caaaaaaatg ttgctggttt tggcaattgg   6300
attgctcctt ccgattccat acctgcatgt cgcttcagcg gaaaacgtcc tgattttgca   6360
gagcgatttt gaggacggga cgacgcaagg gtgggtcggt cgcgggggag tcgaaacgct   6420
tactgtcact tccgcggcag cgtacagcgg agcttatggt ttgtccgtga gcggaagaac   6480
gaaaacgtgg catggtccga cattggacat cacttcctat attcaggttg gaaagactta   6540
tcaattttca gcatgggtta aattgccttc cggttcgtcc aacacacgca tttatatgac   6600
gatgcaaaga accatgcagg acacggtcta ctatgagcaa atttatttcg acacggcttc   6660
agctggaaat tgggttcaat tgaaagccca atacaagttg tacgaacctg ctgtaaacct   6720
gcaggtatac tttgaagctc ccgatcatgc tactcaatct ttctatattg atgacgtccg   6780
aattgaacaa cttcctgatc ttccgaagac ggtagaagag aatattccgt ccctgaaaga   6840
tgttttcgca gggcgttttc cgataggaac ggcgtttgaa aattttgaac ttctcgatga   6900
acaggacaga aaattgattt taaaacattt caatagtgtg acgcctggaa acgtgctgaa   6960
gtgggacagc acagaaccac aagaaggagt ctttaacttt acggaatcgg ataaagcggt   7020
tgcttttgcg gttcagaacg gaatgaagat cagaggtcat acattgattt ggcataatca   7080
gacgccgaat tgggtgtttt atgattcaaa cggaaattta gtttccaaag aagttctata   7140
tcaacgaatg gaaagacaca ttaaacccgt cgtcagccgc tacaaaggaa tcatctatgc   7200
gtgggatgtc gtcaatgaag ttatcgatcc cggacagcct gatggattgc gtagaagctt   7260
gtggtatcag attgccggcg aggagtatat cgaaaaggcg ttccaatttg cgcatgaagc   7320
tgatccgaat gcgcttctct tcatcaatga ttataacacg catgaatccg gtaaaagcca   7380
agcattgtac aatttggtac aacgactgaa aaataagggt attcctgttc acggagtcgg   7440
acaccagacc catattaata tttcctggcc gtcgatcagt gaaatcgaaa attcgctcgt   7500
caagttctcg aacctgggag ttgttcagga aatcactgag ttggatatga gcatttacaa   7560
caattcatca cagaagtacg acacattgcc ttccgatttg gctcagcagc aggcaacccg   7620
ttacagacaa ctgttcgaaa tgttcttgag aaggagcagt ttgattcaaa acgttacgtt   7680
ctggggcaaa gatgatgcaa atacgtggtt gcggaagttc ccagtcgtcc gaaatgactg   7740
gccgctgttg ttcgatgagc aattaaaggc gaaaccggca tattgggcgg tagtcggaac   7800
tgttccgtca cccacgccga caccgacgtc gacggcaaca ccaacgccga caccaacggt   7860
gataccgacg ccgacaccga cgccaacgcc gacatcgacg ccgacaccga cgccgacgtc   7920
gacgccgacg cctagcgcga gcggcaccct gcgcgtcgag tatcgcgtgg gcgattccag   7980
cgccaccgac aaccagatga aaccgcagct gcgcatcgtc aacaccggct cgcaagccgt   8040
gccgctgacc gaactgaaag tgcgctactg gtacacgaag aactcgacgc aggccgaaca   8100
```

-continued

```
gtacttctgc gactgggcgc aaatcggctg ctcgaacatc cgggcgcagt tcgtgtcgct   8160

ggcgcagcca gtcagcggag cggacagcta catcgagctg agcttcacgg ggggcagcgt   8220

tccggcggga ggcaacacgg gcgagatcca gaaccggatt cacttcacga actggatgaa   8280

ctacaacgaa acggacgact ggtcgtacaa cgggacgcag acgacgtggg ggccgtcgac   8340

gcggattacg ctgtatcgta acggcgtgct ggtgtggggc accgagccgg gcggcggatc   8400

gccgacaccg acaccaacgc cgacgtcaac gccgacgccg acgtcaacgc cgacaccgac   8460

gccgacgccg acaccgacac cgacggcgac accgacaccc acacccacgc cgacgccgtc   8520

ggccggcggc aacctggtcg tgcagtaccg cgcggcggac acgaacgcgg gcgacaacca   8580

gctgaagccg cattttcgga ttgtgaaccg cgggacgacg agcgtaccgt tgtcggagct   8640

tacgattcgg tactggtaca cggtggacgg cgacaagccg caggtgttca actgtgactg   8700

ggcgtgggtc ggatgttcga acctgcgcgg cagtctggtg aagttgacga cgggccggac   8760

gggggcggac tactaccttg agatcacgtt cacatcgggc gcgggcagcc tggcgcctgg   8820

ggcgaacagc ggagacattc aggcgcggat caacaagaac gactggacga actacaacga   8880

ggcgaacgac tactcgtatg atccgacgaa gacgagtttt gcggattgga accgggtgac   8940

gctgtatcgg aatggtcagc tcgtctgggg cgtcgagccg taagggtata cctaagagcg   9000

gcgtggcgga gtcgataagc ggtgatgatt ccgcctcgct cgaggaccgg tcgactgcca   9060

cagaaggctt tgtgaaggag gtgatggacg gaagatccga aaaagaaaga atatgaaggt   9120

tttgtgggtt ggttttggta aaaaagaatc catgaggaac caaacgaaag aggggagtga   9180

cacaggcatg acgatggcgt ggaaacagcg cagcggattg atcgcgttga ttttggcatt   9240

ggtagcgggt ttgctgctgc catggggatc gctgccgaaa gcggcggcgg agccgcatgt   9300

ggacaatccg tttgtaggag cgacggctta cgtcaatccg gactatgcgg cgctggtcga   9360

ttcgtcgatc gcgagggtga gcgatccaac gctggcggcg aagatgcgta cggtcaagac   9420

gtatccgacg gcggtgtggt tggatcggat cgcggcgatt gacggagggc cgggaagacg   9480

gagcttggtg cagcatttgg atacggcgtt ggcgcagaag caagggaata cgccgattac   9540

ggcgatgttt gtgatttaca atatgccggg tcgggactgc gcggcgctgg cgtcgaacgg   9600

ggagctgccg ctgacgcagg aagggctgca gaggtacaag acggagtata ttgaccgaat   9660

tgcggcaatt tttgcagatc cgaagtatgc gggaattcgg atcgtgacgg tgattgaacc   9720

ggacggcttg ccgaacctgg tgacgaacct gagcgatccg gaatgcgcgc aggcgaattc   9780

aagcggaatt tatgtagagg cagtacgata tgcgatcaac aagttgagcg aaattccgaa   9840

cgtgtatatt tacctggaca tcgcgcattc gggatggctg ggctgggaca acaaccggac   9900

cggcgcggtg cagctgtata cgaacgtggt gcgagggacg acgaaagggc tttcgagcgt   9960

ggacgggttt gtgacgaacg tggcgaacta tacgccgctc gaggagccgt atttgacgga  10020

tccaaacctg acggtgggag gtcagccgct taagtcagcg aagttttatg agtggaaccc  10080

gtattttgat gaagtagatt atgcggcagc gttgcggtcg gcgtttatca gtgcagggtg  10140

gccgacgagc atcgggatgt tgatcgacac gagccgcaac ggctggggcg ggccgaaccg  10200

gccgacggga gcgagcggga cgacggtgga cgcgtatgtg aattcggggc gtgtggaccg  10260

tcgggcgcat cgcgggctgt ggtgtaacgt cagcggagcg gggatgggaa tgccgccgca  10320

ggtggcgccg gcggcgtatg cgtcgcaagg gatcgaggca ttcgtatggg tgaagccgcc  10380

cggggagtcg gacggagcga gttcggagat accgaacgac gaaggcaagc ggtttgaccg  10440
```

-continued

```
gatgtgcgat ccgacgtata cgacgcaata cggggtgttg acgggggcgt tgccgaacgc  10500
gccgttggcg gggcaatggt tccatgatca gtttgtgatg ttggtgcaga atgcgtatcc  10560
ggcgattccg acgagcggcg gtgggacacc gacgccgagt acgacggtga cgccgacacc  10620
gacaccgacg ccgacaccga cgccgagtgc gacggtgacg ccgacaccga caccgacgcc  10680
gacaccgacg ccgagtgcga cggtgacgcc gacaccgaca ccgacgccga caccgacgcc  10740
gacggtgacg ccgacgccga catcgtcgac aagttttgtg gccaggcacg ggcaattgag  10800
agtcgtgggg aatcaattgg tcgaccaaaa tggacaaccc atccaactaa gaggcattag  10860
ttctcatggg ttacaatggt atgggcattt cgtcaatcga gacagcctcc gatggctccg  10920
agatgattgg ggaataacag ttttccgagc agctctgtat actgccgaac aaggatatat  10980
cacgaatccg tctttaaaag aaaaagtgaa ggaagctgta caagccgcaa ttgaactcgg  11040
tatttatgtg atcatcgact ggcacatttt gtctgatggc gatccgaaca cgtacaagga  11100
gcaagcgaaa gcgtttttcg atgaaatgtc gcgattgtac ggcagttatc cgaacgtgat  11160
ttatgagatc gccaacgaac cgaatggtgt gacatgggaa ggacaggtta agccgtacgc  11220
ttcggaggtg atcccggtca tccgtgctaa tgaccctgat aatctcatta ttgtcggaac  11280
aacaacgtgg agtcaggatg tccatcttgc agcagatagc ccgctacctt acagcaacct  11340
ggcgtacgct ctgcatttct atgccggtac gcatggtcaa tggttgagag accggatcga  11400
ctatgcgagg aataaaggca tcgcgatttt cgtgagtgaa tgggggacaa gcacttcgac  11460
aggcgatgga ggcccctatc tcacggagtc gcaacaatgg ttggatttcc ttaatgctcg  11520
gcagatcagt tgggtgaact ggtcgttgag cgacaaggcc gagtcatccg cagcattgtt  11580
gcctggcgca agcgcaacag gtggttggac ggacgcacaa ttgtctcagt cggggcgttt  11640
tgttcgcgct cagattcgca gcggtgtatt gacgccgaca ccgacgccga cacctacgcc  11700
tacgccgagt gcggcgccca caccgacgcc gacggccggc ggcagcctgg tcgtgcagta  11760
tcgcgcggcg gacacgaacg cgggcgacaa ccagctgaag ccgcattttc ggattgtgaa  11820
ccgcgggacg acgagcgtgc cgctgtcgga gctttcgatc cggtactggt acacggtgga  11880
cggagacaag ccgcaggtgt tcaactgcga ctgggcgcag gtgggttgtt cgaacttgcg  11940
gggcagtttc gtgaagcttt cgacgggccg gacgggggcg gactactaca ttgagatcac  12000
gttcacgtcg ggcgcgggca gcttggcggc tgggggaagc agcggggaca ttcaggtgcg  12060
gatcaacaag aacgactgga cgaactacaa tgaggcgaac gactactcgt atgatccgac  12120
gaagacgagt tttgcggatt ggaaccgggt gacgctgtat cgcaacggtc agctcatctg  12180
gggcgtcgag ccttgattgc caaccgacgg tatggacctg gcggacggta agtccgttcg  12240
ccaggttcct ataaaaacaa catctccgct cgaaaaaacc ttgaaggaag ggagaggatt  12300
ttttatgaat cgacgcctta tcgcccgcct cagcggcatg ttggcgatgg ttctcatcgc  12360
cgcagtgttg gcgtacgttc cgaagcctga accggccgag gcgcacggag gtatggtgtt  12420
tccagccacg cgaacgtatg cctgttatgt tgacggcaag gttcacggca atggcggaga  12480
cttgaacatg atcaatccgg cgtgtcttga tgccttggcg atctcgggca actatcagtt  12540
ctggaactgg ttcggaaatc tgatcagtaa tgccggagga cgccataggg aaatcattcc  12600
tgacggcaaa ctgtgcggac caacggccag ttttgatggt atgaaccagg cgcgtacaga  12660
ctggtggacg actcgtctgc agccgggcgc aacgattacg gtgcgagtca acgcatgggc  12720
gccgcatccc ggcacgtggt atttgtatgt aacccgggac ggatgggatc cgacacaacc  12780
gctgaaatgg tcggatctgg aaccgacgcc cttcagccag gtgactaatc cgccgatcaa  12840
```

-continued ctcgagcgga ccggacgggg ccgagtacag ctggcaggtg cagctgccga acaagcaagg 12900
gcgacacatc atttatatga tatggcagag atccgacagt ccggaggcat tttacaactg 12960
ttcggatgcg tatttcggat cggggccgat tgcttatgaa tttggtgacc cgcgggaagg 13020
aggaacgatg attacgccgc cgccgtcggg cacgacgccg acaccgacgc cgacaccgac 13080
gccgacaccg acgccgacac tgacgccgac accgacgccg acaccgacgc cgacaccgac 13140
gccgacactg acgccgacac cgacgccgac accgacgccg acatcgacgc cgacgtcgac 13200
accgacgtcg acgccgacac cgacaccgac gcctagcgcg agcggcaccc tgcgtgtcga 13260
gtatcgcgtg ggcgattcca gcgccaccga caaccagatg aaaccgcagc tgcgcatcgt 13320
caacaccggc tcgcaagccg tgccgctgac cgagctgaag atgcgctact ggtacacgaa 13380
gaactcgacg caggccgaac aatacttctg cgactgggcg cagatcggct gctcgaacat 13440
ccgggcgcag ttcgtgtcgc tgtcgcagcc ggtcagcggg gcggacagct acatcgagct 13500
gagctttacg ggcggaagca ttccggcggg aggcaacacg ggcgagattc agaaccggat 13560
tcacttcacg aactggatga actacaacga aacggacgac tggtcgtaca acggggcgca 13620
gatgacgtgg gggccgtcga cgcggattac gctttatcgc aacggcgtgc tggtgtgggg 13680
cacggagccg ggcggcggat cgtcgccgcc gacgccgacg gtgacaccga cacctacacc 13740
gacatcgacg ccgacaccta cgcctacgcc gagtgcggcg cccacaccga cgccgtcggc 13800
cggcggcagc ctagtcgtgc agtatcgcgc ggcggacacg aacgcgggcg acaaccagct 13860
gaagccgcat tttcggattg tgaaccgcgg gacgacgagc gtgccgctgt cggagctttc 13920
gatccggtac tggtacacgg tggacgggga caagccgcag gtgttcaact gcgactgggc 13980
gcaggtgggt tgttcgaact tgcggggcag cttcgtgaag ctttcgacgg gccggacggg 14040
ggcggactac tacatcgaga tcacgtttac gtcgggcgcg ggcagtctgg cgcctggggc 14100
gagcagcgga gacattcagg tgcggatcaa caagaacgac tggacgaact acaacgaggc 14160
gaacgactac tcgtatgacc cgacgaagac gagttttgcg gattggaacc gggtgacgct 14220
gtatcggaat ggtcagctcg tctggggcgt tgaaccataa taacggcaag cacaactcgg 14280
ccaggtcgtt tctccaaagc ccttctttcg gaagtatcga aagaagggct ttccttctaa 14340
actttttcgg ggtgacatct aaagtttatc ccgtactcga aggatcgaga gaaacgatag 14400
aataggcaat aagttactgt aaatcttgta tgaacagaaa ggagatgatt acaaaaggac 14460
ggattcatcg tttttttcg aaaaggtcgg cagtaggtct gtttgagacg ggatcacaca 14520
tgcatcaaat tgcagagagg aggaaaatga taatgcgaaa ctggctccaa tggggcatgg 14580
ttgcggcttt gctcgttttt acggtatcgg tcgtcccccc gaaagaagcc gatgcagggc 14640
tagccaagac aaaattcttg gggaatgtca tcaacaatag catcccttct gattttgctg 14700
tttactggaa tcaggttacc cctgaaaacg ctaccaagtg gggttcggtc gaatccagcc 14760
gcgacaacat gaactggtcg acggccgata tgatttacaa ctacgctcgc agtaacggtt 14820
ttccgttcaa attccacaca ctggtctggg ggagtcagga gcccggctgg atcagcgggc 14880
tttcggctgc agaacaacag gccgaagtga tcgaatggat ccaagcggcc ggtcagcgtt 14940
atcccgacgc agacttcgtc gacgtcgtca acgaaccgct gcacgccaaa ccttcctacc 15000
gcaatgccat cggcggagac ggctcgacag gttgggactg ggtcatctgg tcgttcgaac 15060
aggcgcgccg cgcattcccc aattccaaat tgctgattaa cgagtacggc gtcgagaacg 15120
acccgaatgc ggcgagccaa tatgtccaaa tcatcaatct gttaaaaagc cgcggcttga 15180

-continued

```
tcgacggcat cggcattcaa ggtcattatt tcaatcttga cacggtttca gtcagtacgc  15240

tgcgaaccac gctcggtatg cttgctgaaa caggtttgcc tatttatgtg tcagaactgg  15300

atatttcggg tgatgacgcc acgcaattgg ctagatatca agaaaagttc ccaattctat  15360

gggaacatcc ttctgtccaa gggattacgc tgtggggcta tattgaaggt caaacctgga  15420

gatccggcac gcatttgatt acggcttcgg gcgtggaacg acctgcgttg caatggttgc  15480

ggacgtattt ggcaggagcc ggatcctcgc cgacaccaac gccgacgccc acaccgaccg  15540

tgacaccaac ggtgacgccg acaccgacgc ctagcgcgaa cggcaccctg cgcgtcgagt  15600

atcgcgtggg cgactctagc gccaccgaca accagatgaa accgcagctg cgcatcgtca  15660

acaccggctc ccaagccgtg cctctgaccg agctgaaggt gcgctactgg tacacgaaga  15720

actcgacgca ggccgaacag tacttctgcg actgggcgca gatcggctgc tcgaacatcc  15780

gggcgcagtt cgtgtcgctg tcgcagccgg tcagcggggc ggacagctac atcgagctga  15840

gcttcacggg cggaagcatt ccggcgggag gcaacacggg cgagatacag aaccggattc  15900

acttcacgaa ctggatgaac tacaacgaaa cggacgactg gtcgtacaac ggggcgcaga  15960

cgacgtgggg gccgtcgacg cggattacgc tgtatcgcaa cggcgtgctg gtatggggca  16020

cggagccggg cggatcgtcg acgccgacac cgacaccgac gccgacccct acgcctacgc  16080

cgagcgcggc gcccacaccg gcgccgtcgg ccggcggcag cctggtcgtg cagtatcgcg  16140

cggcggacac gaacgcgacg gacaaccagc tgaagccgca ttttcggatt gtgaaccgcg  16200

ggacgacgag cgtgccgctg tcggagctaa cgattcggta ctggtacacg gtagacggag  16260

acaagccgca ggtgttcaac tgcgactggg cgcaggtggg ctgctcaaac gtgcggggca  16320

gcttcgtgaa gctttcgacg ggccggacgg gggcggacta ctatattgag atcacgttca  16380

cgtcaggcgc ggggagcctg gcgcctgggg cgaacagcgg agacattcag gcgcggatca  16440

acaagaacga ctggacgaac tacaacgagg cgaacgacta ctcgtatgat ccgacgaaga  16500

cgagttttgc ggattggaac cgggtgacgc tgtatcggaa cggtcagctc atctggggcg  16560

tcgaaccctg a                                                       16571
```

<210> SEQ ID NO 8
<211> LENGTH: 997
<212> TYPE: PRT
<213> ORGANISM: Paenibacillus species A59

<400> SEQUENCE: 8

```
Met Lys Gly Ser Trp Trp Arg Arg Val Val Ile Leu Ala Leu Ser Thr
1               5                   10                  15

Gly Leu Leu Ala Gly Ser Thr Ser Ile Gln Ala Trp Asn Gly Lys Ala
            20                  25                  30

Asp Ala Ala Ala Gly Asn His Asn Tyr Ala Glu Ala Leu Gln Lys Ala
        35                  40                  45

Ile Tyr Phe Tyr Glu Thr Gln Arg Ser Gly Lys Leu Pro Glu Asp Asn
    50                  55                  60

Arg Val Glu Trp Arg Gly Asp Ser Gly Leu Asn Asp Gly Ala Asp Val
65                  70                  75                  80

Gly Val Asp Leu Thr Gly Gly Trp Tyr Asp Ala Gly Asp His Val Lys
                85                  90                  95

Phe Gly Val Pro Met Ala Tyr Ser Ala Thr Met Leu Ala Trp Ser Val
            100                 105                 110

Val Glu Tyr Arg Glu Gly Tyr Glu Gln Ala Gly Gln Leu Glu Glu Ile
        115                 120                 125
```

-continued

```
Lys Asp Asn Leu Lys Trp Ala Thr Asp Tyr Phe Val Arg Ala His Thr
    130                 135                 140

Lys Pro Asn Glu Leu Trp Gly Gln Val Gly Ala Gly Asn Thr Asp His
145                 150                 155                 160

Ala Trp Trp Gly Pro Ala Glu Val Met Gln Met Asn Arg Pro Ala Tyr
                165                 170                 175

Lys Ile Asp Ala Ser Cys Pro Gly Ser Glu Leu Ala Gly Glu Thr Ala
            180                 185                 190

Ala Ala Leu Ala Ser Ser Ser Ile Val Phe Arg Asp Ser Asp Pro Ala
        195                 200                 205

Tyr Ala Asn Lys Leu Leu Gln His Ala Lys Glu Leu Tyr Ser Phe Ala
    210                 215                 220

Asp Thr Tyr Arg Gly Lys Tyr Ser Asp Cys Ile Thr Asp Ala Gln Ser
225                 230                 235                 240

Phe Tyr Asn Ser Trp Thr Gly Tyr Tyr Asp Glu Leu Ala Trp Ala Ala
                245                 250                 255

Thr Trp Leu Tyr Met Ala Thr Asn Asp Ser Ala Tyr Leu Ser Lys Ala
            260                 265                 270

Ile Ala Thr Ala Asn Leu Trp Gln Ala Asp Gly Gln Ser Gly Asn Trp
        275                 280                 285

Ala Tyr Thr Trp Thr Gln Gly Trp Asp Asp Lys His Tyr Gly Ala Gln
    290                 295                 300

Ile Leu Leu Ala Arg Ile Thr Ser Ser Leu Asn Met Pro Glu Ala Ala
305                 310                 315                 320

Arg Phe Ile Gln Ser Thr Glu Arg Asn Leu Asp Tyr Trp Ser Val Gly
                325                 330                 335

Thr Asn Gly Gln Arg Ile Lys Tyr Thr Pro Gly Gly Leu Ala Trp Leu
            340                 345                 350

Asp Thr Trp Gly Ser Leu Arg Tyr Ala Ala Asn Ala Ser Phe Ile Ala
        355                 360                 365

Phe Val Tyr Ser Asp Trp Val Ser Asp Pro Val Lys Lys Ala Arg Tyr
    370                 375                 380

Gln Asp Phe Ala Val Ser Gln Met Asn Tyr Ile Leu Gly Asp Asn Pro
385                 390                 395                 400

Arg Gln Ser Ser Tyr Val Val Gly Tyr Gly Gln Asn Pro Pro Lys His
                405                 410                 415

Pro His His Arg Thr Ser His Ser Ser Trp Thr Asn Asn Glu Asn Val
            420                 425                 430

Pro Ser Glu His Arg His Thr Leu Tyr Gly Ala Met Val Gly Gly Pro
        435                 440                 445

Asp Ala Ser Asp Ala Tyr Thr Asp Ser Ile Gly Asp Tyr Val Ser Asn
    450                 455                 460

Glu Val Ala Thr Asp Tyr Asn Ala Gly Phe Thr Gly Ala Leu Ala Lys
465                 470                 475                 480

Met Asn Leu Leu Phe Gly Gln Asn Asn Gln Pro Ile Ala Asn Phe Pro
                485                 490                 495

Ala Pro Glu Val Lys Ser Asp Glu Phe Phe Val Glu Ala Ser Val Lys
            500                 505                 510

Ala Ser Gly Ser Asn Tyr Thr Glu Ile Lys Ala Gln Leu Asn Asn Arg
        515                 520                 525

Ser Gly Trp Pro Ala Arg Met Gly Asp Lys Leu Ser Phe Arg Tyr Phe
    530                 535                 540
```

-continued

```
Val Asp Leu Ser Glu Val Tyr Ala Ala Gly Tyr Thr Val Ser Asp Val
545                 550                 555                 560

His Val Thr Thr Ala Tyr Ala Glu Gly Ala Ile Val Ser Gln Pro Asp
                565                 570                 575

Val Val Asp Ala Val Lys Arg Ile Tyr Ala Val Thr Ala Asp Phe Thr
            580                 585                 590

Gly Thr Lys Ile Tyr Pro Gly Gly Glu Gly His Tyr Arg Lys Glu Val
        595                 600                 605

Gln Phe Arg Ile Thr Gly Pro Glu Gly Ala Trp Asn Ala Asn Asn Asp
    610                 615                 620

His Ser Phe Gln Gly Leu Gly Thr Gly Asn Val Ala Lys Ser Ala Tyr
625                 630                 635                 640

Leu Pro Val Tyr Asp Ala Gly Ile Arg Ile Tyr Gly Gln Glu Pro Gly
                645                 650                 655

Ile Thr Pro Val Val Thr Pro Ile Ala Pro Ser Gly Val Gln Ala Val
            660                 665                 670

Ser Gly Asn Ala Gln Val Ile Leu Asn Trp Ile Ala Ser Pro Gly Ala
        675                 680                 685

Glu Ser Tyr Thr Val Lys Arg Ala Glu Val Asn Gly Gly Pro Tyr Thr
    690                 695                 700

Ser Val Ala Thr Asn Val Leu Gly Leu Thr Tyr Thr Asn Thr Gly Leu
705                 710                 715                 720

Thr Asn Gly Lys Thr Tyr Tyr Tyr Val Val Thr Ala Val Asn Ser Val
                725                 730                 735

Gly Glu Ser Pro Gly Ser Ala Gln Ala Thr Ala Thr Pro Gln Ala Gly
            740                 745                 750

Thr Ser Leu Pro Gly Ala Leu Thr Leu Ser Gly Thr Ala Gly Asn Thr
        755                 760                 765

Gln Ser Ile Leu Thr Trp Thr Ala Ala Thr Gly Ala Val Ser Tyr Lys
    770                 775                 780

Val Gln Arg Ala Ala Gly Gly Ser Ala Tyr Ala Asp Val Ala Thr Gly
785                 790                 795                 800

Leu Ala Val Leu Asn Tyr Thr Asp Ala Thr Ala Ala Asn Gly Thr Ala
                805                 810                 815

Tyr Ser Tyr Arg Ile Ala Ala Val Asn Ala Ser Gly Gln Thr Leu Ser
            820                 825                 830

Asn Ile Val Thr Leu Thr Pro Ser Ala Pro Pro Ala Thr Thr Gly Thr
        835                 840                 845

Leu Glu Val Gln Tyr Arg Asn Gly Gly Ser Gly Ala Ser Gly Asn Ala
    850                 855                 860

Val Thr Pro Gln Phe Asn Leu Lys Asn Thr Gly Thr Gln Pro Ile Asp
865                 870                 875                 880

Leu Ser Thr Val Lys Leu Arg Tyr Tyr Phe Thr Lys Asp Gly Thr Gly
                885                 890                 895

Asp Leu Thr Phe Trp Cys Asp Tyr Ala Gln Ile Gly Ser Ala Asn Ile
            900                 905                 910

Glu Gly Lys Phe Val Thr Leu Asn Pro Ala Lys Gly Thr Ala Asp Thr
        915                 920                 925

Val Leu Glu Ile Ser Phe Gln Ser Gly Ala Gly Ser Leu Ala Ala Gly
    930                 935                 940

Ala Glu Thr Gly Val Ile Gln Gly Arg Phe Ser Lys Asn Asn Trp Ser
945                 950                 955                 960

Asn Phe Asp Gln Ser Asn Asp Tyr Ser Tyr Asp Ala Thr Lys Thr Ala
```

```
                965                 970                 975

Phe Thr Thr Trp Asn Gln Val Ile Gly Tyr Gln Gly Gly Thr Lys Val
            980                 985                 990

Trp Gly Ile Glu Pro
        995


<210> SEQ ID NO 9
<211> LENGTH: 960
<212> TYPE: PRT
<213> ORGANISM: Paenibacillus borealis

<400> SEQUENCE: 9

Met Lys Leu Ser Ser Ile Lys Lys Pro Phe Ser Ile Val Met Ala Ala
1               5                   10                  15

Ile Leu Ile Ile Ser Leu Thr Ser Gly Ile Phe Asn Phe Arg Pro Gly
            20                  25                  30

Thr Ala Lys Ala Ala Ser Val Glu Lys Thr Arg Phe Leu Gln Leu Tyr
        35                  40                  45

Ala Gln Leu Lys Asp Pro Ala Ser Gly Tyr Phe Ser Ala Glu Gly Ile
    50                  55                  60

Pro Tyr His Ser Val Glu Thr Leu Leu Ser Glu Ala Pro Asn Tyr Gly
65                  70                  75                  80

His Met Thr Thr Ser Glu Ala Tyr Ser Tyr Trp Met Trp Leu Glu Val
                85                  90                  95

Leu Tyr Gly Tyr Asn Thr Gly Asp Trp Ser Lys Leu Glu Ala Ala Trp
            100                 105                 110

Asp Asn Met Glu Lys Tyr Ile Ile Pro Ile Asn Glu Gly Asp Gly Val
        115                 120                 125

Gln Glu Gln Pro Thr Met Asn Asn Tyr Asn Pro Asn Ser Pro Ala Thr
    130                 135                 140

Tyr Ala Ser Glu Leu Ala Gln Pro Asp Gln Tyr Pro Ser Ala Leu Asn
145                 150                 155                 160

Gly Lys Tyr Ala Pro Gly Lys Asp Pro Leu Asp Ala Glu Leu Lys Ala
                165                 170                 175

Ala Tyr Gly Asn Asn Gln Thr Tyr Leu Met His Trp Leu Val Asp Val
            180                 185                 190

Asp Asn Trp Tyr Gly Phe Gly Asn Leu Leu Asn Pro Thr His Thr Ala
        195                 200                 205

Ala Tyr Val Asn Thr Phe Gln Arg Gly Val Gln Glu Ser Val Trp Glu
    210                 215                 220

Ala Val Ala His Pro Ser Gln Asp Asp Lys Ser Phe Gly Lys Thr Asn
225                 230                 235                 240

Glu Gly Phe Met Ser Leu Phe Thr Lys Glu Asn Ser Val Pro Ser Ala
                245                 250                 255

Gln Trp Arg Tyr Thr Asn Ala Thr Asp Ala Asp Ala Arg Ala Val Gln
            260                 265                 270

Ala Met Tyr Trp Ala Lys Asp Leu Gly Tyr Thr Asn Thr Val Tyr Leu
        275                 280                 285

Asn Lys Ala Lys Lys Met Gly Asp Phe Leu Arg Tyr Gly Met Tyr Asp
    290                 295                 300

Lys Tyr Phe Gln Lys Val Gly Ser Ala Ala Asp Gly Thr Pro Glu Ala
305                 310                 315                 320

Gly Thr Gly Lys Asp Ser Ser Gln Tyr Leu Leu Ala Trp Tyr Thr Ala
                325                 330                 335
```

-continued

```
Trp Gly Gly Gly Leu Gly Thr Thr Gly Asn Trp Ala Trp Arg Ile Gly
            340                 345                 350

Ala Ser His Ala His Gln Gly Tyr Gln Asn Val Val Ala Ala Tyr Ala
        355                 360                 365

Leu Ser Thr Ala Asp Gly Gly Leu Ile Pro Ala Ser Ala Thr Ala Gly
    370                 375                 380

Glu Asp Trp Gly Lys Ser Leu Thr Arg Gln Leu Glu Phe Tyr Asn Trp
385                 390                 395                 400

Leu Gln Ser Ser Glu Gly Ala Ile Ala Gly Gly Ala Thr Asn Ser Tyr
                405                 410                 415

Gly Gly Ser Tyr Ser Ala Tyr Pro Ser Gly Thr Ser Thr Phe Tyr Gly
            420                 425                 430

Met Ala Tyr Asp Glu Ala Pro Val Tyr His Asp Pro Pro Ser Asn Asn
        435                 440                 445

Trp Phe Gly Met Gln Ala Trp Ser Leu Glu Arg Val Ala Glu Leu Tyr
    450                 455                 460

Tyr Ile Leu Ala Ser Ser Gly Asp Thr Thr Ser Ala Asn Phe Lys Met
465                 470                 475                 480

Ala Lys Arg Val Ile Glu Asn Trp Ile Asp Trp Ser Ala Asp Tyr Ala
                485                 490                 495

Phe Ala Gly Ser Arg Pro Val Thr Asp Ala Ala Gly Tyr Tyr Leu Asp
            500                 505                 510

Leu Gln Gly Asn Arg Ile Leu Gly Gly Asp Asp Pro Gln Ile Ala Thr
        515                 520                 525

Val Ser Ala Pro Gly Glu Phe Trp Ile Pro Gly Asn Val Glu Trp Gln
    530                 535                 540

Gly Gln Pro Asp Thr Trp Ser Gly Phe Ser Ser Phe Ser Gly Asn Ser
545                 550                 555                 560

Gly Leu Lys Ala Val Thr Lys Asp Pro Gly Gln Asp Thr Gly Val Leu
                565                 570                 575

Gly Ser Tyr Ile Lys Ala Leu Thr Phe Phe Ala Ala Gly Asn Lys Ala
            580                 585                 590

Glu His Gly Ser Tyr Thr Ala Leu Gly Gly Thr Ala Ser Gln Leu Ala
        595                 600                 605

Lys Ser Leu Leu Asp Thr Ala Trp Gly Tyr Asn Asp Gly Val Gly Ile
    610                 615                 620

Thr Thr Leu Glu Lys Arg Ala Asp Tyr Phe Arg Phe Phe Thr Lys Glu
625                 630                 635                 640

Val Tyr Phe Pro Ala Gly Trp Thr Gly Thr Phe Gly Gln Gly Asn Thr
                645                 650                 655

Ile Pro Gly Ser Ser Thr Val Pro Ser Asp Pro Ala Lys Gly Gly Asn
            660                 665                 670

Gly Val Tyr Ala Ser Tyr Thr Asp Val Leu Pro Asp Ile Lys Asn Asp
        675                 680                 685

Pro Lys Trp Ser Tyr Leu Glu Gly Lys Tyr Asn Ser Ser Tyr Asn Lys
    690                 695                 700

Thr Thr Lys Thr Trp Asp Asn Gly Ala Pro Glu Phe Thr Tyr His Arg
705                 710                 715                 720

Phe Trp Ser Gln Val Asp Ile Ala Thr Ala Tyr Ala Glu Tyr Asp Arg
                725                 730                 735

Leu Ile Asn Asn Gly Ser Gly Pro Ile Pro Thr Ala Thr Pro Thr Thr
            740                 745                 750

Thr Pro Thr Ala Thr Pro Thr Val Thr Pro Thr Ala Thr Pro Thr Ala
```

```
        755                 760                 765

Thr Pro Thr Val Thr Pro Thr Ala Thr Pro Thr Val Thr Pro Thr Ala
    770                 775                 780

Thr Pro Ile Ala Thr Pro Thr Ala Thr Pro Thr Ala Thr Pro Thr Ala
785                 790                 795                 800

Thr Pro Thr Ala Thr Pro Ala Ala Ala Asn Leu Val Val Gln Tyr Arg
                805                 810                 815

Thr Thr Asp Thr Asn Ala Thr Asp Gln Gln Phe Arg Pro Gln Leu Arg
            820                 825                 830

Ile Val Asn Asn Gly Thr Thr Ala Val Asp Leu Ser Lys Val Lys Leu
        835                 840                 845

Arg Tyr Tyr Tyr Thr Ile Asp Gly Glu Lys Ala Gln Gln Phe Asn Val
    850                 855                 860

Asp Tyr Ala Thr Leu Gly Gly Ser Asn Val Leu Gly Ser Phe Val Lys
865                 870                 875                 880

Leu Glu Pro Ala Val Ala Gly Ala Asp Tyr Tyr Val Glu Ile Ser Phe
                885                 890                 895

Ser Thr Gly Ala Gly Ser Leu Ala Pro Gly Ala Asn Thr Gly Glu Ile
            900                 905                 910

Gln Leu Arg Ile Asn Lys Thr Asp Trp Ser Asn Tyr Asn Lys Ala Asp
        915                 920                 925

Asp Tyr Ser Tyr Asp Ser Thr Lys Thr Ala Tyr Thr Asp Trp Asn Arg
    930                 935                 940

Val Thr Leu Tyr Leu Asn Gly Val Arg Val Trp Gly Val Gln Pro Gln
945                 950                 955                 960


<210> SEQ ID NO 10
<211> LENGTH: 318
<212> TYPE: PRT
<213> ORGANISM: Cohnella laeviribosi

<400> SEQUENCE: 10

Met Ser Lys Ala Lys Ala Met Lys Ile Cys Ala Ser Leu Leu Leu Leu
1               5                   10                  15

Gly Ser Val Phe Ser Phe Ile Ala Thr Ser Asp Ala Asp Ala Gly Leu
            20                  25                  30

Ala Arg Ser Lys Phe Leu Gly Asn Val Ile Ala Ser Ser Val Pro Ser
        35                  40                  45

Asn Phe Ala Thr Tyr Trp Asn Gln Val Thr Pro Glu Asn Ser Thr Lys
    50                  55                  60

Trp Gly Ser Val Glu Ala Thr Arg Asn Val Met Asn Trp Ser Ala Ala
65                  70                  75                  80

Asp Leu Ala Tyr Asn Tyr Ala Lys Ser Asn Gly Phe Pro Phe Lys Phe
                85                  90                  95

His Thr Leu Val Trp Gly Ser Gln Gln Pro Gly Trp Ile Ser Gly Leu
            100                 105                 110

Ser Gln Ala Glu Gln Lys Ala Glu Val Leu Gln Trp Ile Gln Ala Ala
        115                 120                 125

Gly Gln Arg Tyr Pro Asn Ala Asp Phe Val Asp Val Val Asn Glu Pro
    130                 135                 140

Leu His Ala Lys Pro Ser Tyr Arg Asn Ala Ile Gly Gly Asp Gly Ala
145                 150                 155                 160

Thr Gly Trp Asp Trp Val Ile Trp Ser Phe Gln Glu Ala Arg Lys Ala
                165                 170                 175
```

Phe Pro Asn Ala Lys Leu Leu Ile Asn Glu Tyr Gly Ile Ile Ser Asp
180 185 190

Pro Asn Ala Ala Asn Gln Tyr Val Gln Ile Ile Asn Leu Leu Lys Ser
195 200 205

Arg Gly Leu Ile Asp Gly Ile Gly Ile Gln Cys His Tyr Phe Asn Met
210 215 220

Asp Ser Val Ser Val Ser Thr Met Asn Ser Val Leu Asn Thr Leu Ala
225 230 235 240

Ala Thr Gly Leu Pro Ile Tyr Val Ser Glu Leu Asp Met Thr Gly Asp
245 250 255

Asp Ser Thr Gln Leu Ala Arg Tyr Gln Gln Lys Phe Pro Val Leu Trp
260 265 270

Glu His Ser Ala Val Lys Gly Val Thr Leu Trp Gly Tyr Ile Glu Gly
275 280 285

Gln Thr Trp Ala Ser Asn Thr His Leu Val Arg Ser Asn Gly Thr Glu
290 295 300

Arg Pro Ala Leu Gln Trp Leu Arg Thr Tyr Leu Ser Thr His
305 310 315

<210> SEQ ID NO 11
<211> LENGTH: 930
<212> TYPE: PRT
<213> ORGANISM: Caldibacillus cellulovorans

<400> SEQUENCE: 11

Met Asn Arg Arg Leu Ile Ala Arg Leu Ser Gly Met Leu Ala Met Val
1 5 10 15

Leu Ile Ala Ala Met Leu Ala Tyr Val Pro Lys Pro Glu Pro Ala Glu
20 25 30

Ala His Gly Gly Met Val Phe Pro Ala Thr Arg Thr Tyr Ala Cys Tyr
35 40 45

Val Asp Gly Lys Val His Gly Asn Gly Gly Asp Leu Asn Met Ile Asn
50 55 60

Pro Ala Cys Leu Asp Ala Leu Ala Ile Ser Gly Asn Tyr Gln Phe Trp
65 70 75 80

Asn Trp Phe Gly Asn Leu Ile Ser Asn Ala Gly Gly Arg His Arg Glu
85 90 95

Ile Ile Pro Asp Gly Lys Leu Cys Gly Pro Thr Ala Ser Phe Asp Gly
100 105 110

Met Asn Gln Ala Arg Thr Asp Trp Trp Thr Thr Arg Leu Gln Pro Gly
115 120 125

Ala Thr Ile Thr Val Arg Val Asn Ala Trp Ala Pro His Pro Gly Thr
130 135 140

Trp Tyr Leu Tyr Val Thr Arg Asp Gly Trp Asp Pro Thr Gln Pro Leu
145 150 155 160

Lys Trp Ser Asp Leu Glu Pro Thr Pro Phe Ser Gln Val Thr Asn Pro
165 170 175

Pro Ile Asn Ser Ser Gly Pro Asp Gly Ala Glu Tyr Ser Trp Gln Val
180 185 190

Gln Leu Pro Asn Lys Gln Gly Arg His Ile Ile Tyr Met Ile Trp Gln
195 200 205

Arg Ser Asp Ser Pro Glu Ala Phe Tyr Asn Cys Ser Asp Val Tyr Phe
210 215 220

Gly Ser Gly Pro Ile Ala Tyr Glu Phe Gly Asp Pro Arg Glu Gly Gly
225 230 235 240

-continued

```
Thr Met Ile Thr Pro Pro Pro Ser Gly Thr Thr Pro Thr Pro Thr Pro
                245                 250                 255

Thr Pro Thr Pro Thr Ser Thr Pro Thr Pro Thr Pro Thr Pro Ser Val
            260                 265                 270

Thr Pro Thr Val Thr Pro Thr Ser Thr Pro Thr Pro Ser Ala Ser Gly
        275                 280                 285

Thr Leu Arg Val Glu Tyr Arg Val Gly Asp Thr Ser Ala Thr Asp Asn
    290                 295                 300

Gln Met Lys Pro Gln Leu Arg Ile Val Asn Thr Gly Ser Gln Ala Val
305                 310                 315                 320

Pro Leu Thr Glu Leu Lys Val Arg Tyr Trp Tyr Thr Lys Asn Ser Thr
                325                 330                 335

Gln Ala Glu Gln Tyr Phe Cys Asp Trp Ala Gln Ile Gly Cys Ser Asn
            340                 345                 350

Ile Arg Ala Gln Phe Val Ser Leu Ser Gln Pro Val Ser Gly Ala Asp
        355                 360                 365

Ser Tyr Ile Glu Leu Ser Phe Thr Gly Gly Ser Ile Pro Ala Gly Gly
    370                 375                 380

Asn Thr Gly Glu Ile Gln Asn Arg Ile His Phe Thr Asn Trp Met Asn
385                 390                 395                 400

Tyr Asn Glu Thr Asp Asp Trp Ser Tyr Asn Gly Ala Gln Thr Thr Trp
                405                 410                 415

Gly Pro Ser Thr Arg Ile Thr Leu Tyr Arg Asn Gly Val Leu Val Trp
            420                 425                 430

Gly Thr Glu Pro Gly Gly Gly Ser Ser Pro Pro Thr Pro Thr Val Thr
        435                 440                 445

Pro Thr Pro Thr Pro Thr Pro Thr Ser Thr Pro Thr Pro Thr Pro Thr
    450                 455                 460

Pro Thr Ser Thr Pro Thr Pro Ser Gly Gly Pro Asn Leu Ser Val Asn
465                 470                 475                 480

Thr Gln Gly Leu Val Gly Ile Asn His Pro His Ala Trp Tyr Arg Asp
                485                 490                 495

Arg Leu Ser Ser Ser Leu Gln Gly Ile Arg Ser Trp Gly Ala Asn Ala
            500                 505                 510

Val Arg Ile Val Leu Ser Asn Gly Cys Arg Trp Thr Lys Ile Pro Ala
        515                 520                 525

Ser Glu Val Ala Asp Ile Ile Ser Gln Ala Arg Thr Leu Gly Tyr Arg
    530                 535                 540

Ala Val Val Leu Glu Val His Asp Thr Thr Gly Tyr Gly Glu Asp Ala
545                 550                 555                 560

Ala Ala Cys Ser Met Thr Thr Ala Val Asn Tyr Trp Ile Glu Leu Lys
                565                 570                 575

Asn Val Leu Ala Gly Gln Glu Asn Phe Val Ile Val Asn Ile Gly Asn
            580                 585                 590

Glu Pro Tyr Gly Asn Asn Asn Tyr Gln Asn Trp Val Thr Asp Thr Arg
        595                 600                 605

Asn Ala Val Gln Ala Leu Arg Asn Ala Gly Ile Asn Asn Thr Ile Met
    610                 615                 620

Val Asp Ala Pro Asn Trp Gly Gln Asp Trp Ser Phe Thr Met Arg Asp
625                 630                 635                 640

Asn Ala Pro Thr Ile Phe Asn Ala Asp Pro Gln Arg Asn Leu Val Phe
                645                 650                 655
```

```
Ser Ile His Met Tyr Gly Val Tyr Asp Thr Ala Ala Glu Val Gln Ser
            660                 665                 670

Tyr Ile Glu Ser Phe Val Asn Arg Gly Leu Pro Leu Val Ile Gly Glu
        675                 680                 685

Phe Gly His Met His Ser Asp Gly Asp Pro Asn Glu Gln Ala Ile Val
    690                 695                 700

Gln Tyr Ala Lys Gln Tyr Asn Ile Gly Leu Phe Gly Trp Ser Trp Ser
705                 710                 715                 720

Gly Asn Gly Gly Gly Val Glu Tyr Leu Asp Met Val Thr Asn Phe Asn
                725                 730                 735

Ala Asn Ser Pro Thr Ala Trp Gly Thr Trp Phe Arg Thr Asn Ala Ile
            740                 745                 750

Gly Thr Ser Thr Ser Pro Thr Pro Thr Pro Thr Pro Thr Pro Thr Pro
        755                 760                 765

Thr Pro Thr Pro Thr Pro Thr Pro Ser Ala Gly Gly Asn Leu Val Val
    770                 775                 780

Gln Tyr Arg Ala Ala Asp Thr Asn Ala Thr Asp Asn Gln Leu Lys Pro
785                 790                 795                 800

His Phe Arg Ile Val Asn Arg Gly Thr Ser Ser Val Pro Leu Ser Glu
                805                 810                 815

Leu Thr Ile Arg Tyr Trp Tyr Thr Val Asp Gly Asp Lys Pro Gln Val
            820                 825                 830

Phe Asn Cys Asp Trp Ala Gln Val Gly Cys Ser Asn Leu Arg Gly Ser
        835                 840                 845

Phe Val Lys Leu Ser Thr Gly Arg Thr Gly Ala Asp Tyr Tyr Ile Glu
    850                 855                 860

Ile Thr Phe Thr Ser Gly Ala Gly Ser Leu Ala Pro Gly Ala Ser Ser
865                 870                 875                 880

Gly Asp Ile Gln Val Arg Ile Asn Lys Asn Asp Trp Thr Asn Tyr Asn
                885                 890                 895

Glu Ala Asn Asp Tyr Ser Tyr Asp Pro Thr Lys Thr Ser Phe Ala Asp
            900                 905                 910

Trp Asn Arg Val Thr Leu Tyr Arg Asn Gly Gln Leu Val Trp Gly Val
        915                 920                 925

Glu Pro
    930


<210> SEQ ID NO 12
<211> LENGTH: 921
<212> TYPE: PRT
<213> ORGANISM: Caldibacillus cellulovorans

<400> SEQUENCE: 12

Met Gly Thr Gly Arg Ala Gly Glu Trp Ile Lys Lys Met Leu Leu Val
1               5                   10                  15

Leu Ala Ile Gly Leu Leu Ile Pro Ile Pro Tyr Pro His Val Ala Ser
            20                  25                  30

Ala Glu Asn Val Leu Ile Leu Gln Ser Asp Phe Glu Asp Gly Thr Thr
        35                  40                  45

Gln Gly Trp Val Gly Arg Gly Gly Val Glu Thr Leu Thr Val Thr Ser
    50                  55                  60

Ala Ala Ala Tyr Ser Gly Ala Tyr Gly Leu Ser Val Ser Gly Arg Thr
65                  70                  75                  80

Glu Thr Trp His Gly Pro Thr Leu Asp Ile Thr Ser Tyr Ile Gln Val
                85                  90                  95
```

-continued

```
Gly Lys Thr Tyr Gln Phe Ser Ala Trp Val Lys Leu Pro Ser Gly Ser
            100                 105                 110

Ser Asn Thr Arg Ile Ser Met Thr Met Gln Arg Thr Met Gln Asp Thr
        115                 120                 125

Val Tyr Tyr Glu Gln Ile Tyr Phe Asp Thr Ala Leu Ser Gly Asn Trp
    130                 135                 140

Ile Gln Leu Lys Ala Gln Tyr Lys Leu Tyr Glu Pro Ala Val Asn Leu
145                 150                 155                 160

Gln Val Tyr Phe Glu Ala Pro Asp His Ala Thr Gln Ser Phe Tyr Ile
                165                 170                 175

Asp Asp Val Arg Ile Glu Gln Leu Pro Asp Leu Pro Lys Thr Val Glu
            180                 185                 190

Glu Asn Ile Pro Ser Leu Lys Asp Val Phe Ala Gly Arg Phe Pro Ile
        195                 200                 205

Gly Thr Ala Phe Glu Asn Phe Glu Leu Leu Asp Glu Gln Asp Arg Lys
    210                 215                 220

Leu Ile Leu Lys His Phe Asn Ser Val Thr Pro Gly Asn Val Leu Lys
225                 230                 235                 240

Trp Asp Ser Thr Glu Pro Gln Glu Gly Val Phe Asn Phe Thr Glu Ser
                245                 250                 255

Asp Lys Ala Val Ala Phe Ala Val Gln Asn Gly Met Lys Ile Arg Gly
            260                 265                 270

His Thr Leu Ile Trp His Asn Gln Thr Pro Asn Trp Val Phe Tyr Asp
        275                 280                 285

Ser Asn Gly Asn Leu Val Ser Lys Glu Val Leu Tyr Gln Arg Met Glu
    290                 295                 300

Arg His Ile Lys Thr Val Val Ser Arg Tyr Lys Gly Ile Ile Tyr Ala
305                 310                 315                 320

Trp Asp Val Val Asn Glu Val Ile Asp Pro Gly Gln Pro Asp Gly Leu
                325                 330                 335

Arg Arg Ser Leu Trp Tyr Gln Ile Ala Gly Glu Glu Tyr Ile Glu Lys
            340                 345                 350

Ala Phe Gln Phe Ala His Glu Ala Asp Pro Asn Ala Leu Leu Phe Ile
        355                 360                 365

Asn Asp Tyr Asn Thr His Glu Ser Gly Lys Ser Gln Ala Leu Tyr Asn
    370                 375                 380

Leu Val Gln Arg Leu Lys Ser Lys Gly Ile Pro Val His Gly Val Gly
385                 390                 395                 400

His Gln Thr His Ile Asn Ile Thr Trp Pro Ser Ile Ser Glu Ile Glu
                405                 410                 415

Asn Ser Leu Val Lys Phe Ser Asn Leu Gly Val Val Gln Glu Ile Thr
            420                 425                 430

Glu Leu Asp Met Ser Ile Tyr Asn Asn Ser Ser Gln Lys Tyr Asp Thr
        435                 440                 445

Leu Pro Ser Asp Leu Ala Gln Gln Gln Ala Thr Arg Tyr Arg Gln Leu
    450                 455                 460

Phe Glu Met Phe Leu Arg Arg Ser Ser Leu Ile Gln Asn Val Thr Phe
465                 470                 475                 480

Trp Gly Lys Asp Asp Ala Asn Thr Trp Leu Arg Lys Phe Pro Val Val
                485                 490                 495

Arg Asn Asp Trp Pro Leu Leu Phe Asp Glu Gln Leu Lys Ala Lys Pro
            500                 505                 510
```

-continued

```
Ala Tyr Trp Ala Val Val Gly Thr Val Pro Ser Pro Thr Pro Thr Pro
        515                 520                 525

Thr Ser Thr Ala Thr Pro Thr Pro Thr Pro Thr Val Ile Pro Thr Pro
    530                 535                 540

Thr Pro Thr Pro Thr Pro Thr Ser Thr Pro Thr Pro Thr Pro Thr Pro
545                 550                 555                 560

Ser Ala Ser Gly Thr Leu Arg Val Glu Tyr Arg Val Gly Asp Ser Ser
                565                 570                 575

Ala Thr Asp Asn Gln Met Lys Pro Gln Leu Arg Ile Val Asn Thr Gly
            580                 585                 590

Ser Gln Ala Val Pro Leu Thr Glu Leu Lys Val Arg Tyr Trp Tyr Thr
        595                 600                 605

Lys Asn Ser Thr Gln Ala Glu Gln Tyr Phe Cys Asp Trp Ala Gln Ile
    610                 615                 620

Gly Cys Ser Asn Ile Arg Ala Gln Phe Val Ser Leu Ala Gln Pro Val
625                 630                 635                 640

Ser Gly Ala Asp Ser Tyr Ile Glu Leu Ser Phe Thr Gly Gly Ser Val
                645                 650                 655

Pro Ala Gly Gly Asn Thr Gly Glu Ile Gln Asn Arg Ile His Phe Thr
            660                 665                 670

Asn Trp Met Asn Tyr Asn Glu Thr Asp Asp Trp Ser Tyr Asn Gly Thr
        675                 680                 685

Gln Thr Thr Trp Gly Pro Ser Thr Arg Ile Thr Leu Tyr Arg Asn Gly
    690                 695                 700

Val Leu Val Trp Gly Thr Glu Pro Gly Gly Gly Ser Ser Thr Pro Thr
705                 710                 715                 720

Pro Thr Pro Thr Pro Thr Pro Thr Pro Thr Ser Thr Pro Thr Pro Thr
                725                 730                 735

Pro Thr Pro Thr Ser Thr Pro Thr Pro Thr Pro Thr Pro Thr Ser Thr
            740                 745                 750

Pro Thr Pro Thr Ala Thr Pro Thr Pro Thr Pro Thr Pro Thr Pro Ser
        755                 760                 765

Ala Gly Gly Asn Leu Val Val Gln Tyr Arg Ala Ala Asp Thr Asn Ala
    770                 775                 780

Gly Asp Asn Gln Leu Lys Pro His Phe Arg Ile Val Asn Arg Gly Thr
785                 790                 795                 800

Thr Ser Val Pro Leu Ser Glu Leu Thr Ile Arg Tyr Trp Tyr Thr Val
                805                 810                 815

Asp Gly Asp Lys Pro Gln Val Phe Asn Cys Asp Trp Ala Trp Val Gly
            820                 825                 830

Cys Ser Asn Leu Arg Gly Ser Leu Val Lys Leu Thr Thr Gly Arg Thr
        835                 840                 845

Gly Ala Asp Tyr Tyr Leu Glu Ile Thr Phe Thr Ser Gly Ala Gly Ser
    850                 855                 860

Leu Ala Pro Gly Ala Asn Ser Gly Asp Ile Gln Ala Arg Ile Asn Lys
865                 870                 875                 880

Asn Asp Trp Thr Asn Tyr Asn Glu Ala Asn Asp Tyr Ser Tyr Asp Pro
                885                 890                 895

Thr Lys Thr Ser Phe Ala Asp Trp Asn Arg Val Thr Leu Tyr Arg Asn
            900                 905                 910

Gly Gln Leu Val Trp Gly Val Glu Pro
        915                 920
```

<210> SEQ ID NO 13
<211> LENGTH: 5
<212> TYPE: PRT
<213> ORGANISM: Paenibacillus species A59

<400> SEQUENCE: 13

Ser Gly Lys Leu Pro
1 5

<210> SEQ ID NO 14
<211> LENGTH: 5
<212> TYPE: PRT
<213> ORGANISM: Paenibacillus species A59

<400> SEQUENCE: 14

Trp Arg Gly Asp Ser
1 5

<210> SEQ ID NO 15
<211> LENGTH: 6
<212> TYPE: PRT
<213> ORGANISM: Paenibacillus species A59

<400> SEQUENCE: 15

Asp Leu Thr Gly Gly Trp
1 5

<210> SEQ ID NO 16
<211> LENGTH: 8
<212> TYPE: PRT
<213> ORGANISM: Paenibacillus species A59

<400> SEQUENCE: 16

Asp Ala Gly Asp His Val Lys Phe
1 5

<210> SEQ ID NO 17
<211> LENGTH: 6
<212> TYPE: PRT
<213> ORGANISM: Paenibacillus species A59

<400> SEQUENCE: 17

Trp Ala Val Tyr Glu Tyr
1 5

<210> SEQ ID NO 18
<211> LENGTH: 8
<212> TYPE: PRT
<213> ORGANISM: Paenibacillus species A59

<400> SEQUENCE: 18

Asp His Ala Trp Trp Gly Pro Ala
1 5

<210> SEQ ID NO 19
<211> LENGTH: 5
<212> TYPE: PRT
<213> ORGANISM: Paenibacillus species A59

<400> SEQUENCE: 19

Glu Val Met Gln Met
1 5

<210> SEQ ID NO 20
<211> LENGTH: 8

<212> TYPE: PRT
<213> ORGANISM: Paenibacillus species A59

<400> SEQUENCE: 20

Ala Val Trp Leu Tyr Leu Ala Thr
1 5

<210> SEQ ID NO 21
<211> LENGTH: 5
<212> TYPE: PRT
<213> ORGANISM: Paenibacillus species A59

<400> SEQUENCE: 21

Trp Asp Asp Val His
1 5

<210> SEQ ID NO 22
<211> LENGTH: 6
<212> TYPE: PRT
<213> ORGANISM: Paenibacillus species A59

<400> SEQUENCE: 22

Gly Leu Ala Trp Leu Asp
1 5

<210> SEQ ID NO 23
<211> LENGTH: 7
<212> TYPE: PRT
<213> ORGANISM: Paenibacillus species A59

<400> SEQUENCE: 23

Trp Gly Ser Leu Arg Tyr Ala
1 5

<210> SEQ ID NO 24
<211> LENGTH: 9
<212> TYPE: PRT
<213> ORGANISM: Paenibacillus species A59

<400> SEQUENCE: 24

Phe Leu Ala Phe Val Tyr Ser Asp Trp
1 5

<210> SEQ ID NO 25
<211> LENGTH: 8
<212> TYPE: PRT
<213> ORGANISM: Paenibacillus species A59

<400> SEQUENCE: 25

Arg Pro His His Arg Thr Ala His
1 5

<210> SEQ ID NO 26
<211> LENGTH: 6
<212> TYPE: PRT
<213> ORGANISM: Paenibacillus species A59

<400> SEQUENCE: 26

Ser Trp Ala Asp Ser Gln
1 5

<210> SEQ ID NO 27
<211> LENGTH: 6
<212> TYPE: PRT
<213> ORGANISM: Paenibacillus borealis

<400> SEQUENCE: 27

Pro Ala Asn Gly Tyr Phe
1 5

<210> SEQ ID NO 28
<211> LENGTH: 6
<212> TYPE: PRT
<213> ORGANISM: Paenibacillus borealis

<400> SEQUENCE: 28

Gly Ile Pro Tyr His Ser
1 5

<210> SEQ ID NO 29
<211> LENGTH: 7
<212> TYPE: PRT
<213> ORGANISM: Paenibacillus borealis

<400> SEQUENCE: 29

Glu Ala Pro Asp Tyr Gly His
1 5

<210> SEQ ID NO 30
<211> LENGTH: 8
<212> TYPE: PRT
<213> ORGANISM: Paenibacillus borealis

<400> SEQUENCE: 30

Thr Thr Ser Glu Ala Phe Ser Tyr
1 5

<210> SEQ ID NO 31
<211> LENGTH: 6
<212> TYPE: PRT
<213> ORGANISM: Paenibacillus borealis

<400> SEQUENCE: 31

Thr Gly Asp Trp Ser Lys
1 5

<210> SEQ ID NO 32
<211> LENGTH: 5
<212> TYPE: PRT
<213> ORGANISM: Paenibacillus borealis

<400> SEQUENCE: 32

Pro Ala Thr Tyr Ala
1 5

<210> SEQ ID NO 33
<211> LENGTH: 7
<212> TYPE: PRT
<213> ORGANISM: Paenibacillus borealis

<400> SEQUENCE: 33

Asp Val Asp Asn Trp Tyr Gly
1 5

<210> SEQ ID NO 34
<211> LENGTH: 6
<212> TYPE: PRT
<213> ORGANISM: Paenibacillus borealis

<400> SEQUENCE: 34

Asn Thr Phe Gln Arg Gly
1               5

<210> SEQ ID NO 35
<211> LENGTH: 5
<212> TYPE: PRT
<213> ORGANISM: Paenibacillus borealis

<400> SEQUENCE: 35

Glu Ser Val Trp Glu
1               5

<210> SEQ ID NO 36
<211> LENGTH: 5
<212> TYPE: PRT
<213> ORGANISM: Paenibacillus borealis

<400> SEQUENCE: 36

Gln Trp Arg Tyr Thr
1               5

<210> SEQ ID NO 37
<211> LENGTH: 8
<212> TYPE: PRT
<213> ORGANISM: Paenibacillus borealis

<400> SEQUENCE: 37

Asp Ala Asp Ala Arg Ala Ile Gln
1               5

<210> SEQ ID NO 38
<211> LENGTH: 8
<212> TYPE: PRT
<213> ORGANISM: Paenibacillus borealis

<400> SEQUENCE: 38

Lys Met Gly Asp Tyr Leu Arg Tyr
1               5

<210> SEQ ID NO 39
<211> LENGTH: 5
<212> TYPE: PRT
<213> ORGANISM: Paenibacillus borealis

<400> SEQUENCE: 39

Phe Asp Lys Tyr Phe
1               5

<210> SEQ ID NO 40
<211> LENGTH: 9
<212> TYPE: PRT
<213> ORGANISM: Paenibacillus borealis

<400> SEQUENCE: 40

Ser Ala His Tyr Leu Leu Ser Trp Tyr
1               5

<210> SEQ ID NO 41
<211> LENGTH: 5
<212> TYPE: PRT
<213> ORGANISM: Paenibacillus borealis

<400> SEQUENCE: 41

Gly Tyr Gln Asn Pro 1 5

<210> SEQ ID NO 42
<211> LENGTH: 6
<212> TYPE: PRT
<213> ORGANISM: Paenibacillus borealis

<400> SEQUENCE: 42

Gly Gly Ala Thr Asn Ser
1 5

<210> SEQ ID NO 43
<211> LENGTH: 5
<212> TYPE: PRT
<213> ORGANISM: Paenibacillus borealis

<400> SEQUENCE: 43

Thr Phe Tyr Gly Met
1 5

<210> SEQ ID NO 44
<211> LENGTH: 6
<212> TYPE: PRT
<213> ORGANISM: Paenibacillus borealis

<400> SEQUENCE: 44

Pro Val Tyr Arg Asp Pro
1 5

<210> SEQ ID NO 45
<211> LENGTH: 8
<212> TYPE: PRT
<213> ORGANISM: Paenibacillus borealis

<400> SEQUENCE: 45

Trp Phe Gly Phe Gln Ala Trp Ser
1 5

<210> SEQ ID NO 46
<211> LENGTH: 6
<212> TYPE: PRT
<213> ORGANISM: Paenibacillus borealis

<400> SEQUENCE: 46

Gly Gln Pro Asp Thr Trp
1 5

<210> SEQ ID NO 47
<211> LENGTH: 6
<212> TYPE: PRT
<213> ORGANISM: Paenibacillus borealis

<400> SEQUENCE: 47

Tyr Thr Gly Asn Pro Asn
1 5

<210> SEQ ID NO 48
<211> LENGTH: 7
<212> TYPE: PRT
<213> ORGANISM: Paenibacillus borealis

<400> SEQUENCE: 48

Tyr His Arg Phe Trp Ala Gln
1 5

<210> SEQ ID NO 49
<211> LENGTH: 6
<212> TYPE: PRT
<213> ORGANISM: Cohnella laeviribosi

<400> SEQUENCE: 49

Ala Asp Ala Gly Leu Ala
1               5

<210> SEQ ID NO 50
<211> LENGTH: 7
<212> TYPE: PRT
<213> ORGANISM: Cohnella laeviribosi

<400> SEQUENCE: 50

Lys Phe Leu Gly Asn Val Ile
1               5

<210> SEQ ID NO 51
<211> LENGTH: 9
<212> TYPE: PRT
<213> ORGANISM: Cohnella laeviribosi

<400> SEQUENCE: 51

Tyr Trp Asn Gln Val Thr Pro Glu Asn
1               5

<210> SEQ ID NO 52
<211> LENGTH: 7
<212> TYPE: PRT
<213> ORGANISM: Cohnella laeviribosi

<400> SEQUENCE: 52

Thr Lys Trp Gly Ser Val Glu
1               5

<210> SEQ ID NO 53
<211> LENGTH: 16
<212> TYPE: PRT
<213> ORGANISM: Cohnella laeviribosi

<400> SEQUENCE: 53

Ser Asn Gly Phe Pro Phe Lys Phe His Thr Leu Val Trp Gly Ser Gln
1               5                   10                  15

<210> SEQ ID NO 54
<211> LENGTH: 8
<212> TYPE: PRT
<213> ORGANISM: Cohnella laeviribosi

<400> SEQUENCE: 54

Pro Gly Trp Ile Ser Gly Leu Ser
1               5

<210> SEQ ID NO 55
<211> LENGTH: 10
<212> TYPE: PRT
<213> ORGANISM: Cohnella laeviribosi

<400> SEQUENCE: 55

Trp Ile Gln Ala Ala Gly Gln Arg Tyr Pro
1               5                   10

<210> SEQ ID NO 56

-continued

<211> LENGTH: 25
<212> TYPE: PRT
<213> ORGANISM: Cohnella laeviribosi

<400> SEQUENCE: 56

Ala Asp Phe Val Asp Val Val Asn Glu Pro Leu His Ala Lys Pro Ser
1 5 10 15

Tyr Arg Asn Ala Ile Gly Gly Asp Gly
20 25

<210> SEQ ID NO 57
<211> LENGTH: 10
<212> TYPE: PRT
<213> ORGANISM: Cohnella laeviribosi

<400> SEQUENCE: 57

Thr Gly Trp Asp Trp Val Ile Trp Ser Phe
1 5 10

<210> SEQ ID NO 58
<211> LENGTH: 8
<212> TYPE: PRT
<213> ORGANISM: Cohnella laeviribosi

<400> SEQUENCE: 58

Lys Leu Leu Ile Asn Glu Tyr Gly
1 5

<210> SEQ ID NO 59
<211> LENGTH: 5
<212> TYPE: PRT
<213> ORGANISM: Cohnella laeviribosi

<400> SEQUENCE: 59

Asp Pro Asn Ala Ala
1 5

<210> SEQ ID NO 60
<211> LENGTH: 21
<212> TYPE: PRT
<213> ORGANISM: Cohnella laeviribosi

<400> SEQUENCE: 60

Gln Tyr Val Gln Ile Ile Asn Leu Leu Lys Ser Arg Gly Leu Ile Asp
1 5 10 15

Gly Ile Gly Ile Gln
20

<210> SEQ ID NO 61
<211> LENGTH: 5
<212> TYPE: PRT
<213> ORGANISM: Cohnella laeviribosi

<400> SEQUENCE: 61

Val Ser Val Ser Thr
1 5

<210> SEQ ID NO 62
<211> LENGTH: 11
<212> TYPE: PRT
<213> ORGANISM: Cohnella laeviribosi

<400> SEQUENCE: 62

Thr Gly Leu Pro Ile Tyr Val Ser Glu Leu Asp 1 5 10

<210> SEQ ID NO 63
<211> LENGTH: 7
<212> TYPE: PRT
<213> ORGANISM: Cohnella laeviribosi

<400> SEQUENCE: 63

Thr Gln Leu Ala Arg Tyr Gln
1 5

<210> SEQ ID NO 64
<211> LENGTH: 11
<212> TYPE: PRT
<213> ORGANISM: Cohnella laeviribosi

<400> SEQUENCE: 64

Thr Leu Trp Gly Tyr Ile Glu Gly Gln Thr Trp
1 5 10

<210> SEQ ID NO 65
<211> LENGTH: 12
<212> TYPE: PRT
<213> ORGANISM: Cohnella laeviribosi

<400> SEQUENCE: 65

Glu Arg Pro Ala Leu Gln Trp Leu Arg Thr Tyr Leu
1 5 10

<210> SEQ ID NO 66
<211> LENGTH: 20
<212> TYPE: PRT
<213> ORGANISM: Caldibacillus cellulovorans

<400> SEQUENCE: 66

Met Asn Arg Arg Leu Ile Ala Arg Leu Ser Gly Met Leu Ala Met Val
1 5 10 15

Leu Ile Ala Ala
20

<210> SEQ ID NO 67
<211> LENGTH: 200
<212> TYPE: PRT
<213> ORGANISM: Caldibacillus cellulovorans

<400> SEQUENCE: 67

Leu Ala Tyr Val Pro Lys Pro Glu Pro Ala Glu Ala His Gly Gly Met
1 5 10 15

Val Phe Pro Ala Thr Arg Thr Tyr Ala Cys Tyr Val Asp Gly Lys Val
20 25 30

His Gly Asn Gly Gly Asp Leu Asn Met Ile Asn Pro Ala Cys Leu Asp
35 40 45

Ala Leu Ala Ile Ser Gly Asn Tyr Gln Phe Trp Asn Trp Phe Gly Asn
50 55 60

Leu Ile Ser Asn Ala Gly Gly Arg His Arg Glu Ile Ile Pro Asp Gly
65 70 75 80

Lys Leu Cys Gly Pro Thr Ala Ser Phe Asp Gly Met Asn Gln Ala Arg
85 90 95

Thr Asp Trp Trp Thr Thr Arg Leu Gln Pro Gly Ala Thr Ile Thr Val
100 105 110

Arg Val Asn Ala Trp Ala Pro His Pro Gly Thr Trp Tyr Leu Tyr Val

-continued

```
        115                 120                 125

Thr Arg Asp Gly Trp Asp Pro Thr Gln Pro Leu Lys Trp Ser Asp Leu
    130                 135                 140

Glu Pro Thr Pro Phe Ser Gln Val Thr Asn Pro Pro Ile Asn Ser Ser
145                 150                 155                 160

Gly Pro Asp Gly Ala Glu Tyr Ser Trp Gln Val Gln Leu Pro Asn Lys
                165                 170                 175

Gln Gly Arg His Ile Ile Tyr Met Ile Trp Gln Arg Ser Asp Ser Pro
            180                 185                 190

Glu Ala Phe Tyr Asn Cys Ser Asp
        195                 200


<210> SEQ ID NO 68
<211> LENGTH: 19
<212> TYPE: PRT
<213> ORGANISM: Caldibacillus cellulovorans

<400> SEQUENCE: 68

Tyr Phe Gly Ser Gly Pro Ile Ala Tyr Glu Phe Gly Asp Pro Arg Glu
1               5                   10                  15

Gly Gly Thr
```